(12) United States Patent
Aviv et al.

(10) Patent No.: US 12,138,164 B2
(45) Date of Patent: Nov. 12, 2024

(54) ANNULOPLASTY TECHNOLOGIES

(71) Applicant: Edwards Lifesciences Innovation (Israel) Ltd., Caesarea (IL)

(72) Inventors: Ehud Aviv, Costa Mesa, CA (US); Tal Reich, Moledet (IL); Tal Sheps, Givat Shmuel (IL); Ilia Hariton, Zichron Yaacov (IL); Haim Brauon, Beit Dagan (IL); Meir Kutzik, Holon (IL); Alexei Koifman, Melbourne (AU); Yaron Herman, Givat Ada (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 270 days.

(21) Appl. No.: 17/334,557

(22) Filed: May 28, 2021

(65) Prior Publication Data
US 2021/0282929 A1    Sep. 16, 2021

Related U.S. Application Data

(63) Continuation of application No. 16/174,731, filed on Oct. 30, 2018, now Pat. No. 11,020,227, which is a (Continued)

(51) Int. Cl.
*A61F 2/24* (2006.01)
*A61B 17/04* (2006.01)
(Continued)

(52) U.S. Cl.
CPC ........ *A61F 2/2445* (2013.01); *A61B 17/0401* (2013.01); *A61B 17/068* (2013.01);
(Continued)

(58) Field of Classification Search
CPC .... A61F 2/2445; A61F 2/2412; A61F 2/2466; A61F 2250/0004; A61F 2250/001;
(Continued)

(56) References Cited

U.S. PATENT DOCUMENTS 3,604,488 A    9/1971    Wishart et al.
3,656,185 A    4/1972    Carpentier
(Continued)

FOREIGN PATENT DOCUMENTS

CN    102686185 A    9/2012
CN    104010580 A    8/2014
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Brooke Labranche
(74) *Attorney, Agent, or Firm* — Thomas C. Richardson

(57) ABSTRACT

A method is described for use with a heart of a subject, the heart having a valve and an atrium upstream of the valve. The method includes transluminally advancing multiple tissue anchors to the atrium; and securing an elongate contraction member at least partly around an annulus of the valve by anchoring the tissue anchors to the annulus, such that the tissue anchors are distributed along the elongate contraction member. The method further includes subsequently contracting the annulus by applying tension the elongate contraction member, such that a radiopaque indicator that is disposed within the heart and that is coupled to the contraction member undergoes a conformational change in response to the tension. The conformational change of the radiopaque indicator within the heart is observed, and the tension is adjusted responsively to the observed conformational change. Other embodiments are also described.

14 Claims, 55 Drawing Sheets

Related U.S. Application Data continuation of application No. 15/782,687, filed on Oct. 12, 2017, now Pat. No. 10,765,514, which is a continuation of application No. PCT/IL2016/050433, filed on Apr. 21, 2016.

(60) Provisional application No. 62/154,962, filed on Apr. 30, 2015.

(51) Int. Cl.
*A61B 17/068* (2006.01)
*A61B 17/00* (2006.01)
*A61B 17/064* (2006.01)
*A61B 90/00* (2016.01)

(52) U.S. Cl.
CPC .. *A61F 2/2412* (2013.01); *A61B 2017/00323* (2013.01); *A61B 2017/00477* (2013.01); *A61B 2017/00783* (2013.01); *A61B 2017/0409* (2013.01); *A61B 2017/0441* (2013.01); *A61B 2017/0446* (2013.01); *A61B 2017/0496* (2013.01); *A61B 2017/0649* (2013.01); *A61B 2090/064* (2016.02); *A61B 2090/3966* (2016.02); *A61F 2/2466* (2013.01); *A61F 2250/0004* (2013.01); *A61F 2250/001* (2013.01)

(58) Field of Classification Search
CPC ............... A61B 17/0401; A61B 17/068; A61B 2017/00323; A61B 2017/00477; A61B 2017/00783; A61B 2017/0409; A61B 2017/0441; A61B 2017/0446; A61B 2017/0496; A61B 2017/0649; A61B 2090/064; A61B 2090/3966
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A | 5/1998 | Allard et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |

(56) References Cited

U.S. PATENT DOCUMENTS

| | | |
|---|---|---|
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |

(56) References Cited

U.S. PATENT DOCUMENTS

| | | |
|---|---|---|
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |

(56) References Cited

U.S. PATENT DOCUMENTS

| | | |
|---|---|---|
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0093148 A1 | 5/2003 | Bolling et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0167062 A1 | 9/2003 | Gambale et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0049211 A1 | 3/2004 | Tremulis et al. |
| 2004/0059413 A1 | 3/2004 | Argento |
| 2004/0068273 A1 | 4/2004 | Fariss et al. |
| 2004/0106950 A1 | 6/2004 | Grafton et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller et al. |

(56) References Cited

U.S. PATENT DOCUMENTS

| | | |
|---|---|---|
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0286628 A1 | 11/2010 | Gross |
| 2010/0286767 A1 | 11/2010 | Zipory et al. |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |

(56) References Cited

U.S. PATENT DOCUMENTS

| | | |
|---|---|---|
| 2011/0301498 A1 | 12/2011 | Maenhout et al. |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0101571 A1 | 4/2012 | Thambar et al. |
| 2012/0109155 A1 | 5/2012 | Robinson et al. |
| 2012/0136436 A1 | 5/2012 | Cabiri et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0218206 A1 | 8/2013 | Gadlage |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1* | 3/2015 | Gross ............... A61F 2/2445 623/2.37 |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117113 A1 | 4/2019 | Curran |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1 | 1/2020 | Brauon et al. |
| 2020/0178956 A1 | 6/2020 | Mitelberg et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0052387 A1 | 2/2021 | Greenan et al. |

(56) References Cited

U.S. PATENT DOCUMENTS

| | | |
|---|---|---|
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0257196 A1 | 8/2022 | Massmann |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |
| 2023/0320856 A1 | 10/2023 | Zarbatany et al. |

FOREIGN PATENT DOCUMENTS

| | | |
|---|---|---|
| CN | 113331995 A | 9/2021 |
| EP | 1034753 A1 | 9/2000 |
| EP | 2554139 A1 | 2/2013 |
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2006105084 A2 | 10/2006 |
| WO | 2007098512 A1 | 9/2007 |
| WO | 2010000454 A1 | 1/2010 |
| WO | 2010065274 A1 | 6/2010 |
| WO | 2010073246 A2 | 7/2010 |
| WO | 2012176195 A3 | 3/2013 |
| WO | 2013069019 A2 | 5/2013 |
| WO | 2014064694 A2 | 5/2014 |
| WO | 2014064964 A1 | 5/2014 |
| WO | 2014087402 A1 | 6/2014 |
| WO | 2016087934 A1 | 6/2016 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. Ring+String, Successful Repair technique for ischemic mitral regurgitation with severe leaflet Tethering, The Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

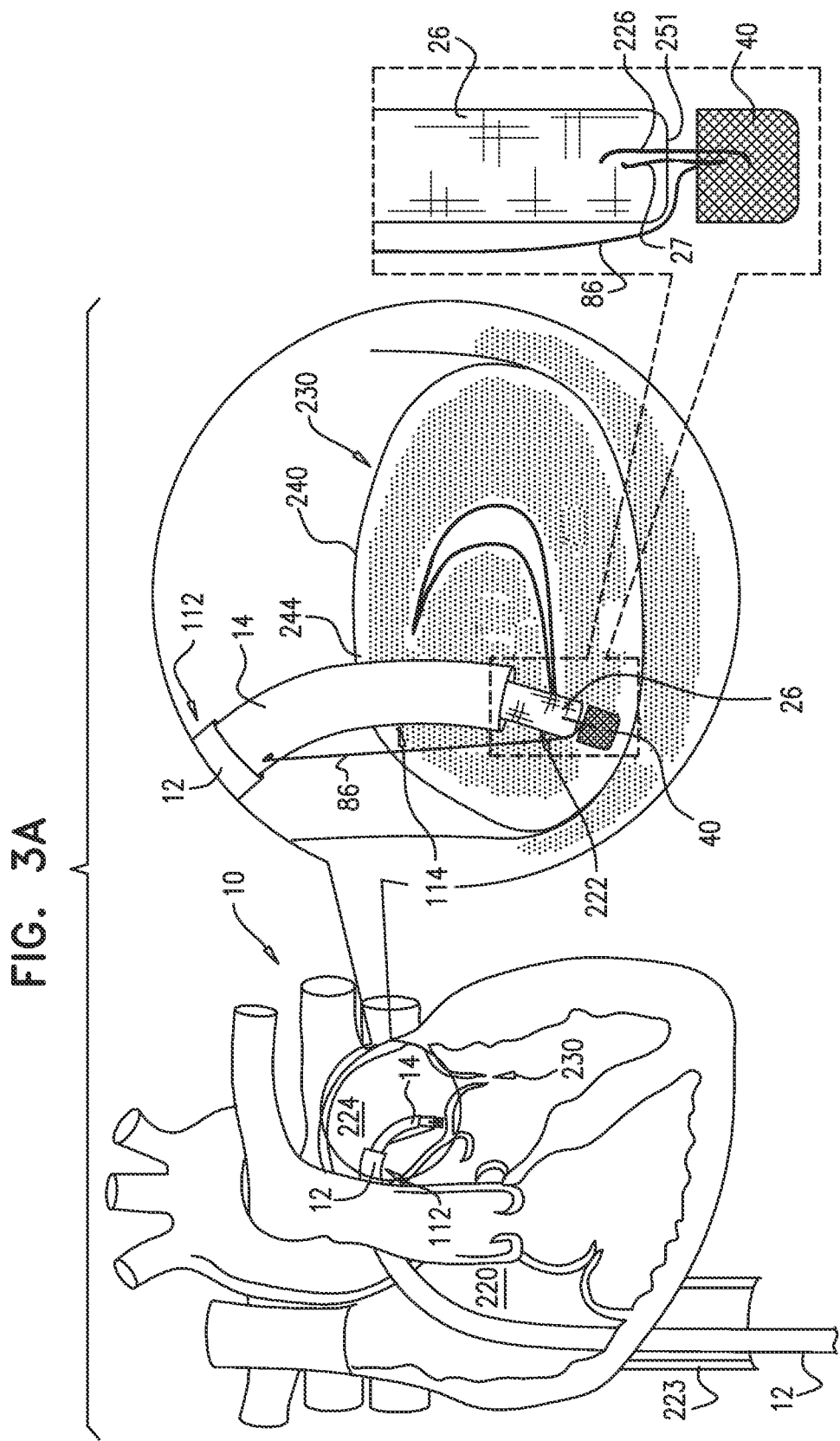

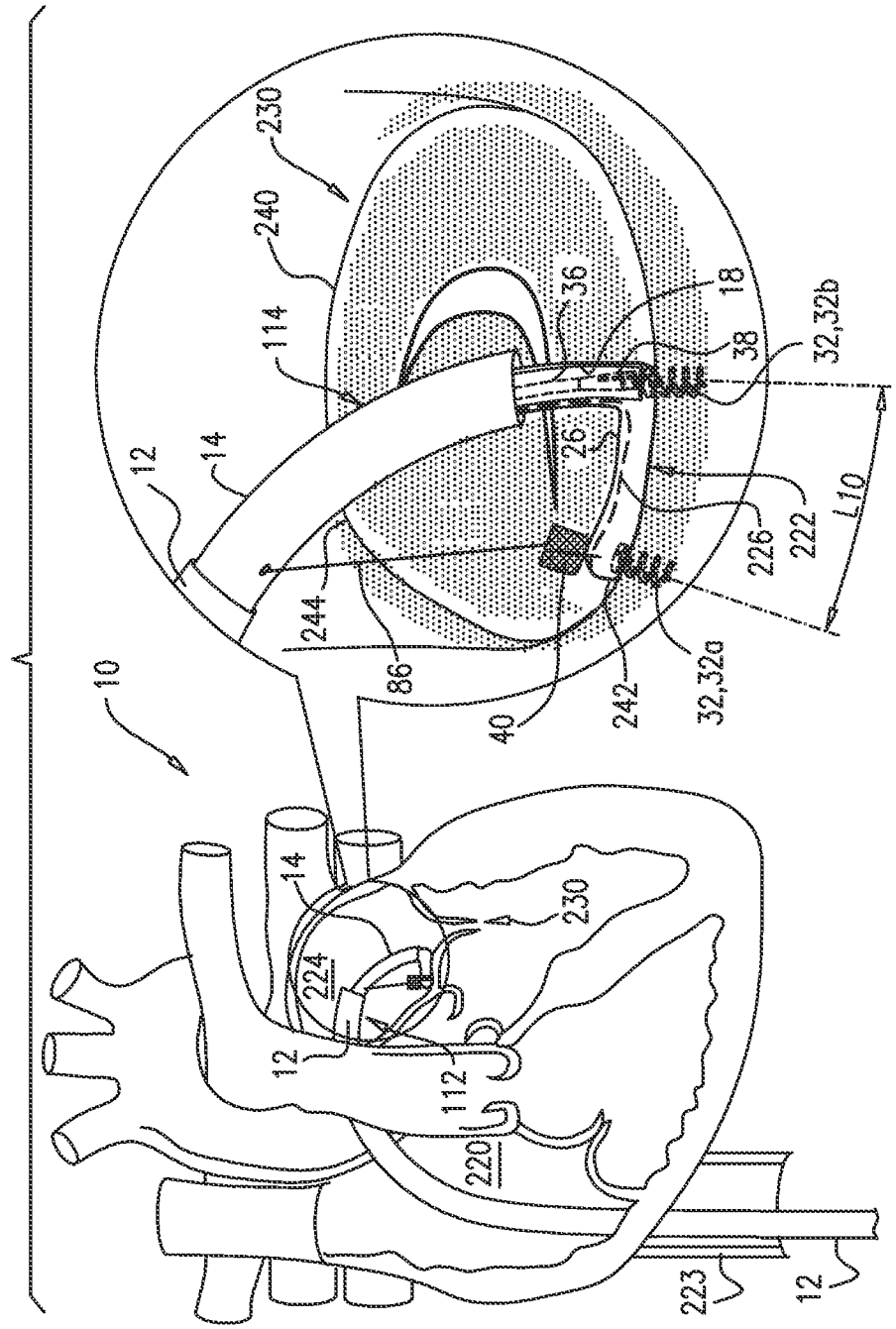

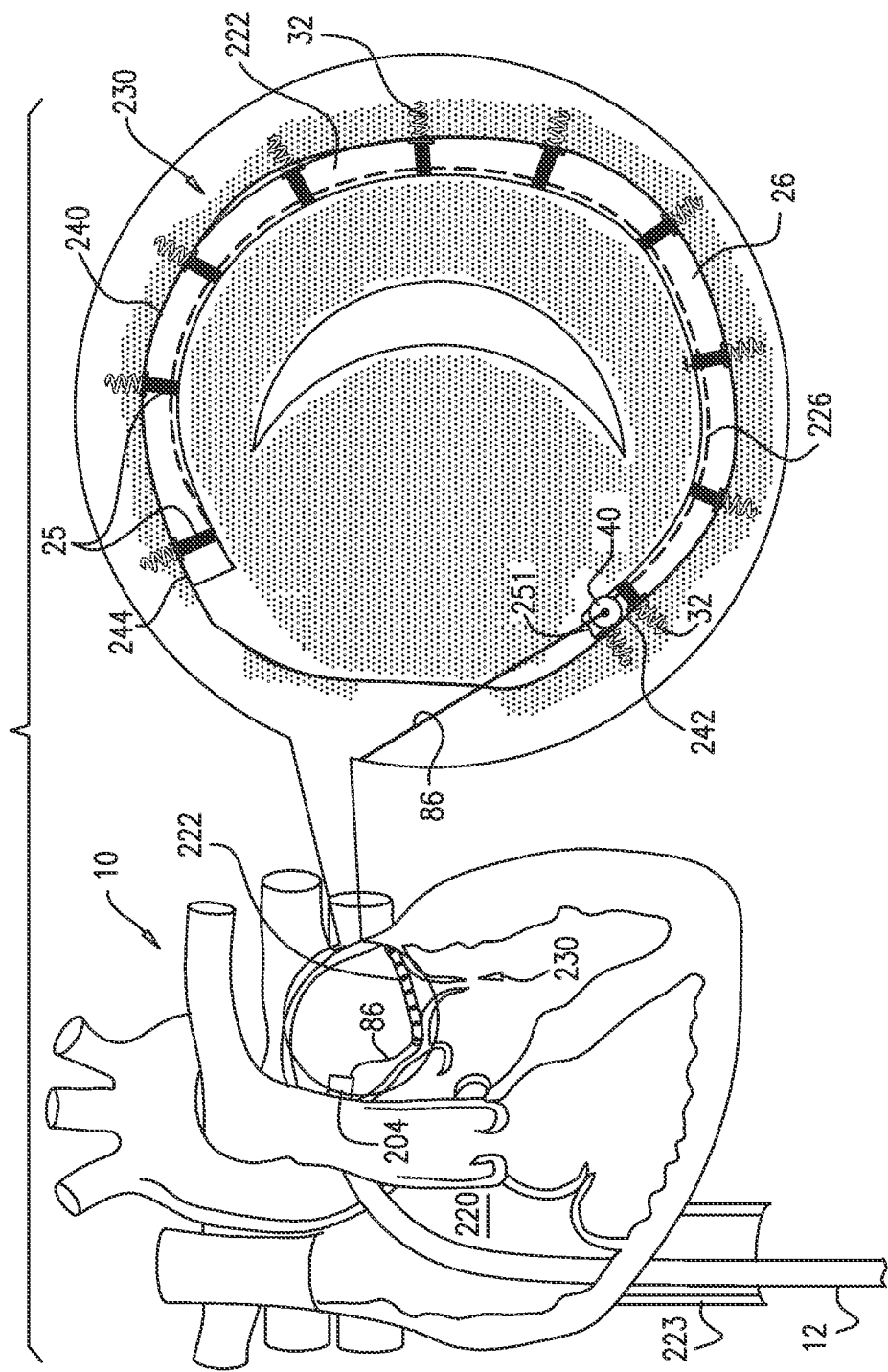

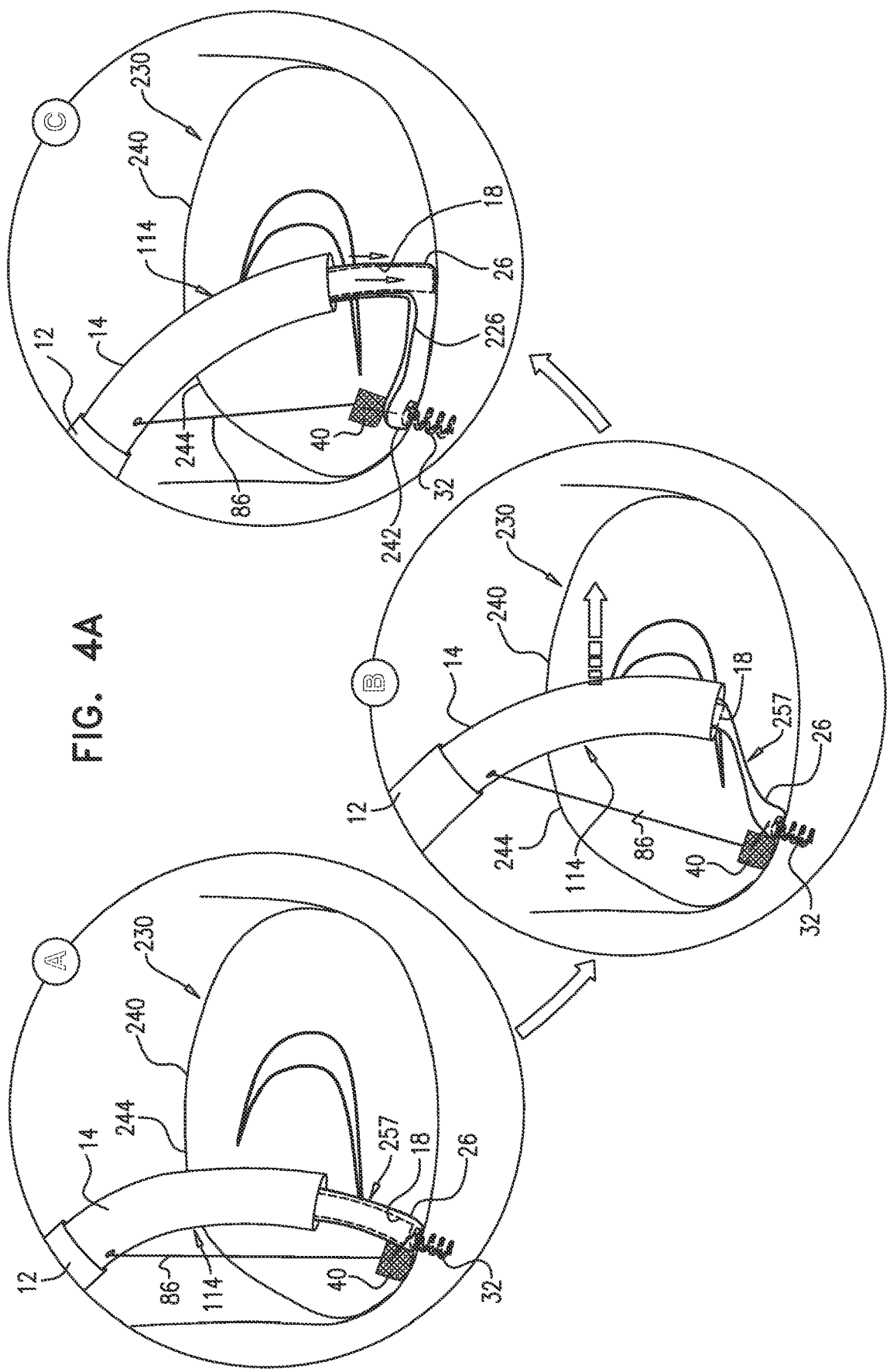

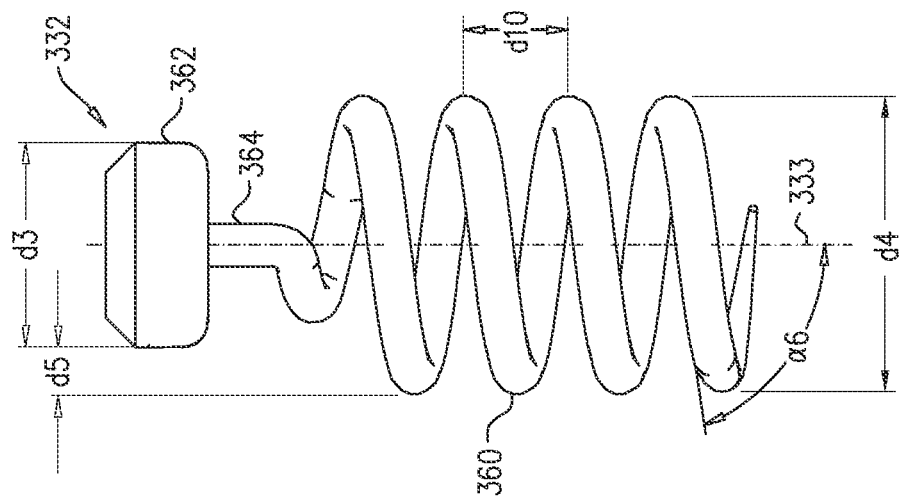
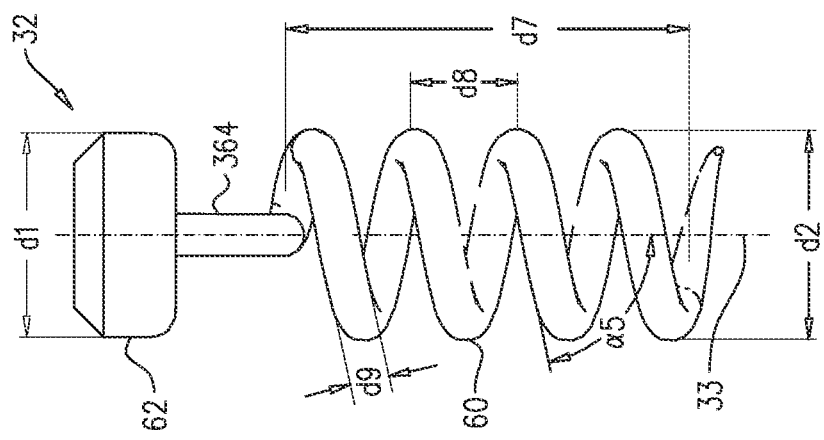

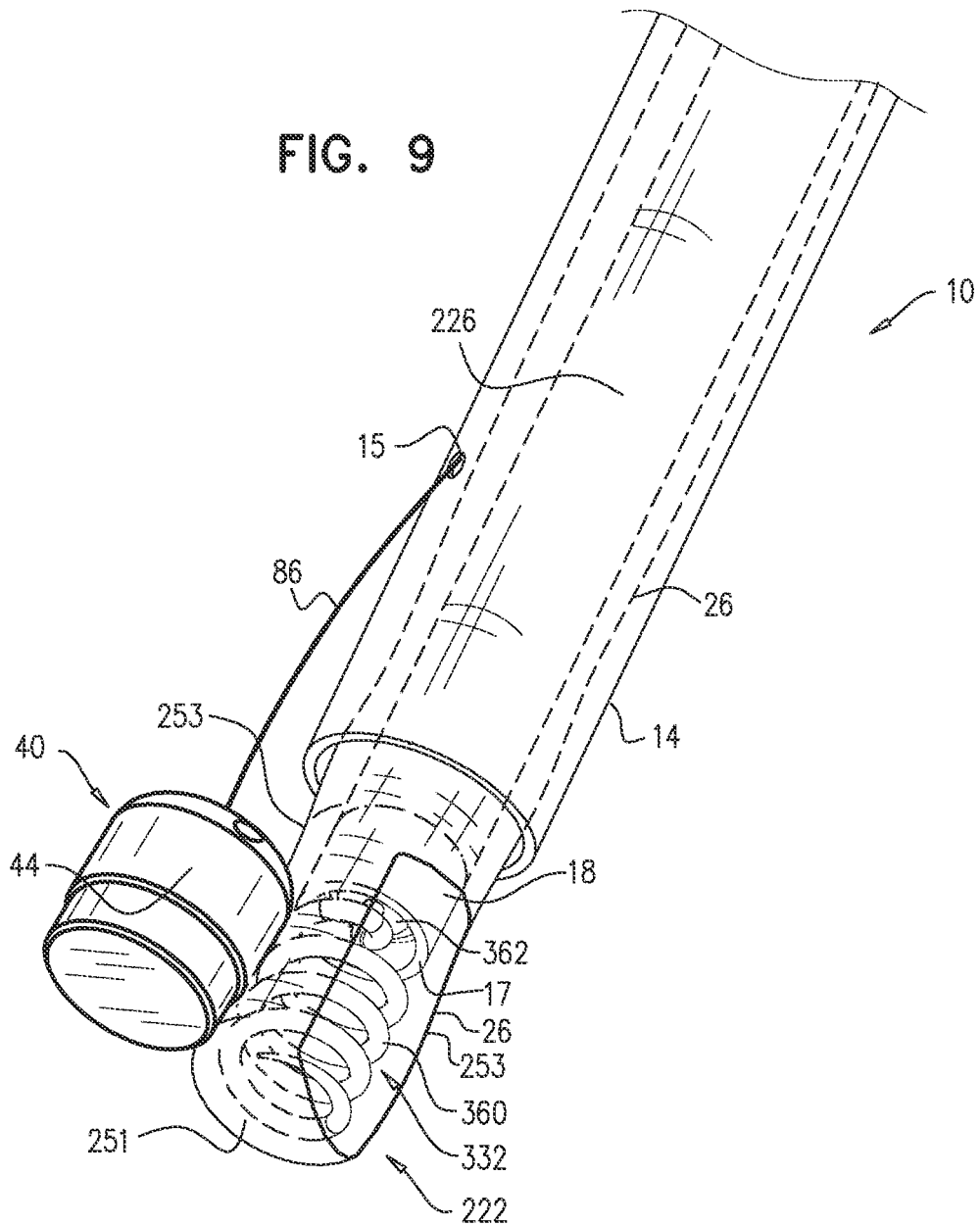

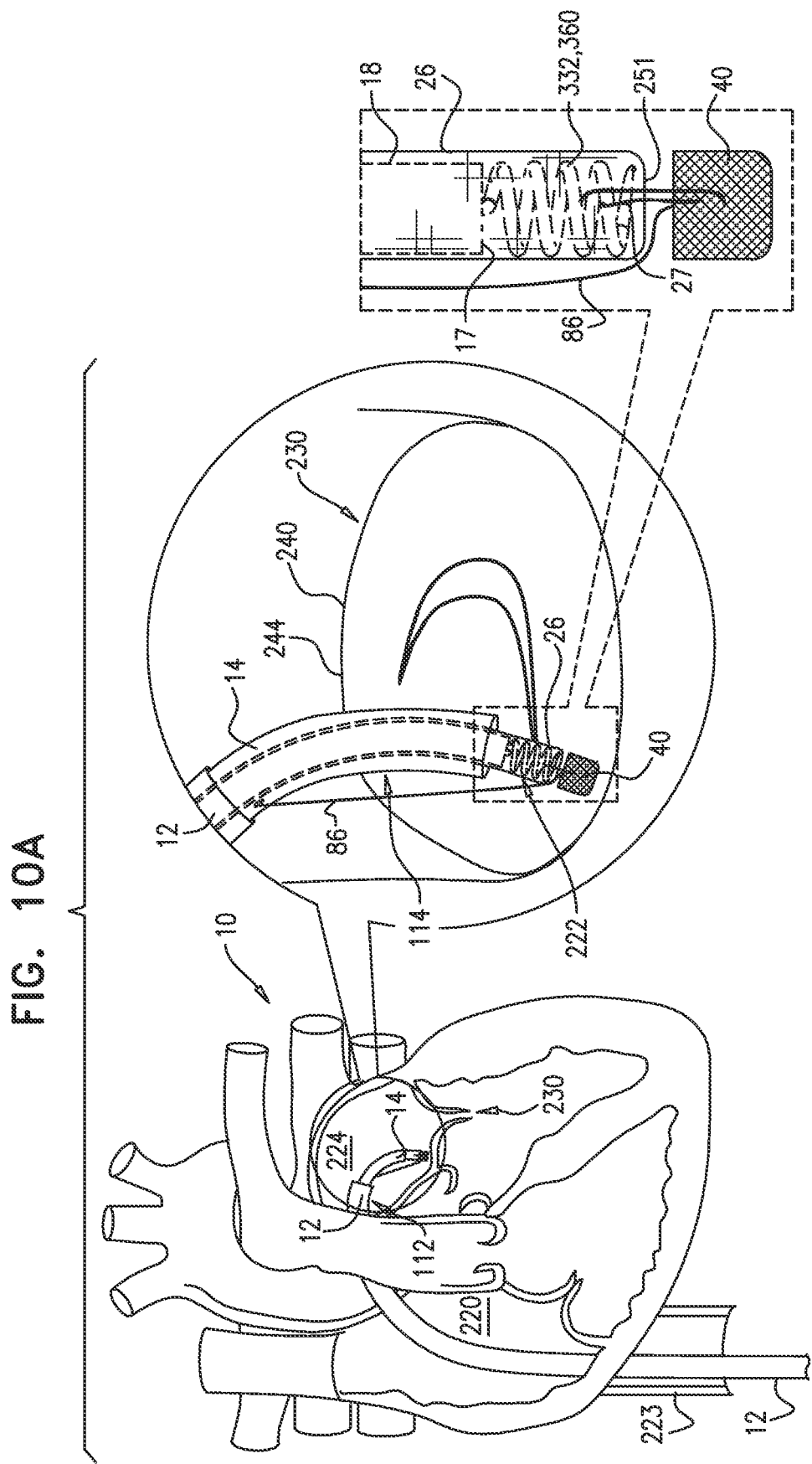

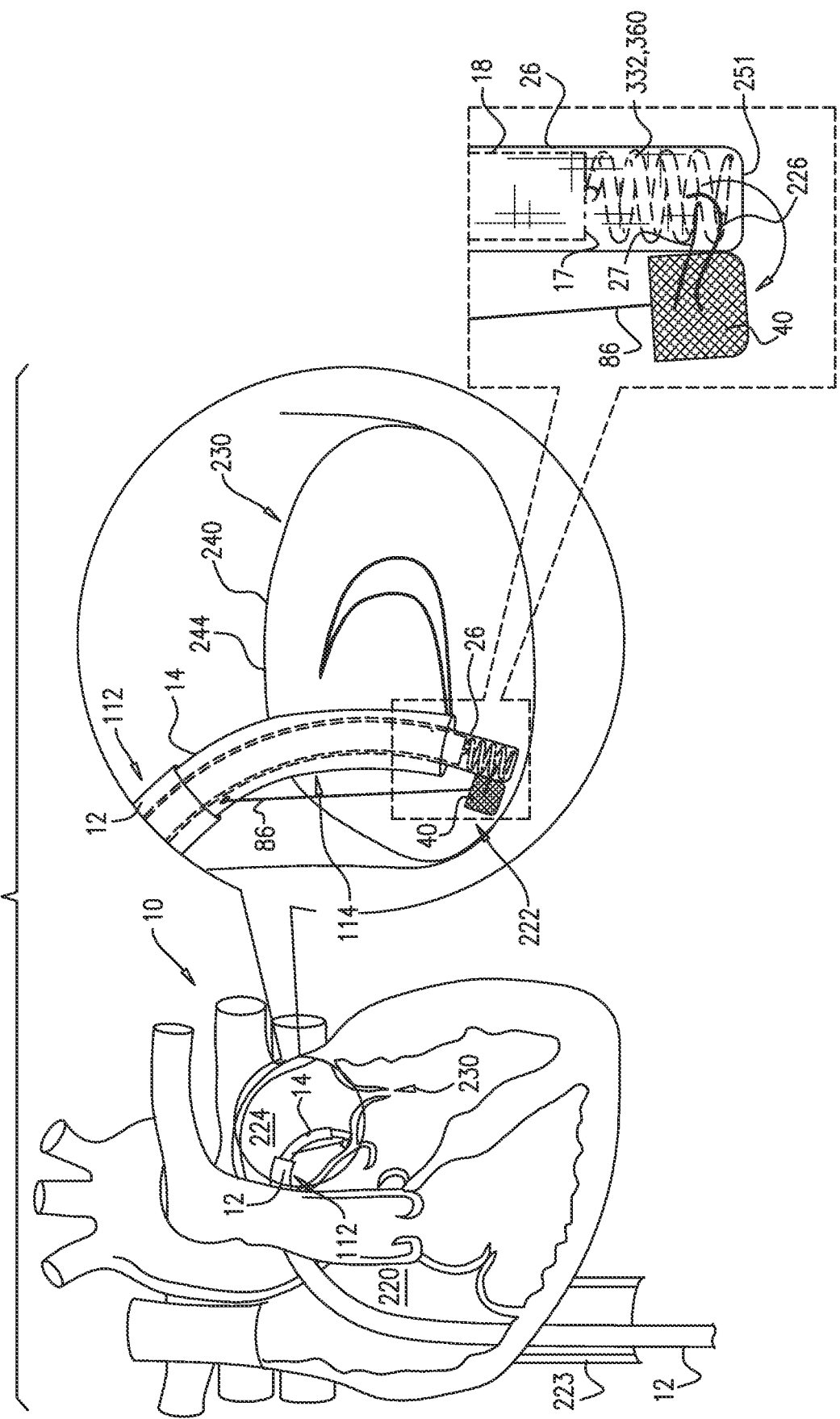

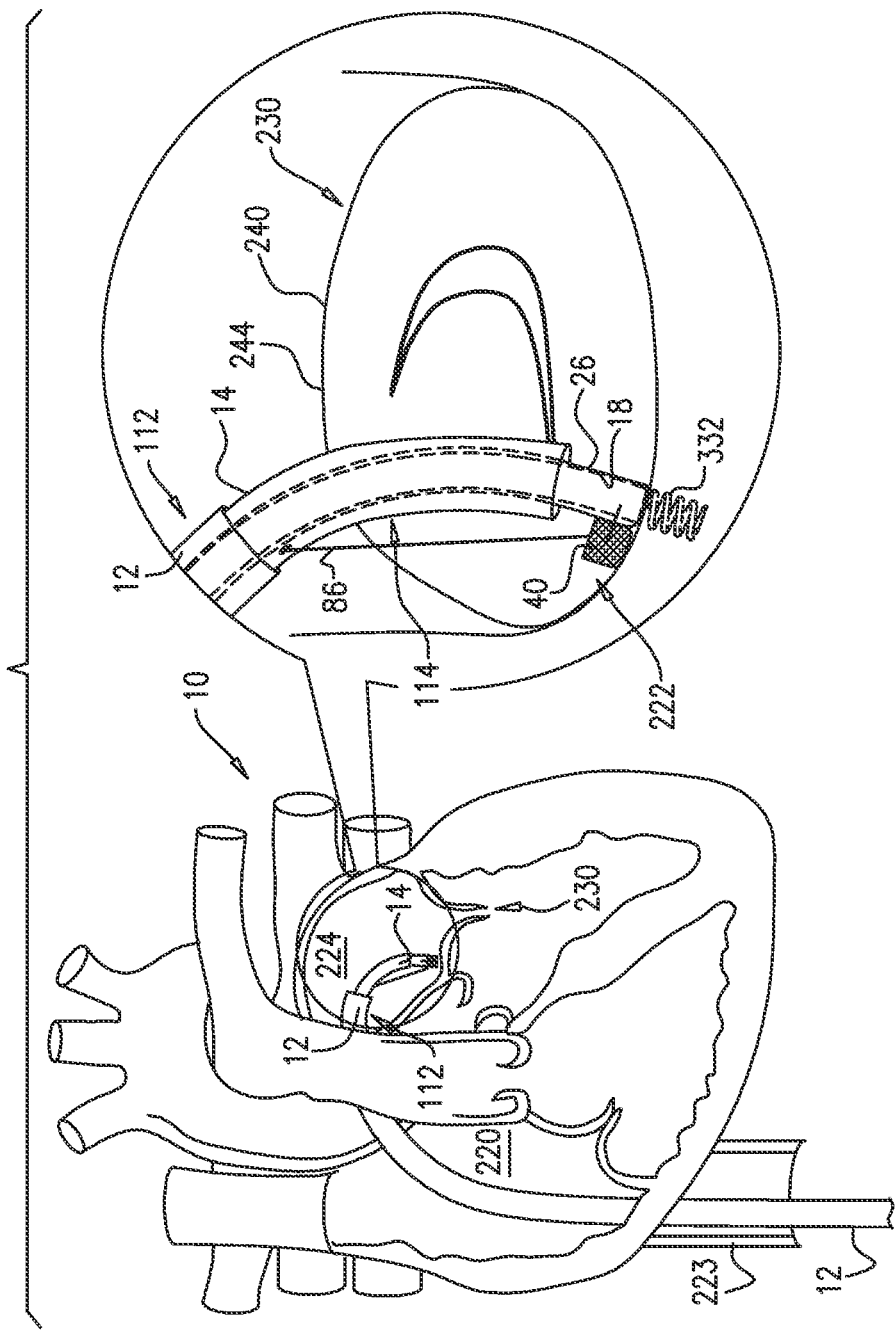

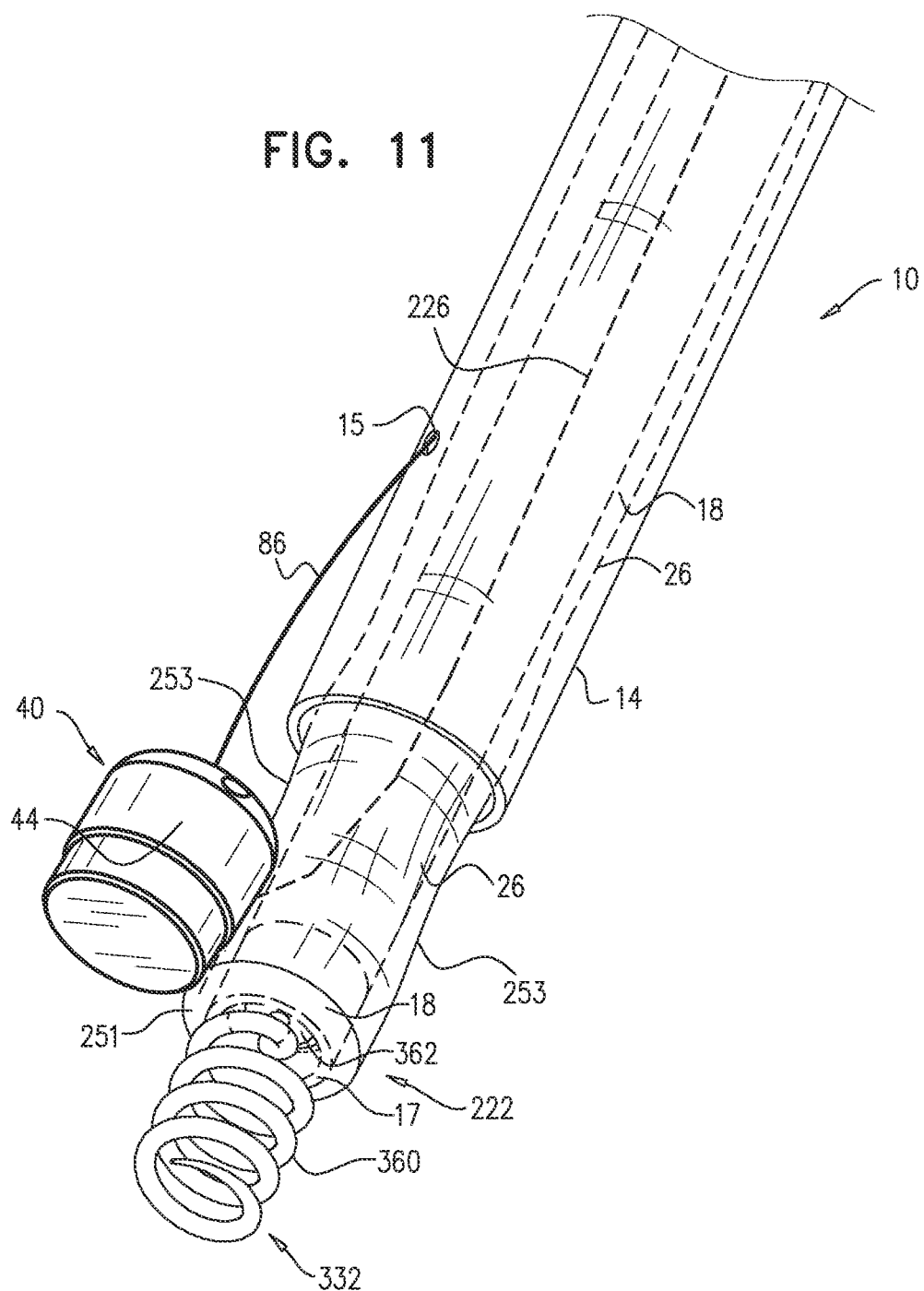

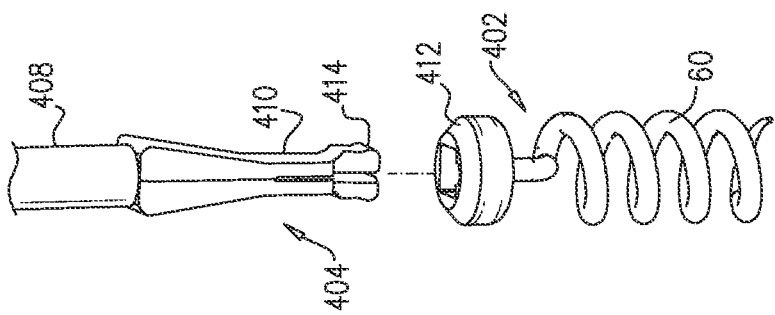
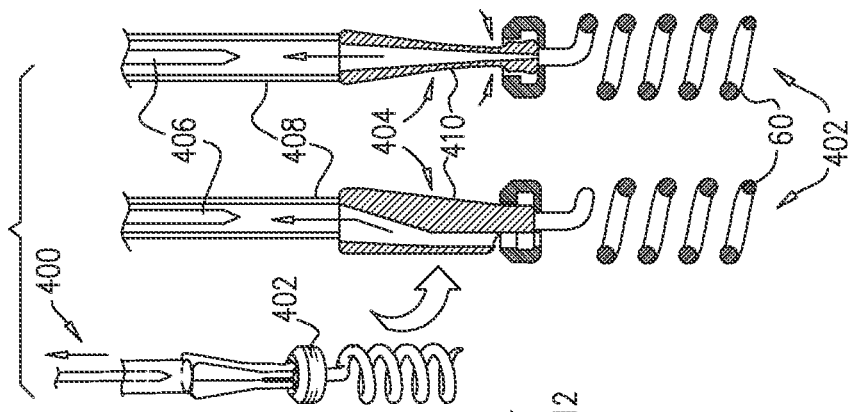
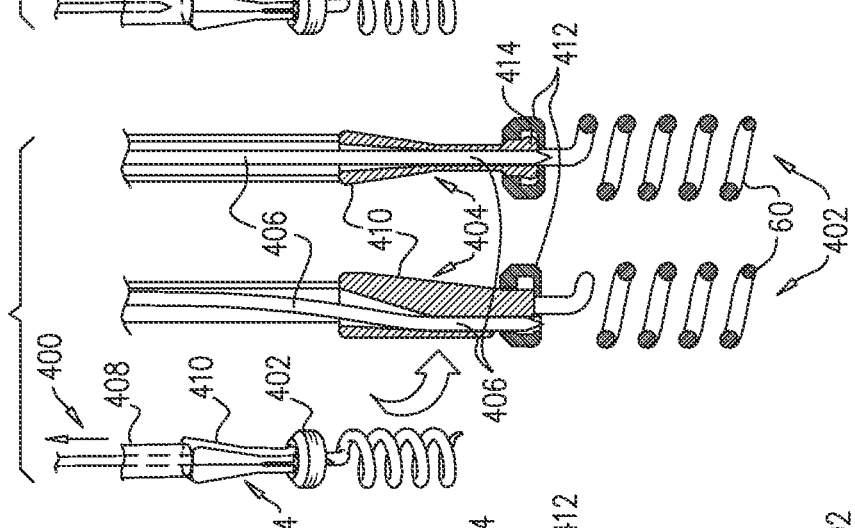
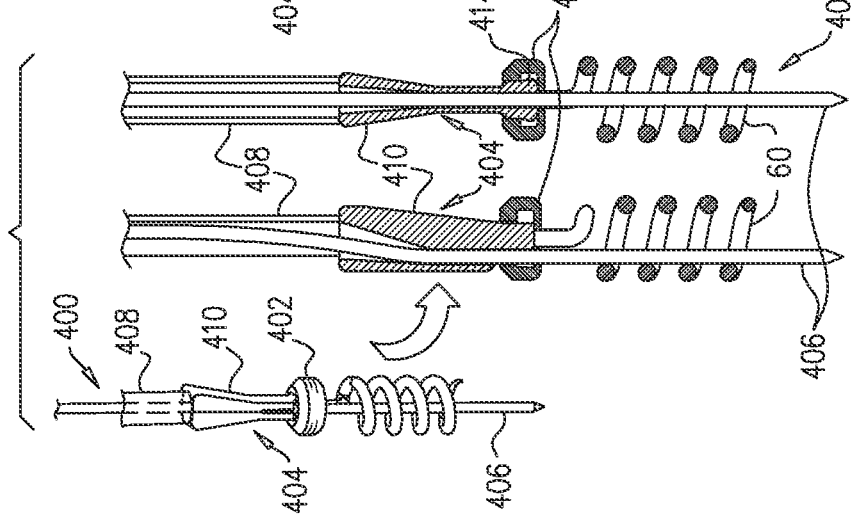

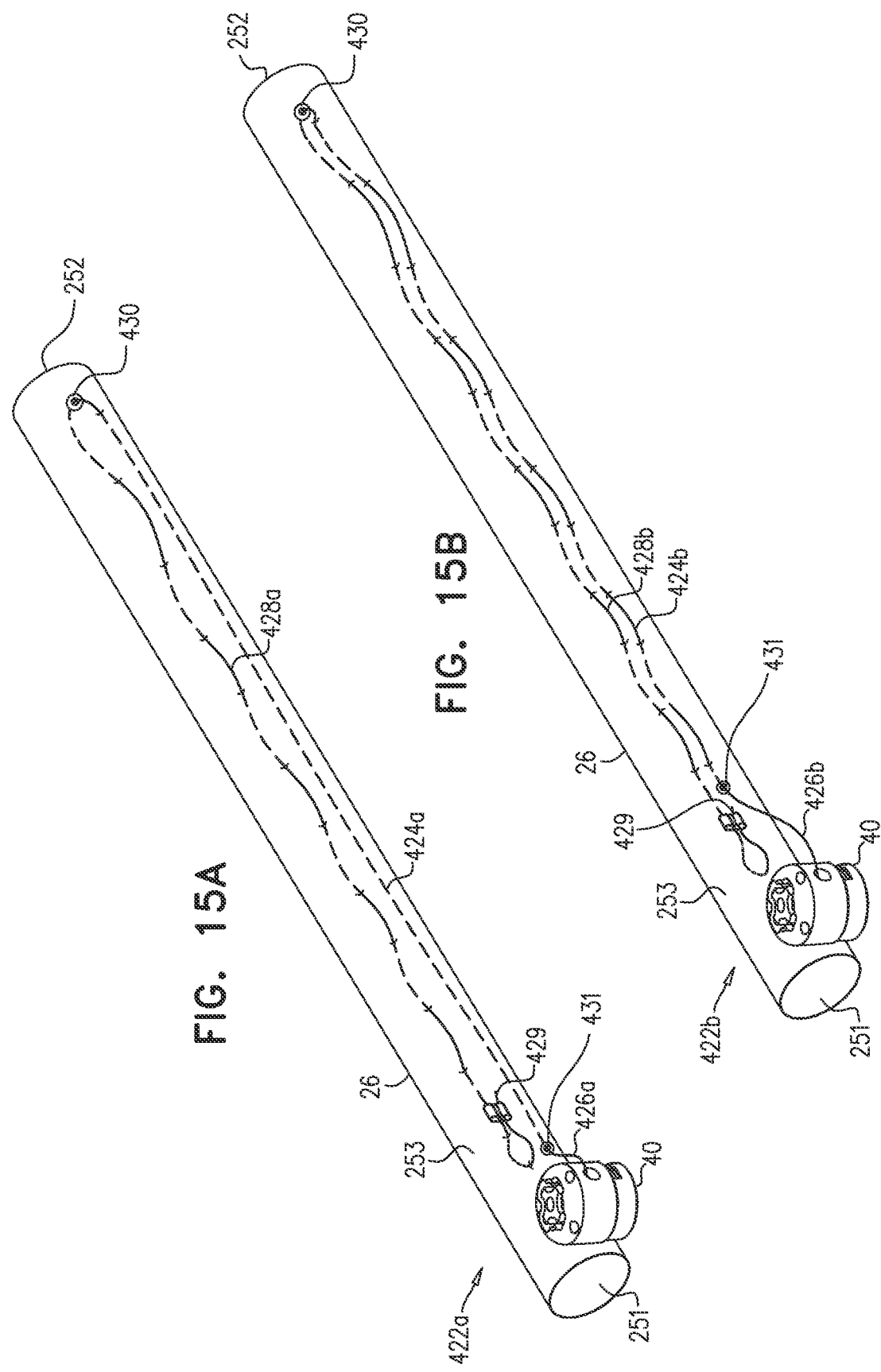

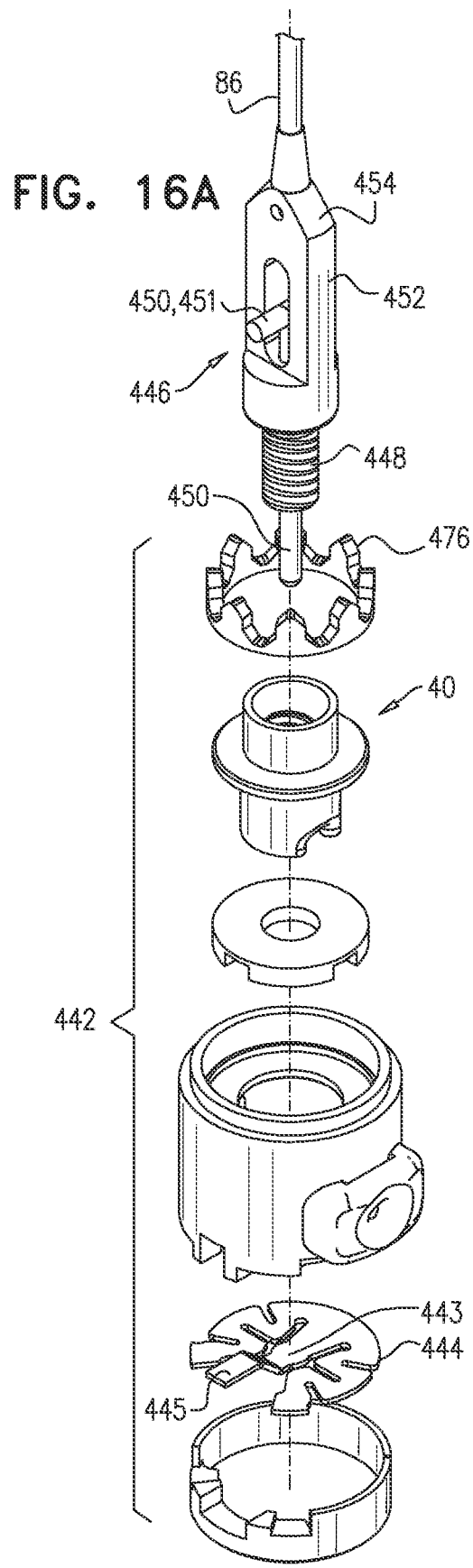
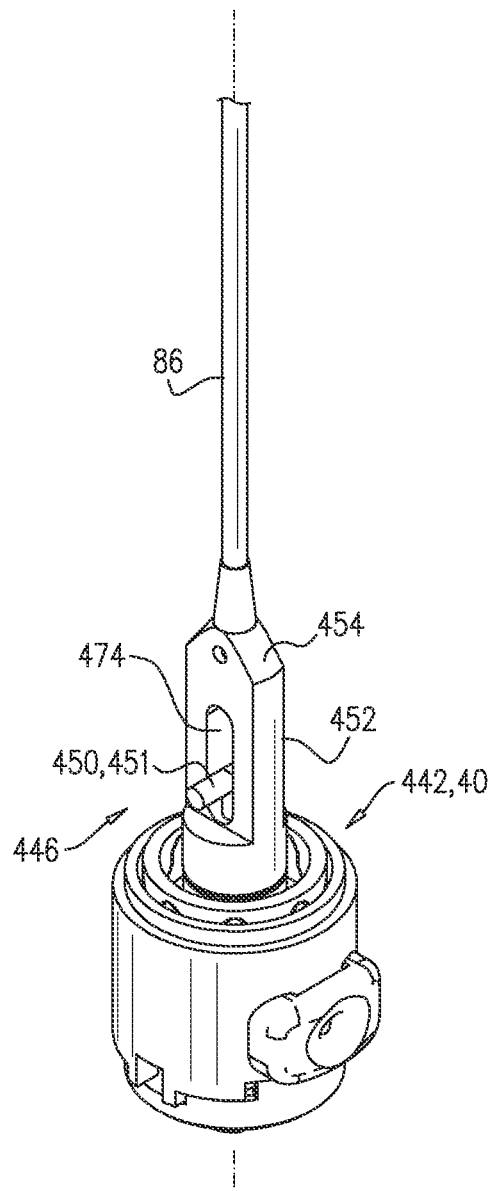

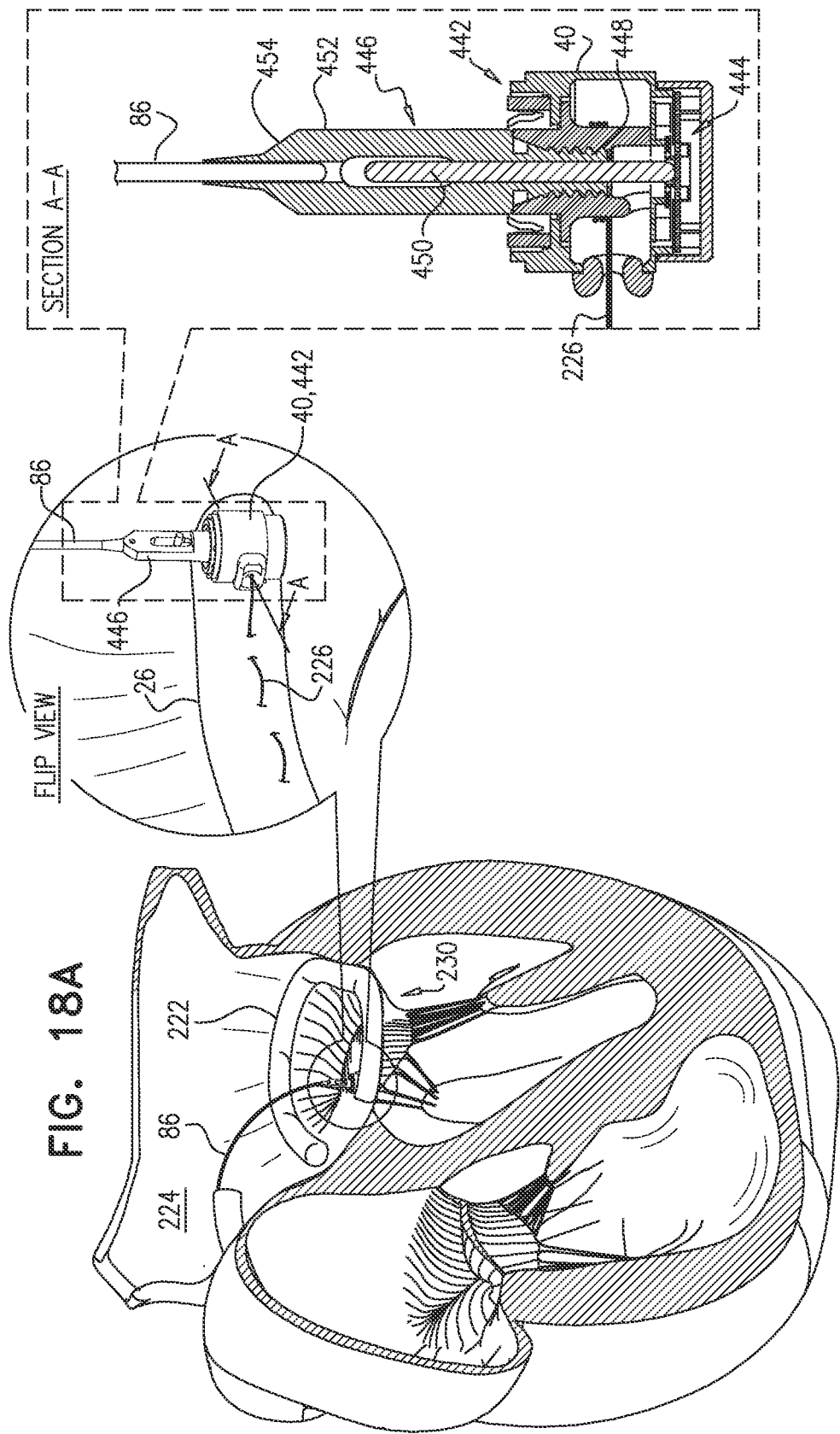

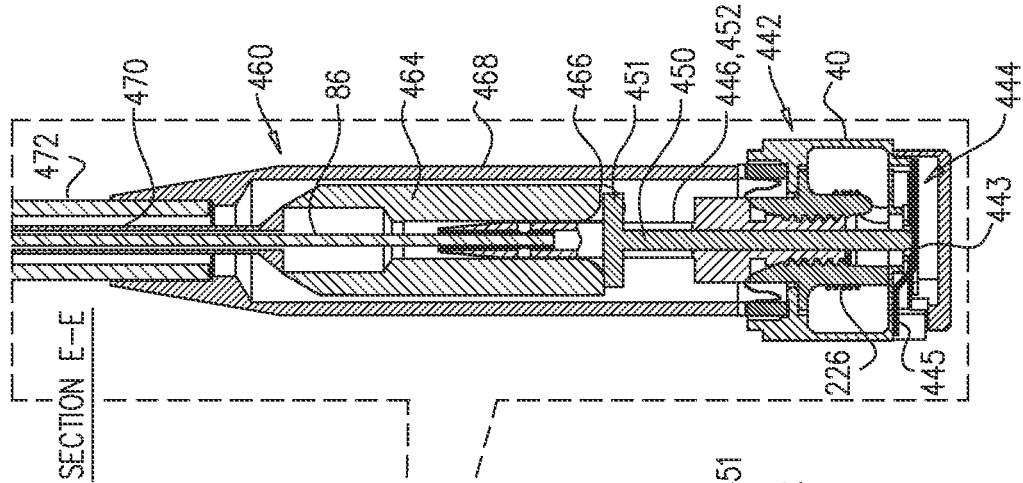
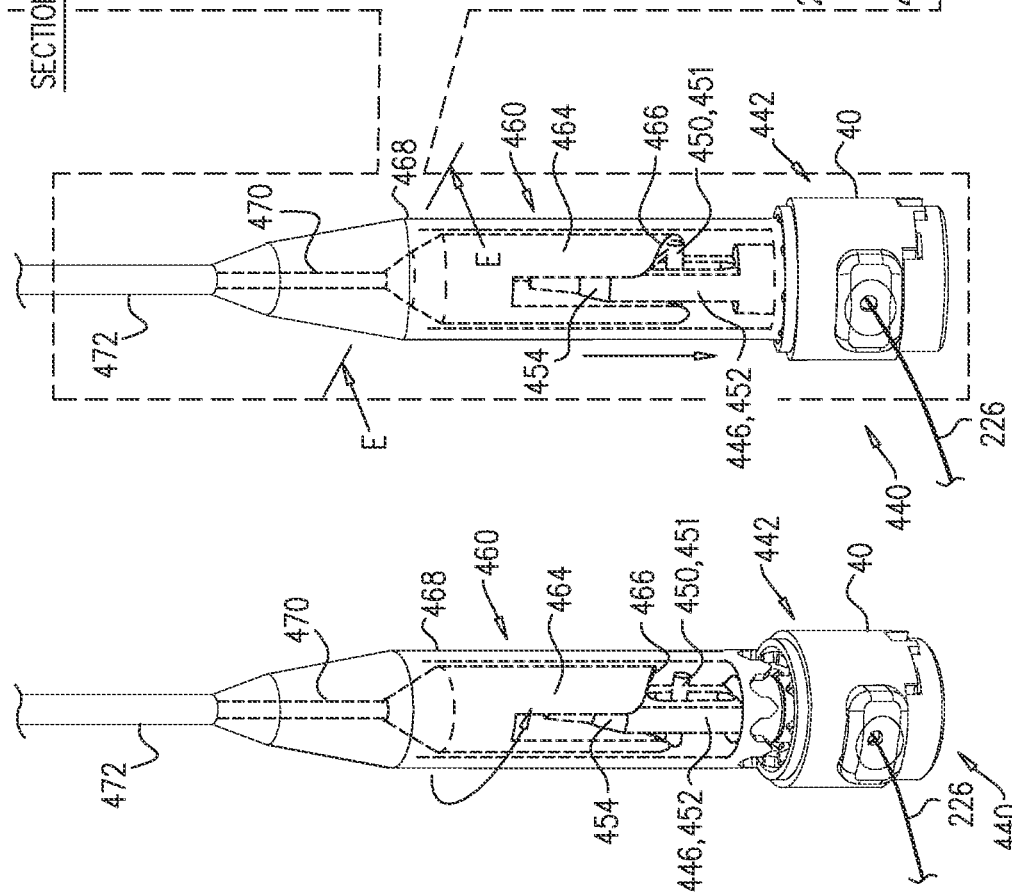
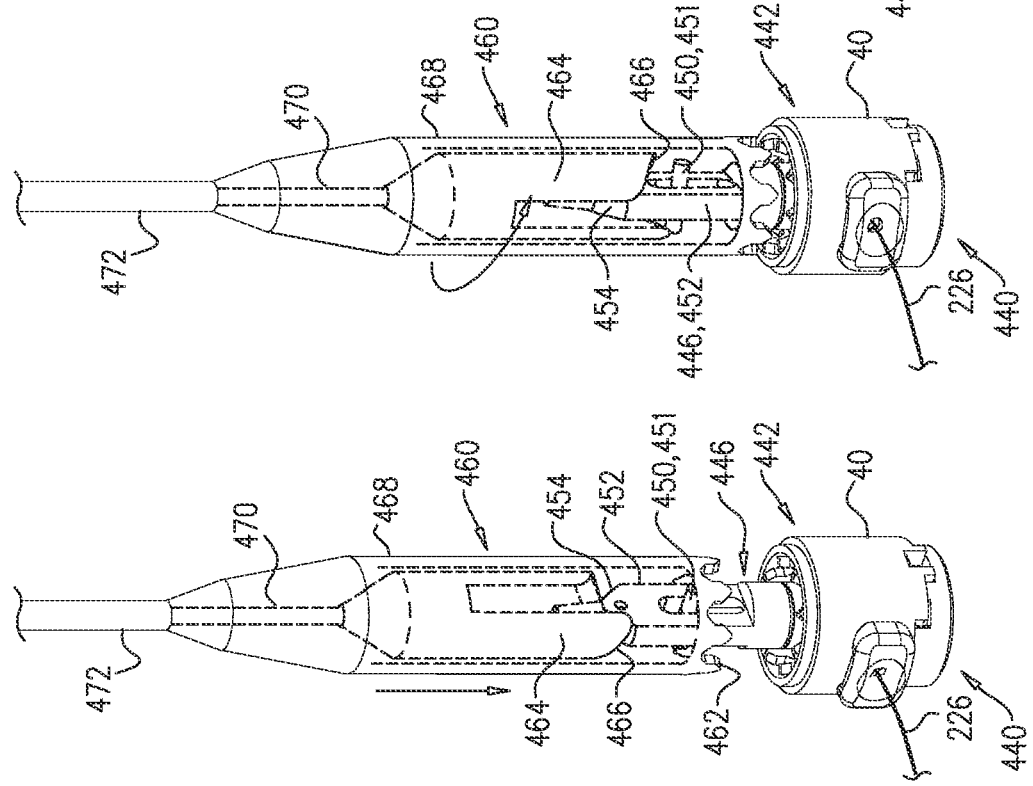

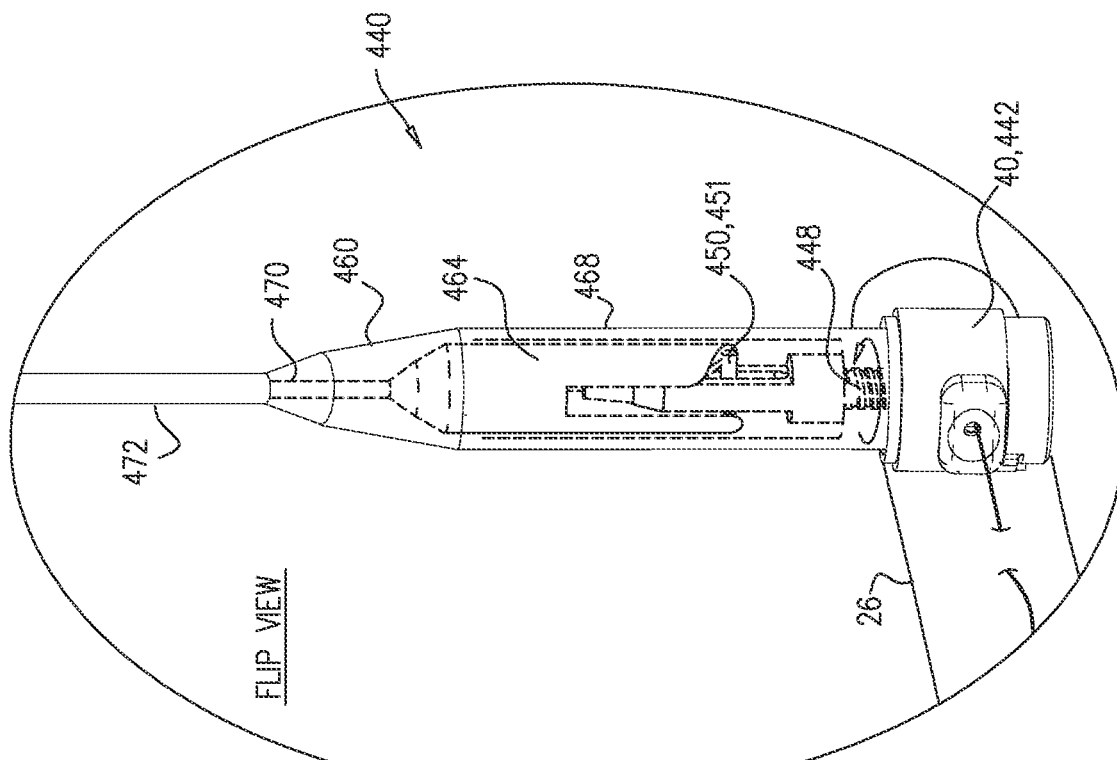
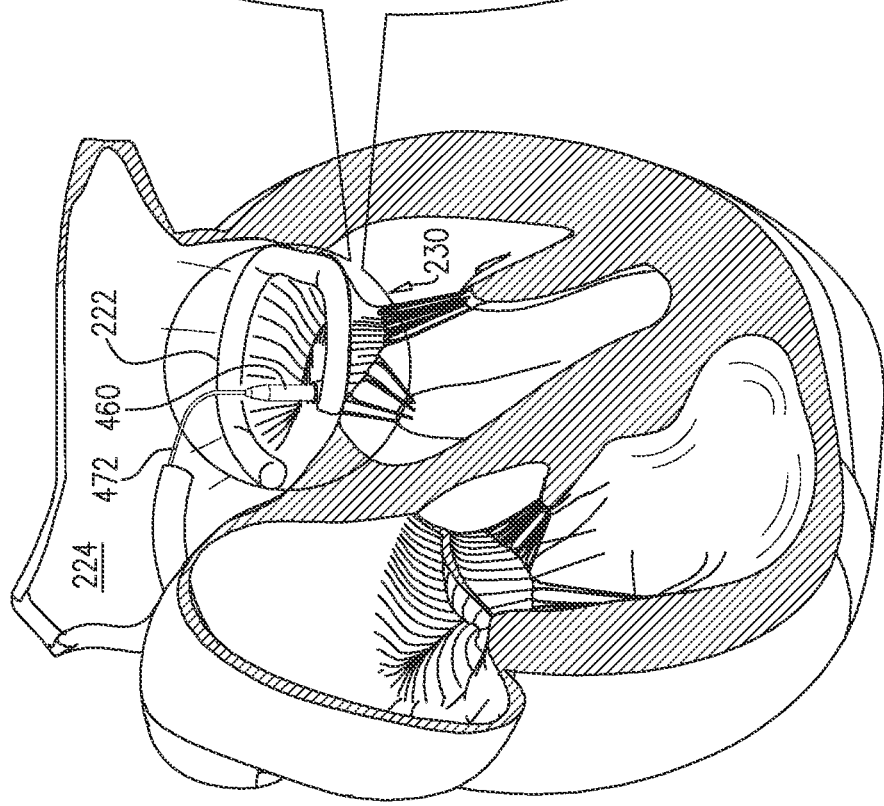
FIG. 18J

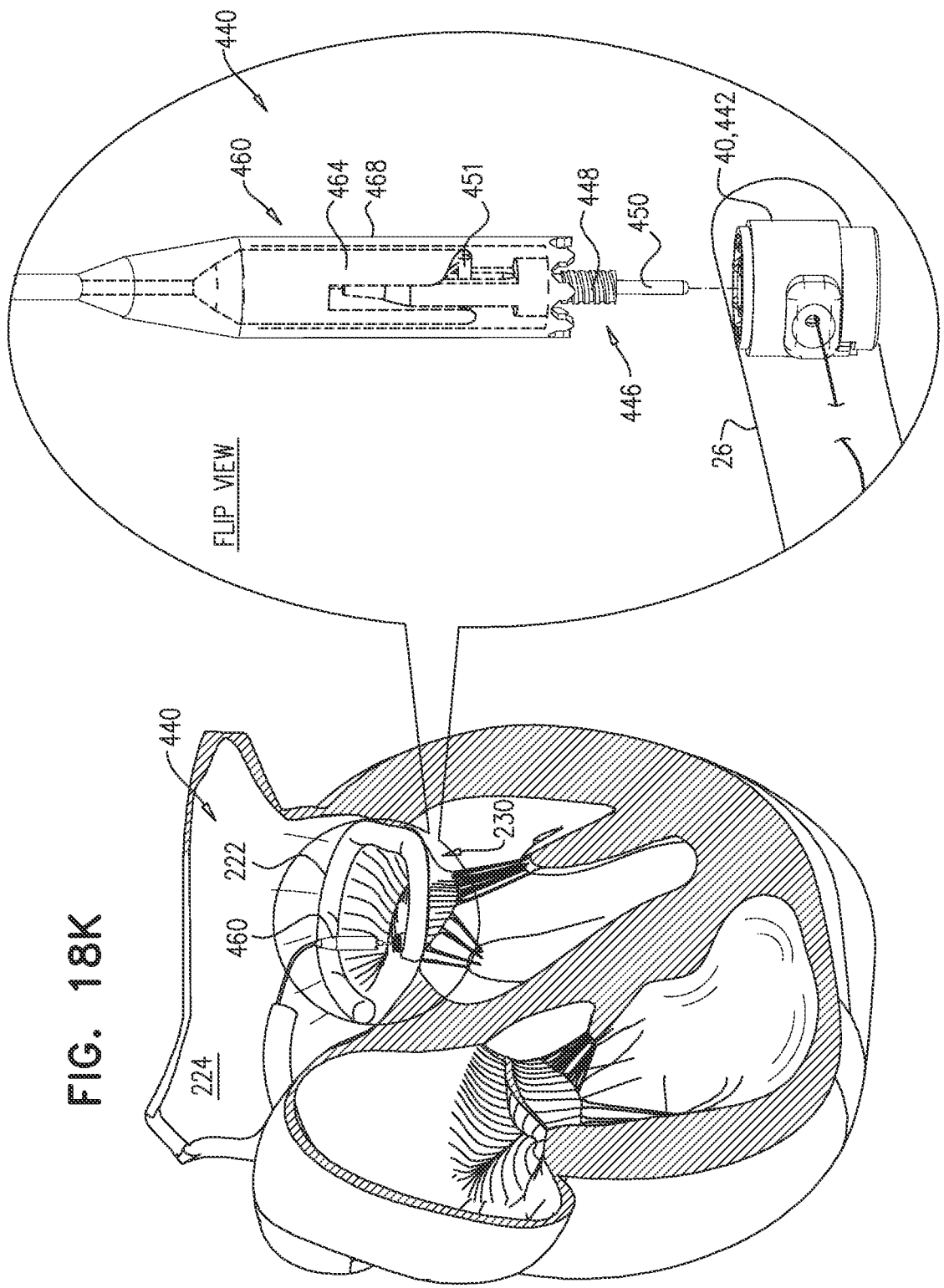

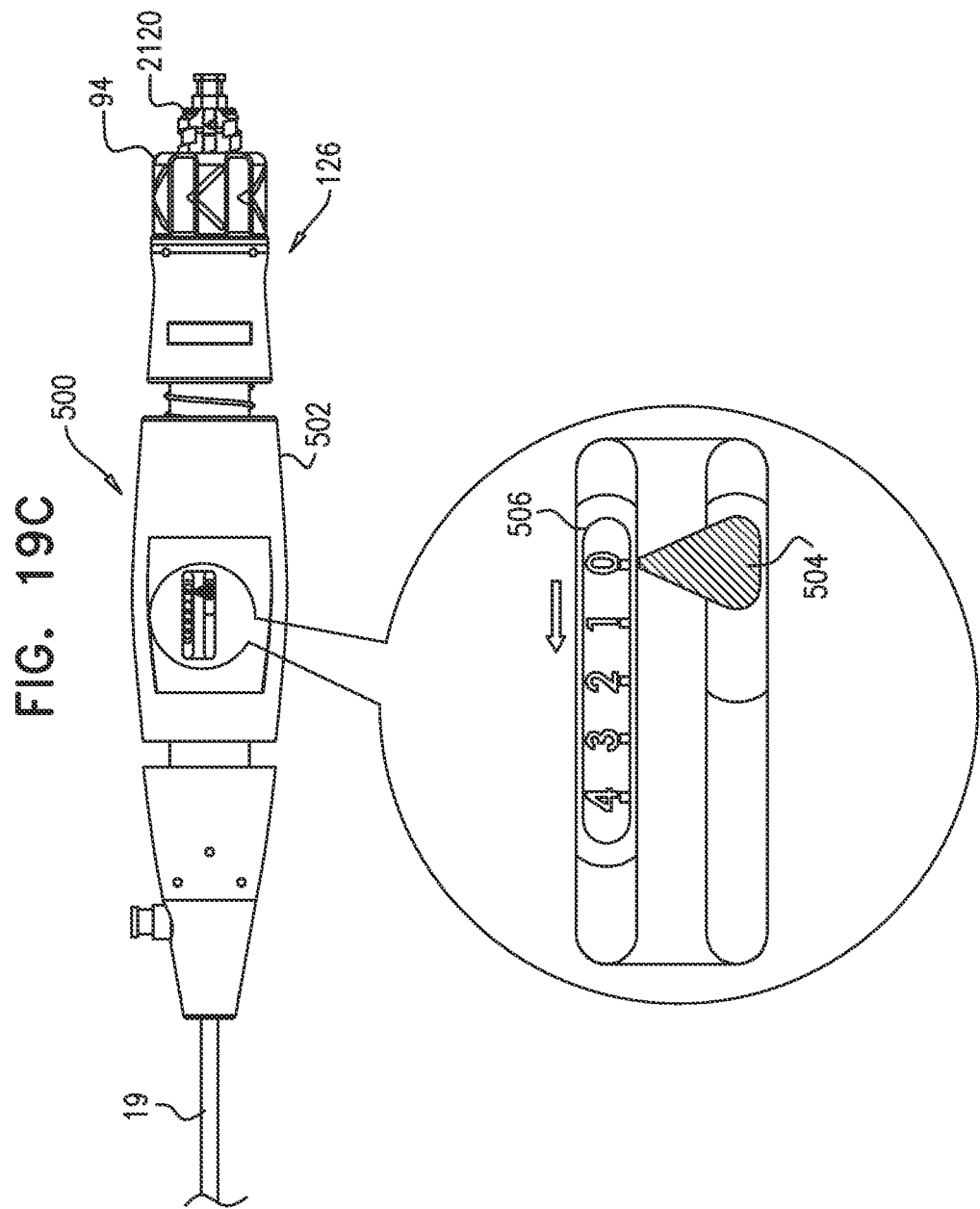

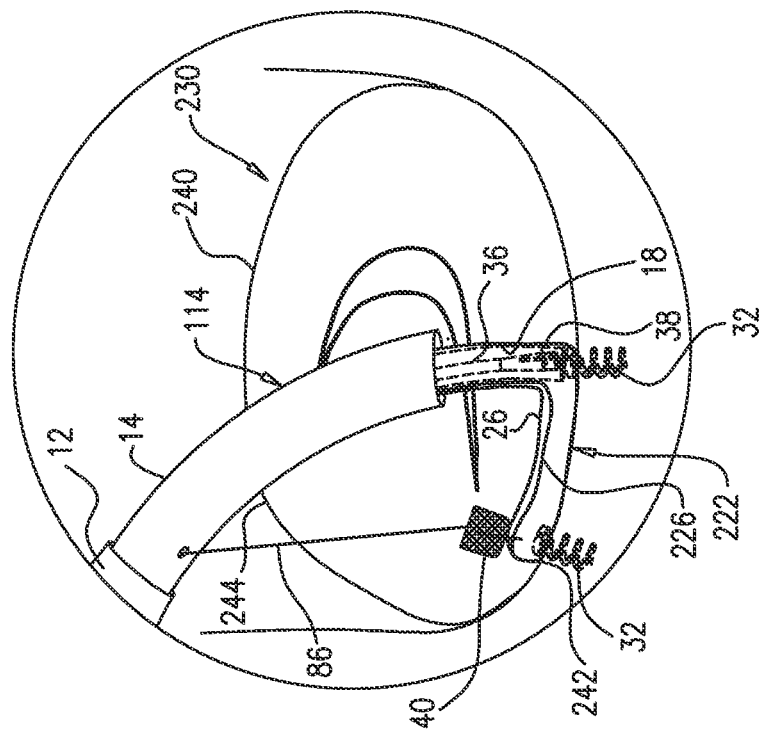
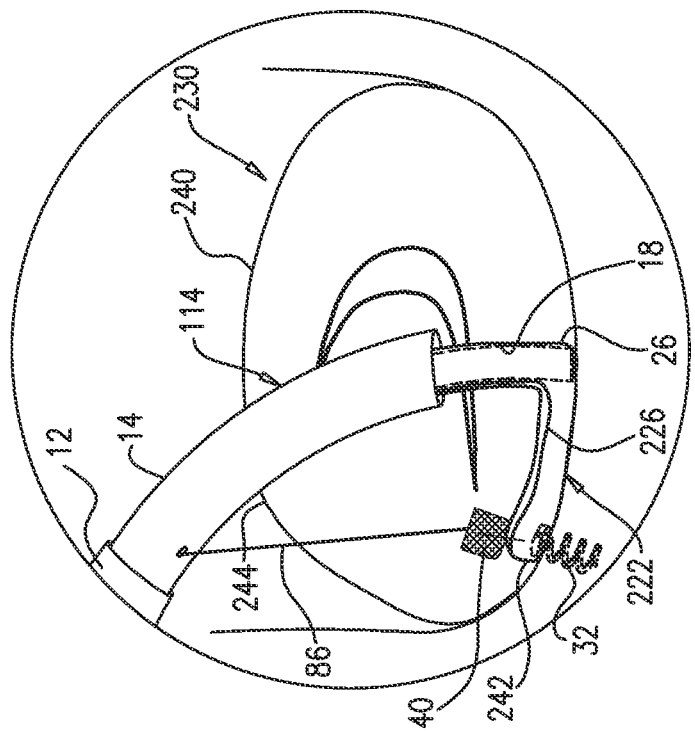

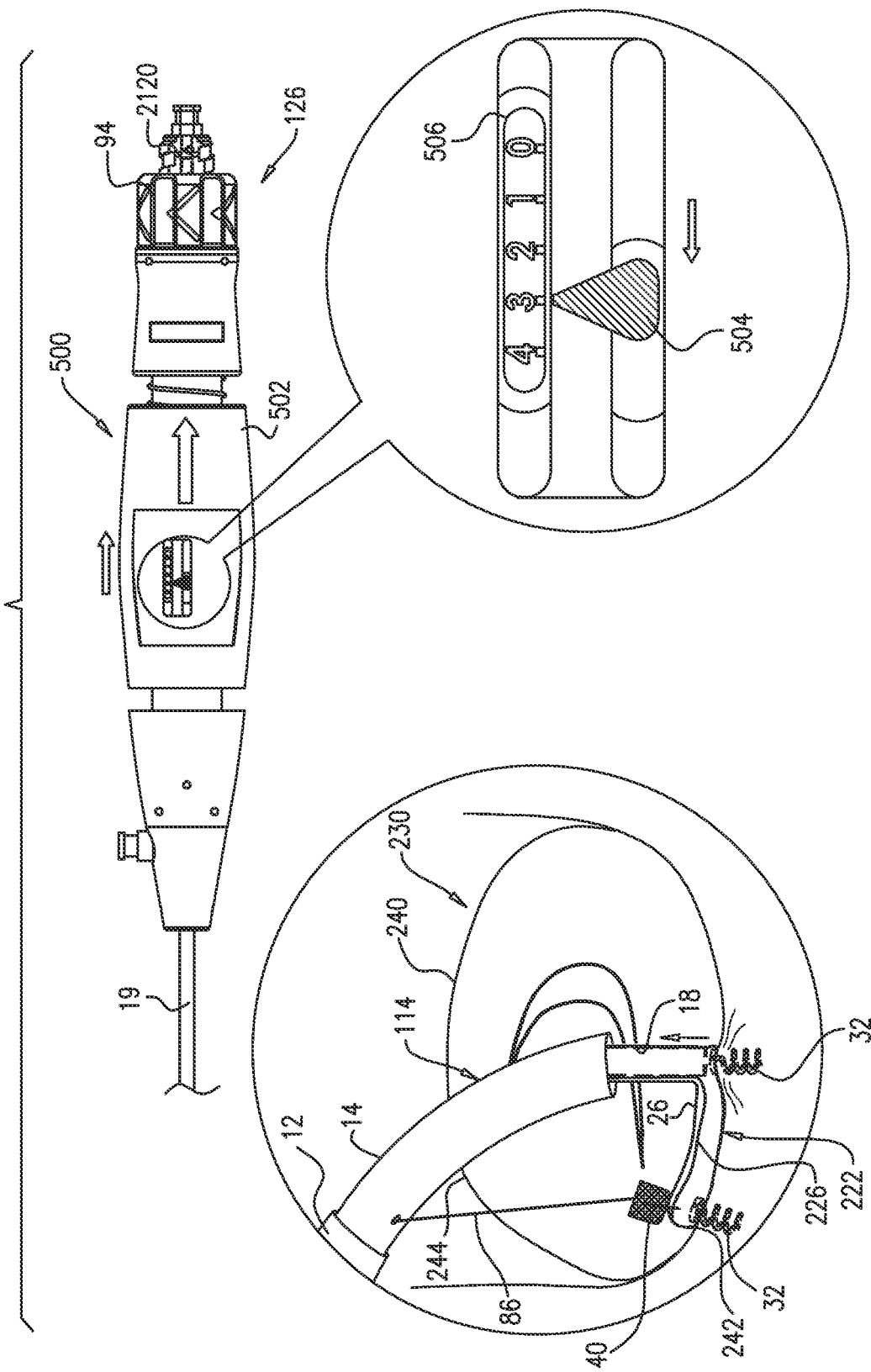

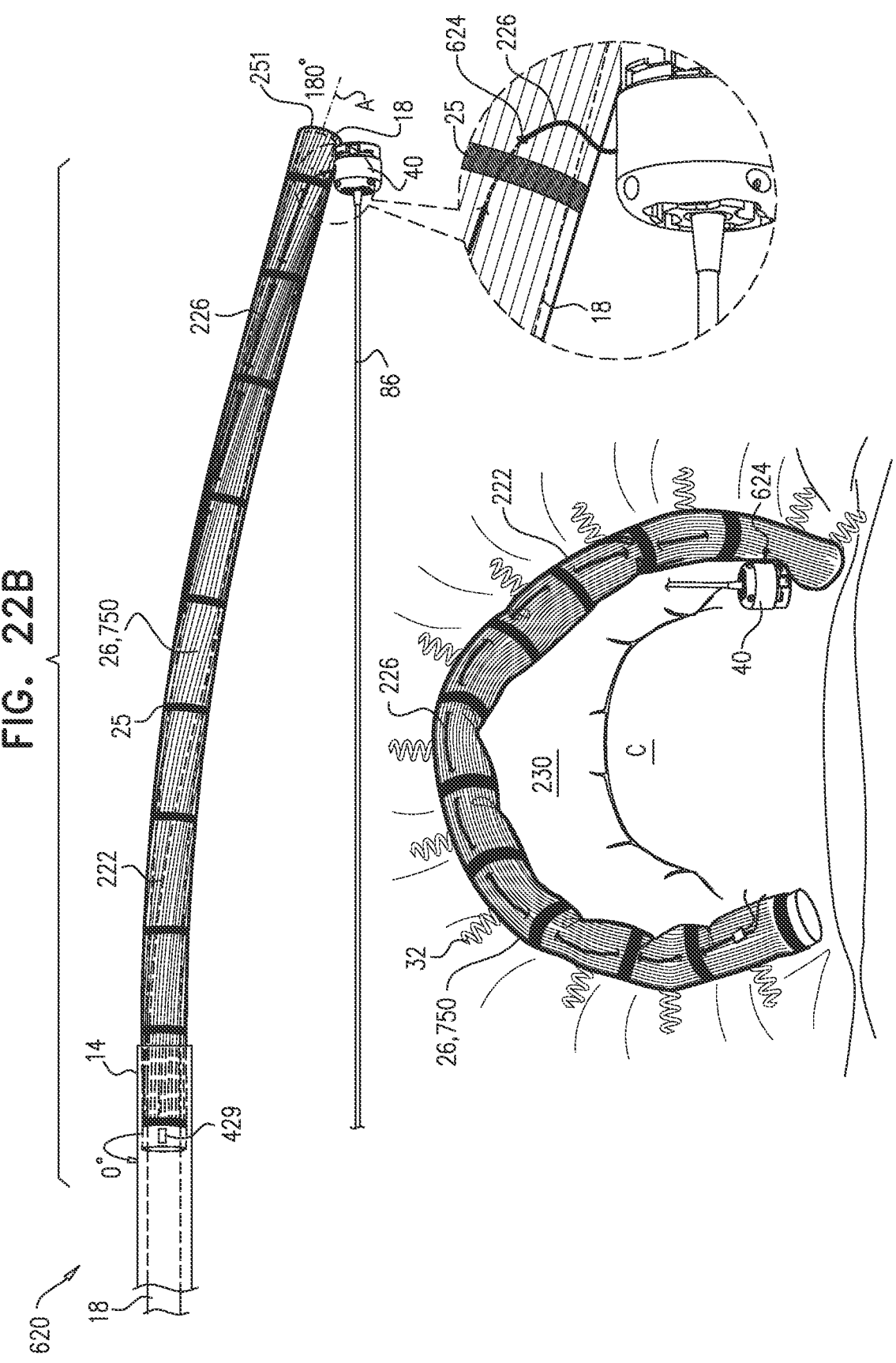

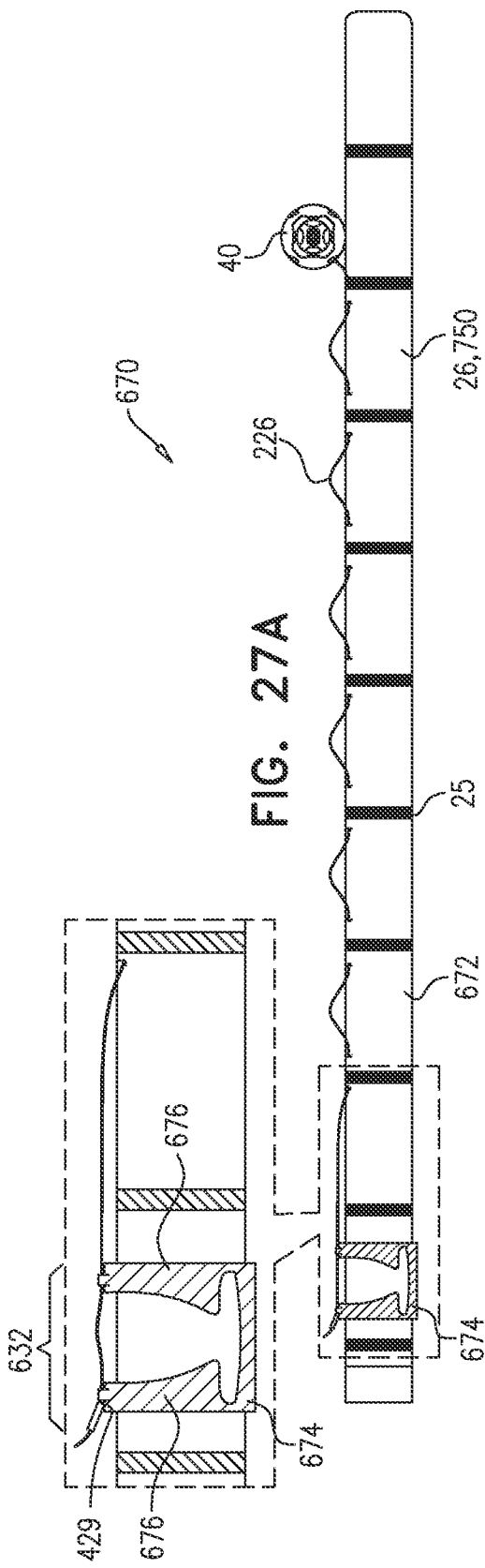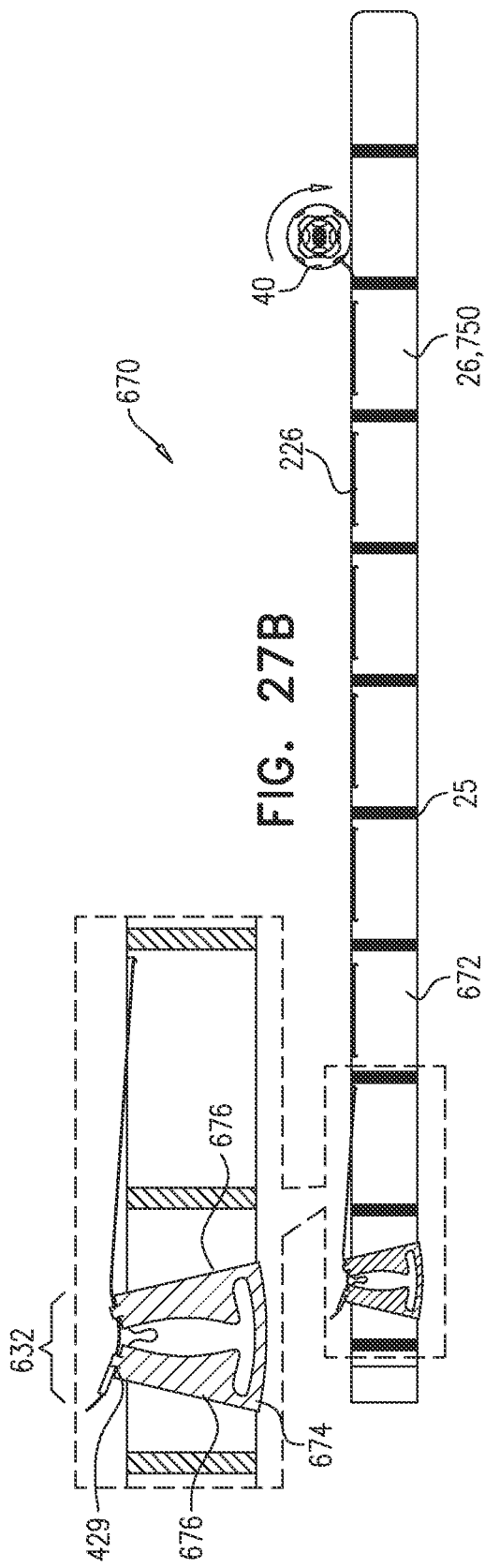

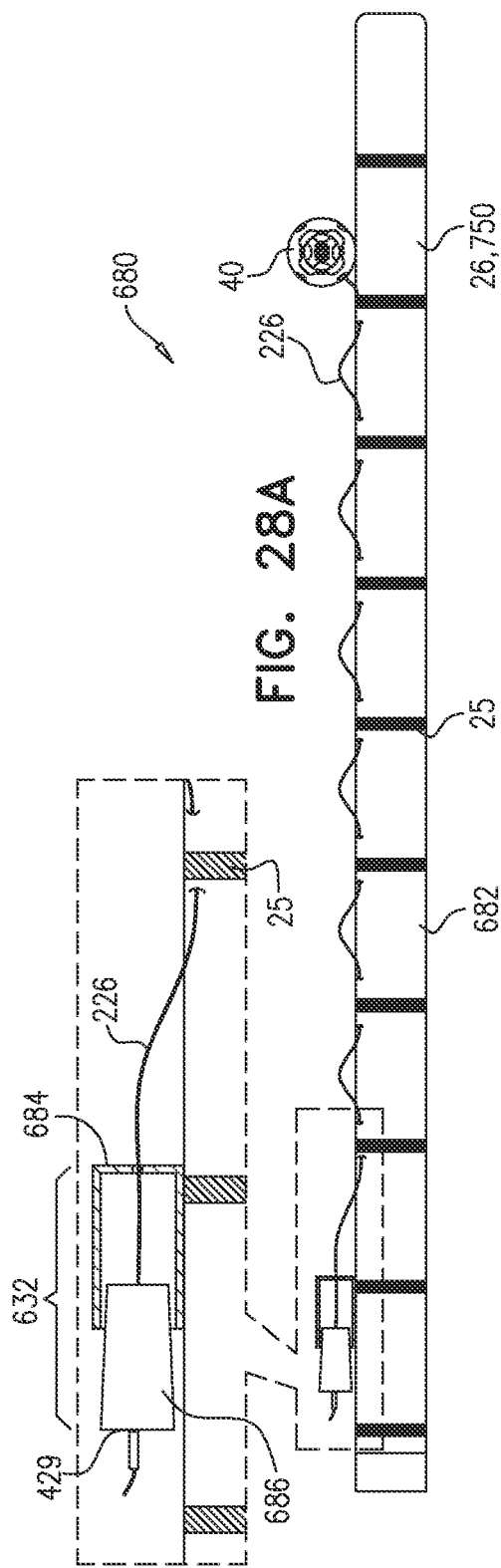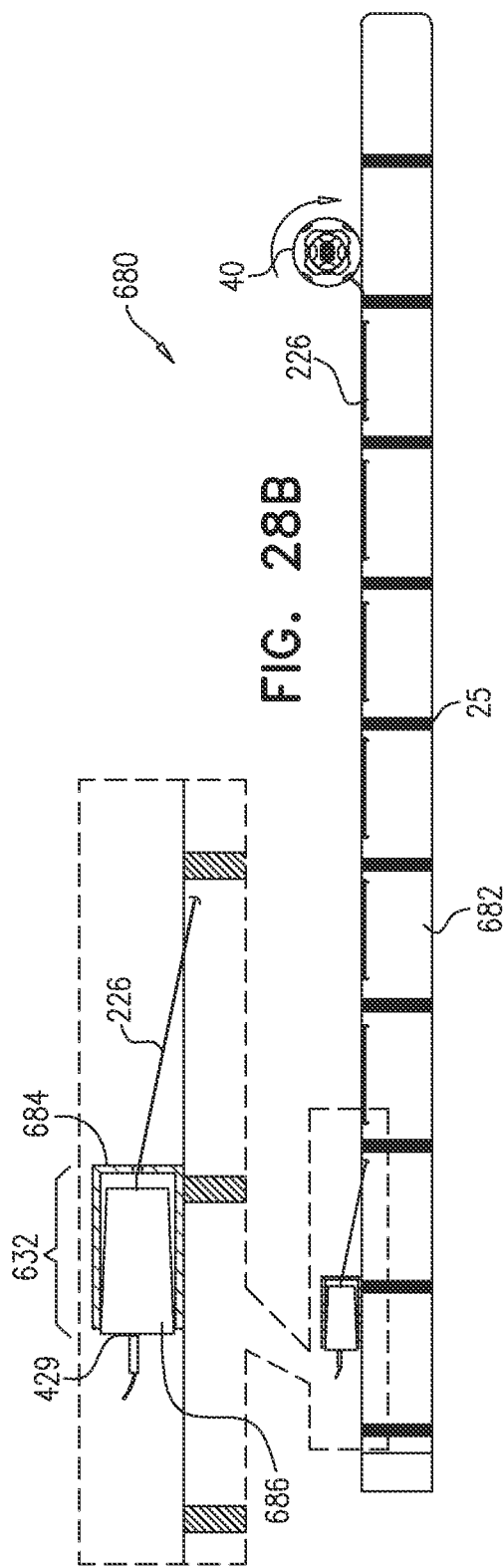

ANNULOPLASTY TECHNOLOGIES

CROSS-REFERENCES TO RELATED APPLICATIONS

The present application is a Continuation of U.S. patent application Ser. No. 16/174,731 to Iflah et al., entitled "Annuloplasty Technologies," filed Oct. 30, 2018 (now U.S. Pat. No. 11,020,227), which is a Continuation of U.S. patent application Ser. No. 15/782,687 to Iflah et al., entitled "Annuloplasty Technologies," filed Oct. 12, 2017 (now U.S. Pat. No. 10,765,514), which is a Continuation of PCT patent application IL2016/050433 to Iflah et al., entitled "Annuloplasty Technologies," filed Apr. 21, 2016, which published as WO 2016/174669, and which claims priority from U.S. Provisional Patent Application No. 62/154,962 to Reich et al., entitled "Annuloplasty Technologies," filed on Apr. 30, 2015, which is incorporated herein by reference.

FIELD OF THE INVENTION

The present invention relates in general to valve repair, and more specifically to repair of an atrioventricular valve of a subject.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

SUMMARY OF THE INVENTION

In some applications of the present invention, a multi-component tubular system is provided for accessing a heart of a subject. The system comprises one or more steerable guiding catheters configured for directing the passage of devices therethrough into the heart. The multi-component tubular system is configured to deliver an implant in a desired orientation to an annulus of a cardiac valve of the subject and to facilitate anchoring of the implant to the annulus. For some applications of the present invention, the guiding system is advanced transluminally or transthoracically accessing an atrium of the heart. Typically, the system comprises two or more steerable catheters. A first catheter has a distal portion that is steerable to a first desired spatial orientation. A second catheter is disposed within the first catheter and has a distal portion that is steerable to a second desired spatial orientation. The system provides techniques and relative-spatial-orientation-controlling devices for controlling the orientation of the distal portion of the second catheter with respect to the first catheter without substantially distorting the first spatial orientation of the distal portion of the first catheter.

For some applications, an implant is advanced via the multi-component catheter system, and is anchored to tissue of the subject by driving one or more tissue anchors through a channel using an anchor driver. For some applications, the anchor driver is used to provide a reference force to a recently-anchored anchor, while the implant is further exposed from the catheter system. For some applications, a first tissue anchor has a tissue-coupling element that is wider than the tissue-coupling element of subsequent anchors, and is wider than the channel. For some applications, a lance is used to control anchoring of the tissue anchors.

For some applications, the implant has a contraction member that extends from an adjustment mechanism, along the implant, and back again.

For some applications, a system is provided for repeatedly docking with and adjusting an adjustment mechanism of the implant.

For some applications, the multi-component catheter system comprises a force gauge for testing the anchoring strength of individual anchors subsequent to their anchoring.

Other embodiments are also described.

There is therefore provided, in accordance with an application of the present invention, apparatus, for use with a tissue of a subject, the apparatus including:
  an anchor, including:
    an anchor head, and
    a tissue-engaging member, coupled to the anchor head, extending distally away from the anchor head until a distal tip of the tissue-engaging member, and configured to anchor the anchor to the tissue;
  an anchor driver, including:
    a longitudinal shaft, having a flexible distal portion and a distal end,
    a deployment element at the distal end of the shaft, reversibly lockable to the anchor head, and reversibly movable between (i) a locked state that retains locking between the deployment element and the anchor head, and (ii) an unlocked state that unlocks the deployment element from the anchor head, and
    a tissue-piercing lance, reversibly movable between:
      an extended state in which (i) the lance extends distally from the shaft, (ii) while the deployment element is locked to the anchor head, the lance extends distally past the distal tip of the anchor, and (iii) the lance retains the deployment element in the locked state, and
      a retracted state in which the deployment element automatically moves into the unlocked state.

In an application, in the retracted state, the lance does not extend distally past the distal tip of the anchor.

In an application, in the retracted state, the lance does not extend distally from the shaft.

There is further provided, in accordance with an application of the present invention, apparatus, for use with a tissue of a subject, the apparatus including:
  a percutaneous catheter;
  an implant, dimensioned to be advanced into the subject via the catheter;
  an anchor-delivery channel, shaped to define a lumen therethrough, the lumen having a diameter, and the channel being dimensioned to be disposable within the catheter;
  at least one anchor, including an anchor head coupled to a tissue-coupling element, the anchor head defining an aperture therethrough, and
  an anchor driver:
    including a stem, and a driver head coupled to the distal end of the stem, the driver head being reversibly couplable to the anchor head, configured to advance the anchor through the lumen of the channel while the driver head is coupled to the anchor head, further including a lance that is reversibly extendable with respect to the driver head, such that when the driver head is coupled to the anchor head, extension of the lance causes the lance to slide through the aperture such that a tip of the lance becomes disposed distally beyond a distal tip of the tissue-engaging element, and configured to drive the tip of the lance through a portion of the implant and into the tissue of the subject, and to drive the tissue-coupling element of the anchor through the portion of the implant and into the tissue of the subject, independently of the driving of the tip of the lance.

There is further provided, in accordance with an application of the present invention, apparatus, for use with a tissue of a subject, the apparatus including:

an anchor, including:
  an anchor head, having a proximal side and a distal side, and defining an aperture from the proximal side to the distal side,
  a tissue-engaging member, coupled to the anchor head, extending distally away from the anchor head until a distal tip of the tissue-engaging member, and configured to anchor the anchor to the tissue;
an anchor driver, including:
  a longitudinal shaft, having a flexible distal portion and a distal end,
  a tissue-piercing lance, reversibly extendible distally from the shaft,
  a deployment element coupled to the distal end of the shaft, and reversibly couplable to the anchor head in a position in which extension of the lance distally from the shaft moves the lance through the aperture and past the distal tip of the anchor; and
a catheter system, including:
  a catheter:
    through which the anchor driver is intracorporeally advanceable (i) while the deployment element is coupled to the anchor head, and (ii) such that the distal portion of the shaft extends distally out of the catheter, and
    having a distal segment that is intracorporeally deflectable with respect to another segment of the catheter immediately proximal to the distal segment, and
  an extracorporeal controller configured, while the distal portion of the shaft is extended distally out of the catheter, and the lance is extended distally from the shaft and is disposed in the tissue, to cause deflection of the distal segment with respect to the other segment, such that the distal portion of the shaft deflects with respect to another portion of the shaft immediately proximal to the distal portion,
the anchor driver being configured to drive the tissue-engaging member into the tissue while the distal portion of the shaft is deflected with respect to the other portion of the shaft.

There is further provided, in accordance with an application of the present invention, a method, including:

advancing a distal end of an anchor driver through a catheter and toward a tissue of a subject, the anchor driver including a shaft, a tissue-piercing lance, and a deployment element;

subsequently, piercing the tissue with the lance;

deflecting a distal portion of the shaft with respect to another portion of the shaft immediately proximal to the distal portion, by moving a distal segment of the catheter while at least some of the lance is disposed within the tissue; and while (i) the distal portion of the shaft is deflected with respect to the other portion of the shaft, and (ii) the deployment element is locked to a head of an anchor, driving a tissue-engaging member of the anchor into the tissue using the anchor driver.

There is further provided, in accordance with an application of the present invention, a method for use with an implant, the method including:

using an implant-manipulating handle, coupled to the implant, to percutaneously advance the implant through a catheter toward an implant site of a subject;

by applying a first force to the implant-manipulating handle, sliding the implant with respect to the catheter without causing the implant to apply force to tissue at the implant site;

measuring a magnitude of the first force;

subsequently, anchoring the implant to tissue at the implant site;

subsequently, by applying a second force to the implant-manipulating handle, causing the implant to apply a third force to tissue at the implant site via the anchoring of the implant;

measuring a magnitude of the second force; and determining a magnitude of the third force at least in part responsively to a difference between the magnitude of the first force and the magnitude of the second force.

In an application, sliding the implant by applying the first force to the implant-manipulating handle includes sliding the implant proximally with respect to the catheter by applying the first force to the implant-manipulating handle.

In an application:
  measuring the magnitude of the first force includes measuring the magnitude of the first force using a force gauge,
  measuring the magnitude of the second force includes measuring the magnitude of the second force using the force gauge, and
  the method further includes, subsequently to measuring the magnitude of the first force and prior to causing the implant to apply the third force, zeroing the force gauge to the magnitude of the first force.

In an application:
  the anchor-manipulator handle includes a force gauge,
  measuring the magnitude of the first force includes measuring the magnitude of the first force using the force gauge, and
  measuring the magnitude of the second force includes measuring the magnitude of the second force using the force gauge.

In an application, anchoring the implant includes anchoring the implant by driving a tissue anchor into tissue at the implant site.

In an application, causing the implant to apply the third force by applying the second force to the implant-manipulating handle includes, by applying the second force to the implant-manipulating handle, causing the implant to apply the third force via the tissue anchor.

There is further provided, in accordance with an application of the present invention, apparatus, including:

a percutaneously-implantable implant;

an adjustment device, including:

an adjustment mechanism, coupled to the implant, and configured to change a dimension of the implant upon actuation of the adjustment mechanism; and
a lock:
having a locked state in which the lock inhibits actuation of the adjustment mechanism,
having an unlocked state in which the adjustment mechanism is actuatable, and
reversibly movable between the locked state and the unlocked state;
a longitudinal guide member; and
an adapter:
coupled to the guide member,
including a fastener that couples the adapter to the adjustment device, and is intracorporeally decouplable from the adjustment device,
configured to be percutaneously delivered while coupled to the adjustment device, and
including an unlocking mechanism, configured such that, while the adapter is coupled to the adjustment device, actuation of the unlocking mechanism moves the lock between the locked state and the unlocked state.

In an application, the actuation of the unlocking mechanism moves the lock from the locked state to the unlocked state by the unlocking mechanism pressing on a depressible portion of the lock.

In an application, the unlocking mechanism includes a pin disposed in a channel, and the actuation of the unlocking mechanism that moves the lock from the locked state to the unlocked state includes sliding of the pin within the channel.

In an application, the fastener is shaped to define at least part of the channel.

In an application:
the adjustment device is shaped to define a first screw thread, and
the fastener (i) is shaped to define a second screw thread that couples the fastener to the adjustment device by engaging the first screw thread, and (ii) is intracorporeally decouplable from the adjustment device by the second screw thread being unscrewed from the first screw thread.

In an application, the lock is biased to be in the locked state in the absence of the pressing of the depressible portion.

In an application, the apparatus further includes an adjustment tool, and the adjustment tool:
is percutaneously advanceable along the guide member to the adapter, subsequently to implantation of the implant,
includes an adjustment-mechanism interface, dimensioned to interface with the adjustment mechanism,
includes an adapter interface, dimensioned to interface with the adapter, and including a force applicator, and
is configured:
to move the lock into the unlocked state by, while the adapter is coupled to the adjustment device, actuating the unlocking mechanism by applying, with the force applicator, a force to the unlocking mechanism, and
to actuate the adjustment mechanism via the interface between the adjustment-mechanism interface and the adjustment mechanism.

In an application, the tool is configured to decouple the adapter from the adjustment device.

In an application, the adjustment-mechanism interface and the adapter interface are independently controllable.

In an application, the tool is configured to decouple the adapter from the adjustment device independently of actuating the unlocking mechanism.

In an application, the force applicator is axially slidable with respect to the adapter, and is configured to actuate the unlocking mechanism by applying an axial force to the unlocking mechanism.

In an application:
the adapter includes a trunk that is shaped to define a channel,
the unlocking mechanism includes the channel, and a pin disposed and slidable within the channel, and
the force applicator is configured to actuate the unlocking mechanism by sliding the pin within the channel by applying an axial force to the pin.

In an application, the trunk is shaped to define a lateral opening, the pin includes an appendage that protrudes laterally out of the opening, and the adapter interface is dimensioned to be slidable over a proximal portion of the trunk to a sufficient extent that the force applicator reaches the appendage.

In an application, a transverse cross-section of the proximal portion of the trunk has an external shape that is non-circular, and the tool is configured to decouple the adapter from the adjustment device by applying torque to the trunk via the adapter interface.

In an application, a distal portion of the adapter interface is angled such that, in response to sliding of the adapter interface axially over the proximal portion of the trunk, the adapter interface automatically assumes a pre-determined rotational orientation with respect to the trunk.

In an application, the distal portion of the adapter interface is angled such that in the pre-determined rotational orientation the force applicator is aligned with the appendage.

In an application, the force applicator is angled such that, in response to sliding of the adapter interface axially over the proximal portion of the trunk, the adapter interface automatically assumes a pre-determined rotational orientation with respect to the trunk.

In an application, the distal portion of the adapter interface is angled such that in the pre-determined rotational orientation the force applicator is aligned with the appendage.

In an application, while the adapter interface assumes the pre-determined rotational orientation in which the force applicator is aligned with the appendage, the non-circular shape of the proximal portion of the trunk inhibits the adapter interface from rotating further in response to further sliding of the adapter interface axially over the trunk.

In an application, the trunk is shaped to define one or more shoulders that are angled such that, in response to sliding of the adapter interface axially over the shoulders, the adapter interface automatically assumes a pre-determined rotational orientation with respect to the trunk.

In an application, the distal portion of the adapter interface is angled such that in the pre-determined rotational orientation the force applicator is aligned with the appendage.

There is further provided, in accordance with an application of the present invention, apparatus, for use with a tissue of a subject, the apparatus including an annuloplasty structure, the annuloplasty structure including:
a sleeve, having a first end and a second end, a bearing site, and including a lateral wall that defines a lumen from the first end to the second end,
an adjustment mechanism, and a contraction member:
  having a first end coupled to the adjustment mechanism,
  having a first portion that extends from the adjustment mechanism along the sleeve toward the second end, until the bearing site, and
  having a second portion that extends from the bearing site back toward the adjustment mechanism and the first end,
the adjustment mechanism being configured to reduce a length of the sleeve between the first end and the second end by pulling on the first portion of the contraction member such that the second portion of the contraction member progressively slides past the bearing site.

In an application, the first portion weaves through the lateral wall of the sleeve.

In an application, the second portion weaves through the lateral wall of the sleeve.

In an application, the first portion passes along the lumen.

In an application, the second portion passes along the lumen.

In an application, the contraction member has a second end that is fixedly coupled to the sleeve.

In an application, the sleeve has a hole therein, the hole defining the bearing site, the contraction member being slidable through the hole.

There is further provided, in accordance with an application of the present invention, a method, including:
  percutaneously advancing toward a tissue of a subject an implant including a sleeve that defines a tubular lateral wall and a lumen, while a distal portion of an anchor-delivery channel is disposed within the lumen, such that a distal opening of the channel is disposed at a first portion of the sleeve;
  anchoring the first portion of the sleeve to a first tissue site by using an anchor driver to drive a tissue-coupling element of a first anchor through the distal opening of the channel, through the lateral wall at the first portion of the sleeve, and into the first tissue site;
  pressing a second portion of the sleeve against a second tissue site; and
  anchoring the second portion of the sleeve to a second tissue site by driving a tissue-coupling element of a second anchor from outside the lumen, through opposing sides of the lateral wall at the second portion of the sleeve, and into the second tissue site.

In an application, pressing the second portion of the sleeve against the second tissue site includes pressing the second portion of the sleeve against the second tissue site such that the opposing sides of the lateral wall at the second portion of the sleeve contact each other.

In an application:
  the implant includes an annuloplasty structure that includes the sleeve,
  anchoring the first portion of the sleeve to the first tissue site includes anchoring the first portion of the sleeve to an annulus of an atrioventricular valve of a heart of a subject, and
  anchoring the second portion of the sleeve to the second tissue site includes anchoring the second portion of the sleeve to a wall of an atrium of the heart of the subject.

There is further provided, in accordance with an application of the present invention, a method, including:
  percutaneously advancing toward a tissue of a subject an implant including a sleeve, while a distal portion of an anchor-delivery channel is disposed within a lumen defined by the sleeve, such that a distal opening of the channel is disposed at a first portion of the sleeve;
  anchoring the first portion of the sleeve to the tissue by using an anchor driver to drive a tissue-coupling element of a first anchor through the distal opening of the channel, through the sleeve, and into the tissue;
  subsequently, while providing a distally-directed reference force to the first anchor via the driver, proximally withdrawing the distal portion of the channel such that the distal opening of the channel is disposed at a second portion of the sleeve;
  subsequently, proximally withdrawing the driver through the channel; and
  subsequently, anchoring the second portion of the sleeve to the tissue by driving a tissue-coupling element of a second anchor through the distal opening of the channel, through the sleeve, and into the tissue.

There is further provided, in accordance with an application of the present invention, apparatus, for use with a tissue of a subject, the apparatus including:
  a percutaneous catheter;
  an implant, dimensioned to be advanced into the subject via the catheter;
  an anchor-delivery channel, shaped to define a lumen therethrough, the lumen having a diameter, and the channel being dimensioned to be disposable within the catheter;
  at least one small anchor, including a small-anchor anchor head coupled to a small-anchor tissue-coupling element, and having a central longitudinal axis from the small-anchor anchor head to the small-anchor tissue-coupling element, a greatest transverse width of the small anchor being smaller than the diameter of the lumen of the channel;
  at least one large anchor, including a large-anchor anchor head coupled to a large-anchor tissue-coupling element, and having a central longitudinal axis from the large-anchor anchor head to the large-anchor tissue-coupling element, a greatest transverse width of the large anchor being greater than the diameter of the lumen of the channel; and
  an anchor driver, including a driver head that is reversibly couplable to the large-anchor anchor head, and a stem that is dimensioned to extend, while the driver head is coupled to the large-anchor anchor head, from the driver head, through the lumen of the channel, and out of a proximal end of the channel.

In an application:
  the large anchor is disposed at a distal portion of the channel, with at least the large-anchor tissue-coupling element outside of the lumen of the channel,
  the driver head is coupled to the large-anchor anchor head,
  the stem extends from the driver head, proximally through the lumen of the channel, and out of the proximal end of the channel,
  the implant is shaped to define a lumen,
  the distal portion of the channel and the large-anchor tissue-coupling element are disposed within the lumen of the implant, and are slidable through the catheter with the implant while within the lumen of the implant.

In an application, the diameter of the lumen of the channel is 2-3 mm.

In an application, the greatest transverse width of the large anchor is 3-4 mm.

In an application, the large-anchor tissue-engaging element is shaped to define a helix having a transverse width of 3-4 mm.

In an application, the large-anchor anchor head has a greatest transverse width of 2-3 mm.

In an application, the small-anchor tissue-engaging element is shaped to define a helix having a transverse width of 2-3 mm.

In an application, the greatest transverse width of the large anchor is a greatest transverse width of the large-anchor tissue-coupling element.

In an application, the large-anchor anchor head has a greatest transverse width that is smaller than the diameter of the lumen of the channel.

In an application, the large-anchor anchor head has a greatest transverse width that is greater than the diameter of the lumen of the channel.

There is additionally provided, in accordance with some applications of the present invention, an implant having a body portion, the implant including:
　a contraction member;
　an actuatable adjustment mechanism, coupled to the contraction member, and configured to, when actuated, adjust a dimension of the body portion of the implant by applying tension to the contraction member; and
　an adjustment indicator, coupled to the contraction member and directly coupled to the body portion of the implant, and configured to change shape according to a degree of tension of the contraction member.

In some applications of the present invention, the implant includes an annuloplasty ring structure.

In some applications of the present invention, the body portion includes a sleeve.

In some applications of the present invention, the adjustment indicator is directly coupled to an external surface of the body portion of the implant.

In some applications of the present invention, the adjustment indicator includes a radiopaque element.

In some applications of the present invention, the implant includes an annuloplasty structure, and the contraction member is coupled to the annuloplasty structure via the radiopaque element.

In some applications of the present invention:
　the radiopaque element includes:
　a receptacle; and
　a plug shaped so as to fit within the receptacle, the contraction member is coupled to the radiopaque element by being coupled to the plug such that an increase in the degree of tension of the contraction member changes the shape of the radiopaque element by positioning the plug within the receptacle.

In some applications of the present invention, the radiopaque element is disposed adjacent to the adjustment mechanism.

In some applications of the present invention, the adjustment mechanism is coupled to the contraction member at a first end portion of the contraction member, and the radiopaque element is coupled to the contraction member at a second end portion of the contraction member.

In some applications of the present invention, contraction member is threaded through the radiopaque element.

In some applications of the present invention, the implant includes an annuloplasty structure, and the radiopaque element is coupled to the contraction member such that an increase in the degree of tension of the contraction member changes the shape of the radiopaque element by pressing the radiopaque element against the annuloplasty structure.

In some applications of the present invention, the radiopaque element includes a band.

In some applications of the present invention, the band has a width of 1-3 mm.

In some applications of the present invention:
　when tension is not applied to the contraction member, a shape of the band in an unpressed state has an unpressed longitudinal length of 4-6 mm measured along a longitudinal axis of the band, and
　in response to an increase in the degree of tension of the contraction member, at least a portion of the band is pressed against the implant assuming a pressed state, and has a pressed longitudinal length of 7-10 mm measured along the longitudinal axis of the band.

In some applications of the present invention, the radiopaque element includes a tube surrounding a portion of the contraction member.

In some applications of the present invention, the radiopaque element is coupled to the contraction member such that an increase in the degree of tension of the contraction member changes the shape of the radiopaque element by compressing the tube.

In some applications of the present invention, the radiopaque element includes a spring.

In some applications of the present invention, the radiopaque element is coupled to the contraction member such that an increase in the degree of tension of the contraction member changes the shape of the radiopaque element by expanding the spring.

In some applications of the present invention, the spring includes a volute spring.

In some applications of the present invention, the spring includes a telescoping spring surrounding a portion of the contraction member.

In some applications of the present invention, the radiopaque element is coupled to the contraction member such that an increase in the degree of tension of the contraction member changes the shape of the radiopaque element by compressing the spring.

In some applications of the present invention:
　the radiopaque element is shaped so as to define at least first and second arms, and
　the contraction member is coupled to the radiopaque element by being coupled to each of the first and second arms such that an increase in the degree of tension of the contraction member changes the shape of the radiopaque element by changing a distance between the first and second arms.

In some applications of the present invention, in response to the increase in the degree of tension of the contraction member, the first and second arms are drawn toward each other.

In some applications of the present invention, the contraction member is threaded through respective portions of the first and second arms.

There is yet additionally provided, in accordance with some applications of the present invention, an implant, the implant including:
　an annuloplasty structure having a primary body portion;
　a contraction member, extending along at least a contracting portion of the annuloplasty structure;
　an actuatable adjustment mechanism, coupled to the contraction member, and configured to, when actuated, adjust a length of the annuloplasty structure by applying tension to the contraction member; and a contraction-member-protecting element, having a first end coupled to the primary body portion of the annuloplasty structure, and a second end coupled to the adjustment mechanism, the contraction member extends from the adjustment mechanism via the contraction-member-protecting element to the primary body portion of the annuloplasty structure.

In some applications of the present invention, the first end of the contraction-member-protecting element is connected to the annuloplasty structure at a connection point that is at least 10 mm from any end of the annuloplasty structure.

In some applications of the present invention, the annuloplasty structure includes a primary sleeve that includes a tubular lateral wall that defines a primary lumen through the primary sleeve, the contraction-member-protecting element includes a secondary sleeve that defines a secondary lumen through the secondary sleeve, and a portion of the contraction member is disposed within secondary lumen.

In some applications of the present invention, the contraction-member-protecting element includes a band, and the contraction member is threaded through the band.

In some applications of the present invention, the band has a width of 3-5 mm.

In some applications of the present invention, the band has a band width that is 10 times greater than a width of the contraction member.

In some applications of the present invention, the contraction-member-protecting element includes a spring, and the contraction member is disposed within a lumen of the spring.

In some applications of the present invention:
the first end of the contraction-member-protecting element is connected to the annuloplasty structure at a connection point,
the annuloplasty structure defines a central longitudinal axis,
the implant has a delivery state in which:
the implant is percutaneously advanceable through the catheter to an implant site, and
the adjustment mechanism is disposed on the central longitudinal axis, distal to the annuloplasty structure, and the contraction-member-protecting element extends from the connection point, alongside the annuloplasty structure, to the adjustment mechanism, the implant has a deployed state in which:
the adjustment mechanism is disposed laterally to the central longitudinal axis, and
tensioning of the contraction member by the adjustment mechanism moves the adjustment mechanism closer to the connection point, and compresses the contraction-member-protecting element.

In some applications of the present invention, the contraction-member-protecting element has a longitudinal length of 10-15 mm prior to the tensioning of the contraction member when measured along the central longitudinal axis of the contraction-member-protecting element.

In some applications of the present invention, the apparatus further includes a plurality of tissue anchors:
the annuloplasty structure has a distal end, and a distal portion that extends between the connection point and the distal end,
the plurality of tissue anchors includes (i) at least three tissue anchors disposed at the distal portion of the annuloplasty structure, and (ii) at least one tissue anchor disposed in the contracting portion of the annuloplasty structure.

There is further provided, in accordance with some applications of the present invention, apparatus, including an implant, the implant including:
an annuloplasty structure including a primary sleeve that includes a tubular lateral wall that defines a primary lumen through the primary sleeve;
a contraction member, having a first portion extending along at least a contracting portion of the primary sleeve of the annuloplasty structure, the contraction member exiting the primary lumen at an exit point of the primary lumen;
an actuatable adjustment mechanism, coupled to the contraction member at an end portion of the contraction member, and configured to, when actuated, adjust a length of the annuloplasty structure by applying tension to the contraction member; and
a secondary sleeve coupled to the primary sleeve at the exit point of the contraction member from the primary lumen, the secondary sleeve:
defining a secondary lumen through the secondary sleeve, a second portion of the contraction member is disposed within secondary lumen and extends to the adjustment mechanism, and
coupling the adjustment mechanism to the primary sleeve.

There is yet further provided, in accordance with some applications of the present invention, apparatus for use with a subject, the apparatus including:
a catheter, transluminally advanceable into the subject; and
an implant advanceable through the catheter, the implant including a flexible sleeve that defines a lumen having a proximal end, a distal end, and a central longitudinal axis therebetween, the implant being twisted about the longitudinal axis of the sleeve and being longitudinally slidable through the catheter while the sleeve is twisted about the longitudinal axis of the sleeve.

In some applications of the present invention, an angle of twist between a proximal end and a distal end of the sleeve that is 170-190 degrees.

In some applications of the present invention, the apparatus further includes a channel longitudinally slidable through the catheter, the flexible sleeve of the implant encases a distal portion of the channel while the sleeve is twisted about the axis of the sleeve, and the implant is longitudinally slidable through the catheter with the channel, while the sleeve encases the distal portion of the channel while the sleeve is twisted about the axis of the sleeve.

In some applications of the present invention, the apparatus further includes:
a contraction member that extends longitudinally along the sleeve; and
an actuatable adjustment mechanism, coupled to the contraction member, and configured to, when actuated, adjust a dimension of the implant by applying tension to the contraction member.

In some applications of the present invention, the contraction member has a first end portion that is coupled to the adjustment mechanism, and a second end portion that is coupled to the sleeve of the implant, while the sleeve is twisted about the axis of the sleeve, the adjustment mechanism is twisted from the second end portion of the contraction member at an angle of twist between 155 and 175 degrees.

In some applications of the present invention, the apparatus further includes a channel longitudinally slidable through the catheter, the flexible sleeve of the implant encases a distal portion of the channel while twisted about the axis of the sleeve, and the implant is longitudinally slidable through the catheter with the channel, while the sleeve encases the distal portion of the channel while twisted about the axis of the sleeve.

In some applications of the present invention, when the sleeve encases the distal portion of the channel while twisted about the axis of the sleeve, the implant is rotated around a central longitudinal axis of the channel.

In some applications of the present invention, the contraction member has a first end portion that is coupled to the adjustment mechanism, and a second end portion that is coupled to a portion of the sleeve of the implant, and the contraction member defines:
   a first longitudinal portion that extends from the adjustment mechanism along a first longitudinal path,
   a second longitudinal portion that extends to the portion of the sleeve of the implant along a second longitudinal path that is offset with respect to the first longitudinal path, and
   an offsetting portion which offsets the first and second longitudinal portions of the contraction member.

In some applications of the present invention, the offsetting portion extends along a stepped path.

In some applications of the present invention, the offsetting portion extends along a helical path.

In some applications of the present invention, the sleeve of the implant is tubular and the first and second longitudinal portions are offset by a distance of 0.3-0.7 radians.

In some applications of the present invention, the first and second longitudinal portions are offset by a distance of 0.8-1.2 mm.

There is additionally provided, in accordance with some applications of the present invention, apparatus, including an implant, the implant including:
   an annuloplasty structure having a body portion;
   a contraction member, extending along at least a contracting portion of the annuloplasty structure; and
   an actuatable adjustment mechanism, coupled to the contraction member, and configured to, when actuated, adjust a length of the annuloplasty structure by applying tension to the contraction member,
   the contraction member has a first end portion that is coupled to the adjustment mechanism, and a second end portion that is coupled to a portion of the body portion of the implant, the contraction member defining:
      a first longitudinal portion that extends from the adjustment mechanism along a first longitudinal path,
      a second longitudinal portion that extends to the portion of the sleeve of the implant along a second longitudinal path that is offset with respect to the first longitudinal path, and
      an offsetting portion which offsets the first and second longitudinal portions of the contraction member.

There is additionally provided, in accordance with some applications of the present invention, apparatus for use with a subject, the apparatus including:
   a flexible sleeve, transluminally advanceable into the subject, and including a tubular lateral wall that (i) circumscribes a central longitudinal axis of the sleeve, and (ii) defines a lumen having a distal end, a proximal end, and a length therebetween; and
   a longitudinal contraction member:
      coupled to the flexible sleeve such that tensioning the contraction member reduces the length of the lumen, and
      coupled to the lateral wall such that, in an absence of torsion of the sleeve around the longitudinal axis, at least part of the contraction member is disposed helically around the longitudinal axis.

In some applications of the present invention, the contraction member is woven through the lateral wall.

In some applications of the present invention, the contraction member extends along at least a contracting portion of the sleeve.

In some applications of the present invention, the contraction member extends along at least the contracting portion of the sleeve at an angle of twist between a proximal end and a distal end of the sleeve that is 170-190 degrees.

In some applications of the present invention, further including an actuatable adjustment mechanism coupled to the contraction member, and configured to, when actuated, adjust a dimension of the sleeve by applying tension to the contraction member.

In some applications of the present invention, the contraction member has a first end portion that is coupled to the adjustment mechanism, and a second end portion that is coupled to the sleeve of the implant, while the contraction member is disposed helically about the axis of the sleeve, the adjustment mechanism is twisted from the second end portion of the contraction member at an angle of twist between 140-180 degrees.

There is yet additionally provided, in accordance with some applications of the present invention, apparatus for use with a subject, the apparatus including:
   a primary body portion, transluminally advanceable into the subject that has a distal end, a proximal end, and a length therebetween measured along a longitudinal axis of the primary body portion; and
   a longitudinal contraction member:
      coupled to the primary body portion such that tensioning the contraction member reduces the length of the primary body portion, and
      coupled to the primary body portion such that, in an absence of torsion of the primary body portion around the longitudinal axis, at least part of the contraction member is disposed helically around the longitudinal axis.

There is yet further provided, in accordance with some applications of the present invention, apparatus for use with a subject, the apparatus including:
   an annuloplasty structure having a primary body portion, the annuloplasty structure being transluminally advanceable into the subject; and
   a longitudinal contraction member:
      coupled to the annuloplasty structure such that tensioning the contraction member reduces a length of the primary body portion of the annuloplasty structure, and
      woven a plurality of times through the primary body portion,
      the primary body portion of the annuloplasty structure defines first and second holes, a portion of the contraction member exiting away from the primary body portion through the first hole and reengaging the primary body portion through the second hole.

In some applications of the present invention:
   the primary body portion includes a sleeve defining a lumen therethrough,
   the contraction member is woven in and out of the lumen of the sleeve, and
   the sleeve defines first and second holes, a portion of the contraction member exiting away from the sleeve through the first hole and reentering the lumen of the sleeve through the second hole.

In some applications of the present invention, the second hole is disposed at a distance of 16-22 mm from an end of the primary body portion.

In some applications of the present invention, the primary body portion defines a contraction-member-free section of the primary body portion that is between the first and second holes has a degree of friction that is less than sections of the primary body portion that are adjacent to the first and second holes and to the contraction-member-free section.

In some applications of the present invention, the apparatus further includes an actuatable adjustment mechanism coupled to the contraction member, and configured to, when actuated, adjust a dimension of the primary body portion of the annuloplasty structure by applying tension to the contraction member.

In some applications of the present invention, the contraction member has a first end portion that is coupled to the adjustment mechanism, and a second end portion that is coupled to the primary body portion of the annuloplasty structure.

In some applications of the present invention, the apparatus further includes a contraction-member-protecting element, having a first end coupled to the primary body portion of the annuloplasty structure, and a second end coupled to the adjustment mechanism, the contraction member extends from the adjustment mechanism via the contraction-member-protecting element to the primary body portion of the annuloplasty structure.

In some applications of the present invention, the first end of the contraction-member-protecting element is connected to the annuloplasty structure at a connection point that is at least 10 mm from any end of the annuloplasty structure.

In some applications of the present invention, the first and second holes are disposed in a vicinity of the connection point.

There is also provided, in accordance with some applications of the present invention, apparatus for use with a subject, the apparatus including:
  an annuloplasty structure having a primary body portion, the annuloplasty structure being transluminally advanceable into the subject; and
  a longitudinal contraction member coupled to the annuloplasty structure such that tensioning the contraction member reduces a length of the primary body portion of the annuloplasty structure,
  the annuloplasty structure defines a first portion having a first degree of friction between the primary body portion and a first portion of the contraction member, and the annuloplasty structure defines a second portion having a second degree of friction between the primary body portion and a second portion of the contraction member, the second degree of tension being less than the first degree of tension.

In some applications of the present invention:
  the first portion of the contraction member is woven a plurality of times through the primary body portion in the first portion of the annuloplasty structure, and
  the second portion of the annuloplasty structure defines first and second holes in the primary body portion of the annuloplasty structure, the second portion of the contraction member exiting away from the primary body portion through the first hole and reengaging the primary body portion through the second hole.

There is also provided, in accordance with some applications of the present invention, apparatus, including:
  a tube having a distal end configured for advancement into a heart of a patient;
  an implant moveable at least in part through a lumen of the tube, the implant including:
    an annuloplasty structure having a body portion;
    a contraction member, extending along at least a contracting portion of the annuloplasty structure and until 10-15 mm from an end of the body portion; and
    an actuatable adjustment mechanism, coupled to the contraction member, and configured to, when actuated, adjust a length of the annuloplasty structure by applying tension to the contraction member, a portion of the adjustment mechanism is disposed distally to the distal end of the tube while the contraction member is disposed entirely within the tube.

In some applications of the present invention, the adjustment mechanism is movable with respect to the primary body portion.

There is also provided, in accordance with some applications of the present invention, apparatus, including:
  a tube having a distal end configured for advancement into a heart of a patient;
  an implant moveable at least in part through a lumen of the tube, the implant including:
    an annuloplasty structure having a body portion;
    a contraction member, extending along at least a contracting portion of the annuloplasty structure and until 10-15 mm from an end of the body portion; and
    an actuatable adjustment mechanism, coupled to the contraction member, and configured to, when actuated, adjust a length of the annuloplasty structure by applying tension to the contraction member,
  a distal-most portion of the contraction member is disposed distally to the distal end of the tube at a first distance from the distal end of the tube and a portion of the adjustment mechanism is disposed distally to the contraction member at a second distance from the distal end of the tube that is greater than the first distance.

There is also provided, in accordance with some applications of the present invention, the following inventive concepts:
  1. A method, comprising:
    advancing a distal end of an anchor driver through a catheter and toward a tissue of a subject, the anchor driver including a shaft, a tissue-piercing lance, and a deployment element;
    subsequently, piercing the tissue with the lance;
    deflecting a distal portion of the shaft with respect to another portion of the shaft immediately proximal to the distal portion, by moving a distal segment of the catheter while at least some of the lance is disposed within the tissue; and
    while (i) the distal portion of the shaft is deflected with respect to the other portion of the shaft, and (ii) the deployment element is locked to a head of an anchor, driving a tissue-engaging member of the anchor into the tissue using the anchor driver.
  2. A method for use with an implant, the method comprising:
    using an implant-manipulating handle, coupled to the implant, to percutaneously advance the implant through a catheter toward an implant site of a subject;
    by applying a first force to the implant-manipulating handle, sliding the implant with respect to the catheter without causing the implant to apply force to tissue at the implant site;

measuring a magnitude of the first force;
subsequently, anchoring the implant to tissue at the implant site;
subsequently, by applying a second force to the implant-manipulating handle, causing the implant to apply a third force to tissue at the implant site via the anchoring of the implant;
measuring a magnitude of the second force; and
determining a magnitude of the third force at least in part responsively to a difference between the magnitude of the first force and the magnitude of the second force.

3. The method according to inventive concept 2, sliding the implant by applying the first force to the implant-manipulating handle comprises sliding the implant proximally with respect to the catheter by applying the first force to the implant-manipulating handle.

4. The method according to inventive concept 2, wherein:
measuring the magnitude of the first force comprises measuring the magnitude of the first force using a force gauge,
measuring the magnitude of the second force comprises measuring the magnitude of the second force using the force gauge, and
the method further comprises, subsequently to measuring the magnitude of the first force and prior to causing the implant to apply the third force, zeroing the force gauge to the magnitude of the first force.

5. The method according to inventive concept 2, wherein:
the anchor-manipulator handle includes a force gauge,
measuring the magnitude of the first force comprises measuring the magnitude of the first force using the force gauge, and
measuring the magnitude of the second force comprises measuring the magnitude of the second force using the force gauge.

6. The method according to any one of inventive concepts 2-5, anchoring the implant comprises anchoring the implant by driving a tissue anchor into tissue at the implant site.

7. The method according to inventive concept 6, causing the implant to apply the third force by applying the second force to the implant-manipulating handle comprises, by applying the second force to the implant-manipulating handle, causing the implant to apply the third force via the tissue anchor.

8. A method for using an adjustment tool with an implant, the method comprising:
transluminally implanting the implant in a heart of a subject, such that a guide wire extends from an adjustment device of the implant, the adjustment device including an adjustment mechanism and a lock, the adjustment mechanism configured to change a dimension of the implant upon actuation of the adjustment mechanism, and the lock having (i) a locked state in which the lock inhibits actuation of the adjustment mechanism, and (ii) an unlocked state in which the adjustment mechanism is actuatable;
subsequently, advancing the adjustment tool along and over the guide wire to the adjustment device;
subsequently, using the tool, actuating the adjustment mechanism while the lock is in the unlocked state;
subsequently, unlocking the lock using the tool, and withdrawing the tool along and over the guide wire away from the adjustment device, leaving the lock in the locked state;
while the tool remains withdrawn, and is coupled to the adjustment device only by the guide wire, observing a function of the heart;
subsequently, returning the adjustment tool along and over the guide wire to the adjustment device, and using the tool: unlocking the lock, and actuating the adjustment mechanism; and
subsequently, (i) using the tool: locking the lock, and decoupling the guide wire from the locking device, and (ii) withdrawing the guide wire and the tool from the subject.

9. A method, comprising:
percutaneously advancing toward a tissue of a subject an implant including a sleeve that defines a tubular lateral wall and a lumen, while a distal portion of an anchor-delivery channel is disposed within the lumen, such that a distal opening of the channel is disposed at a first portion of the sleeve;
anchoring the first portion of the sleeve to a first tissue site by using an anchor driver to drive a tissue-coupling element of a first anchor through the distal opening of the channel, through the lateral wall at the first portion of the sleeve, and into the first tissue site;
pressing a second portion of the sleeve against a second tissue site; and
anchoring the second portion of the sleeve to a second tissue site by driving a tissue-coupling element of a second anchor from outside the lumen, through opposing sides of the lateral wall at the second portion of the sleeve, and into the second tissue site.

10. The method according to inventive concept 9, pressing the second portion of the sleeve against the second tissue site comprises pressing the second portion of the sleeve against the second tissue site such that the opposing sides of the lateral wall at the second portion of the sleeve contact each other.

11. The method according to inventive concept 9, wherein:
the implant includes an annuloplasty structure that includes the sleeve,
anchoring the first portion of the sleeve to the first tissue site comprises anchoring the first portion of the sleeve to an annulus of an atrioventricular valve of a heart of a subject, and
anchoring the second portion of the sleeve to the second tissue site comprises anchoring the second portion of the sleeve to a wall of an atrium of the heart of the subject.

12. A method, comprising:
percutaneously advancing toward a tissue of a subject an implant comprising a sleeve, while a distal portion of an anchor-delivery channel is disposed within a lumen defined by the sleeve, such that a distal opening of the channel is disposed at a first portion of the sleeve;
anchoring the first portion of the sleeve to the tissue by using an anchor driver to drive a tissue-coupling element of a first anchor through the distal opening of the channel, through the sleeve, and into the tissue;
subsequently, while providing a distally-directed reference force to the first anchor via the driver, proximally withdrawing the distal portion of the channel such that the distal opening of the channel is disposed at a second portion of the sleeve;
subsequently, proximally withdrawing the driver through the channel; and subsequently, anchoring the second portion of the sleeve to the tissue by driving a tissue-coupling element of a second anchor through the distal opening of the channel, through the sleeve, and into the tissue.

13. A method, comprising:
providing and implant including:
an annuloplasty structure having a body portion;
a contraction member having (1) a first portion extending along at least a contracting portion of the annuloplasty structure, and (2) a second portion that extends away from the body portion of the annuloplasty structure; and
an actuatable adjustment mechanism, coupled to the second portion of the contraction member, the second portion of the contraction member extending away from the body portion and to the adjustment mechanism, the adjustment mechanism configured to, when actuated, adjust a length of the body portion of the annuloplasty structure by applying tension to the contraction member; and
delivering the implant to a chamber of a heart of a subject through a catheter in a manner in which the adjustment mechanism is disposed distally to the body portion of the annuloplasty structure;
deploying a portion of the annuloplasty structure in the chamber such that the adjustment mechanism is distanced from the body portion of the annuloplasty structure by a distance of 10-15 mm via the second portion of the contraction member; and
subsequently to the deploying, reducing the distance between the adjustment mechanism and the body portion by actuating the adjustment mechanism.

14. A method, comprising:
transluminally advancing a catheter into a subject;
providing an implant, the implant including a flexible sleeve that defines a lumen having a proximal end, a distal end, and a central longitudinal axis therebetween; and
advancing the implant through the catheter, while the flexible sleeve encases the distal portion of the channel while twisted about the axis of the sleeve.

15. The method according to inventive concept 14, providing the implant further comprises providing a channel, the flexible sleeve encases a distal portion of the channel while twisted about the axis.

16. The method according to inventive concept 14, an angle of twist between the proximal end and the distal end is 170-190 degrees.

17. The method according to inventive concept 14, further comprising, subsequently to the advancing, progressively releasing successive portions of the sleeve off of the channel, and anchoring the successive portions to tissue of the subject, such that an angle of twist of the sleeve becomes reduced.

18. The method according to inventive concept 14, the providing the implant comprises providing the implant including:
a contraction member that extends longitudinally along the sleeve; and
an actuatable adjustment mechanism, coupled to the contraction member, and configured to, when actuated, adjust a dimension of the implant by applying tension to the contraction member.

19. The method according to inventive concept 18, the contraction member has a first end portion that is coupled to the adjustment mechanism, and a second end portion that is coupled to the sleeve of the implant, while the sleeve is twisted about the axis of the sleeve, the adjustment mechanism is twisted from the second end portion of the contraction member at an angle of twist between 170-190 degrees.

20. The method according to inventive concept 18, providing the implant further comprises providing a channel, the flexible sleeve encases a distal portion of the channel while twisted about the axis of the sleeve.

21. The method according to inventive concept 20, further comprising, prior to the advancing of the implant, when the sleeve encases the distal portion of the channel while twisted about the axis of the sleeve, rotating the implant in a first rotational direction around a central longitudinal axis of the channel.

22. A method for use with a heart of a subject, the method comprising:
using an implantation assembly, advancing, to a site in the heart, an implant that includes an implant-adjustment mechanism to which is coupled a flexible wire of the implantation assembly, the implantation assembly further including an adjustment tool that is slidable along and over the flexible wire, and is reversibly-engageable with the implant-adjustment mechanism;
securing the implant at the site in the heart, such that the flexible wire extends from the implant-adjustment mechanism out of the heart;
subsequently, actuating the implant-adjustment mechanism using the adjustment tool while the adjustment tool is disposed over the flexible wire, and is engaged with the implant-adjustment mechanism;
subsequently, disengaging and withdrawing the adjustment tool from the implant-adjustment mechanism by moving the adjustment tool along and over the flexible wire while the flexible wire remains coupled to the implant-adjustment mechanism;
subsequently, while (i) the adjustment tool remains withdrawn from the implant-adjustment mechanism, and (ii) the flexible wire remains coupled to the implant-adjustment mechanism, detecting a parameter of the heart;
subsequently, reengaging the adjustment tool with the implant-adjustment mechanism by moving the adjustment tool along and over the flexible wire toward the implant-adjustment mechanism while the flexible wire remains coupled to the implant-adjustment mechanism; and subsequently, re-actuating the implant-adjustment mechanism using the adjustment tool while the adjustment tool is disposed over the flexible wire, and is engaged with the implant-adjustment mechanism.

23. The method according to inventive concept 22, detecting the parameter of the heart comprises detecting the parameter of the heart while the flexible wire is the only part of the implantation assembly that is in contact with the implant.

24. The method according to inventive concept 22, further comprising:
locking the implant-adjustment mechanism after actuating the implant-adjustment mechanism, and before withdrawing the adjustment tool; and
unlocking the adjustment mechanism after moving the adjustment tool along and over the flexible wire toward the implant-adjustment mechanism, and before re-actuating the implant-adjustment mechanism.

25. The method according to inventive concept 24, locking the implant-adjustment mechanism comprises locking the implant-adjustment mechanism using the implantation assembly, and unlocking the implant-adjustment mechanism comprises unlocking the implant-adjustment mechanism using the implantation assembly.
26. The method according to inventive concept 22, further comprising, after re-actuating the implant-adjustment mechanism, decoupling the flexible wire from the adjustment mechanism.
27. The method according to inventive concept 26, decoupling the flexible wire from the implant-adjustment mechanism comprises using the implantation assembly to decouple the flexible wire from the implant-adjustment mechanism.
28. The method according to inventive concept 26, further comprising re-locking the implant-adjustment mechanism before decoupling the flexible wire from the adjustment mechanism.
29. The method according to inventive concept 22, detecting the parameter of the heart comprises detecting the parameter of the heart using echocardiography.

The present invention will be more fully understood from the following detailed description of embodiments thereof, taken together with the drawings, in which:

BRIEF DESCRIPTION OF THE DRAWINGS

FIGS. 3A-G are schematic illustrations of steps in the implantation of an annuloplasty ring structure to repair a mitral valve, in accordance with some applications of the invention;

FIGS. 4A and 4B are schematic illustrations that show steps between the state shown in FIG. 3C and the state shown in FIG. 3D, in accordance with respective applications of the invention;

FIGS. 8A-B, 9, 10A-C, 11, and 12A-B are schematic illustrations of tissue anchors, and the use of the tissue anchors for implantation of an implant, in accordance with some applications of the invention;

FIGS. 13A-D and 14A-F are schematic illustrations of a system, comprising a tissue anchor, an anchor driver, and a lance, and techniques for use with the system, in accordance with some applications of the invention;

FIGS. 15A-B are schematic illustrations of implants that comprise a contracting wire, in accordance with some applications of the invention;

FIGS. 16A-B, 17A-C and 18A-K are schematic illustrations of a system for docking with and adjusting an adjustment mechanism of a percutaneously-implantable implant, and techniques for use therewith, in accordance with some applications of the invention;

FIGS. 19A-F are schematic illustrations of a force gauge, and techniques for use thereof, in accordance with some applications of the invention;

FIGS. 22A-C are schematic illustrations of an annuloplasty structure in respective twisted and/or rotated states of delivery, in accordance with some applications of the invention;

FIGS. 26A-B, 27A-B, 28A-B, and 29A-B are schematic illustrations of an annuloplasty structure comprising respective adjustment indicators, in accordance with respective applications of the invention;

DETAILED DESCRIPTION OF EMBODIMENTS

Figure 1:
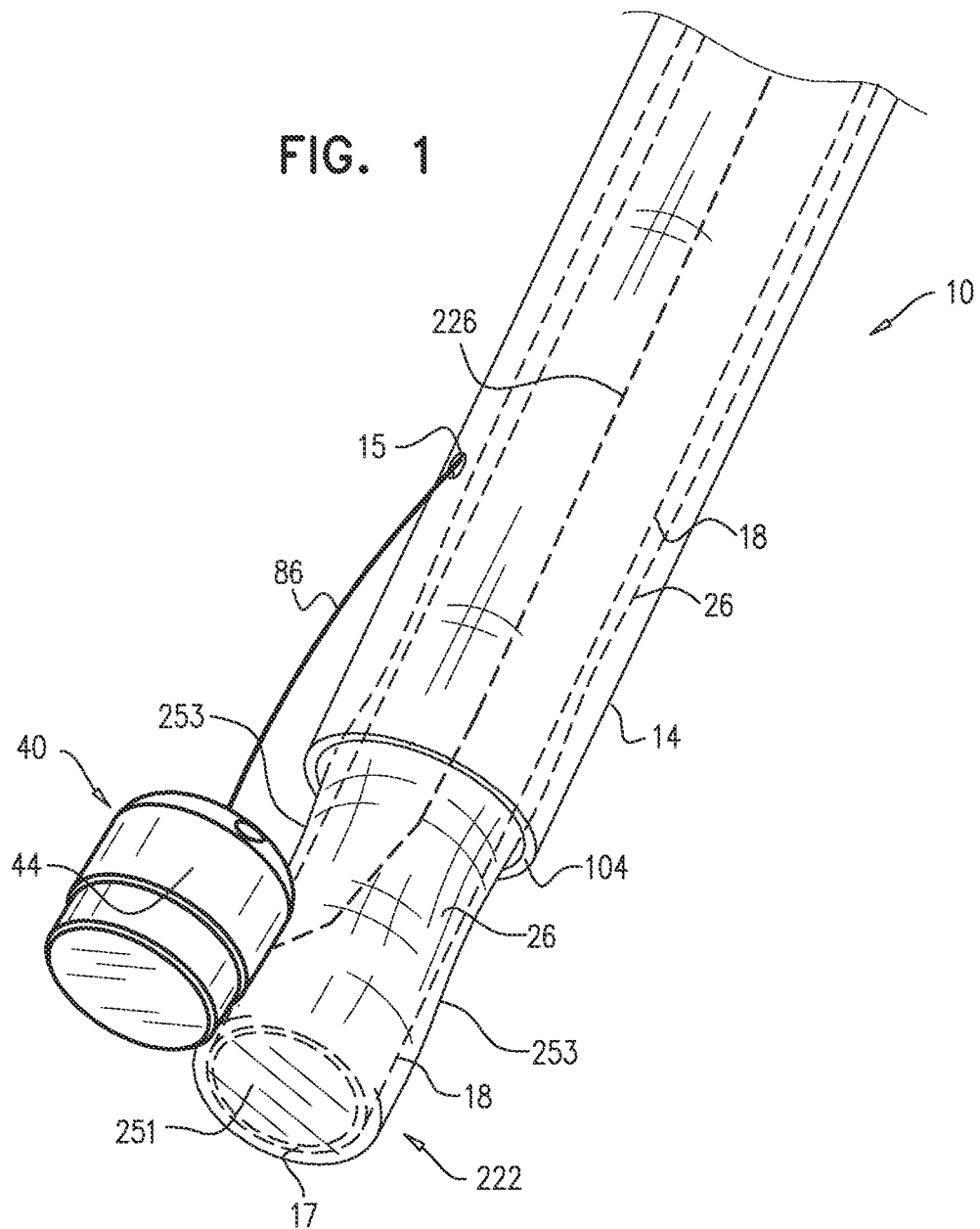
FIG. 1 is a schematic illustration of an annuloplasty ring structure, comprising a sleeve and an adjustment mechanism, in accordance with some applications of the invention.
Figure 2:
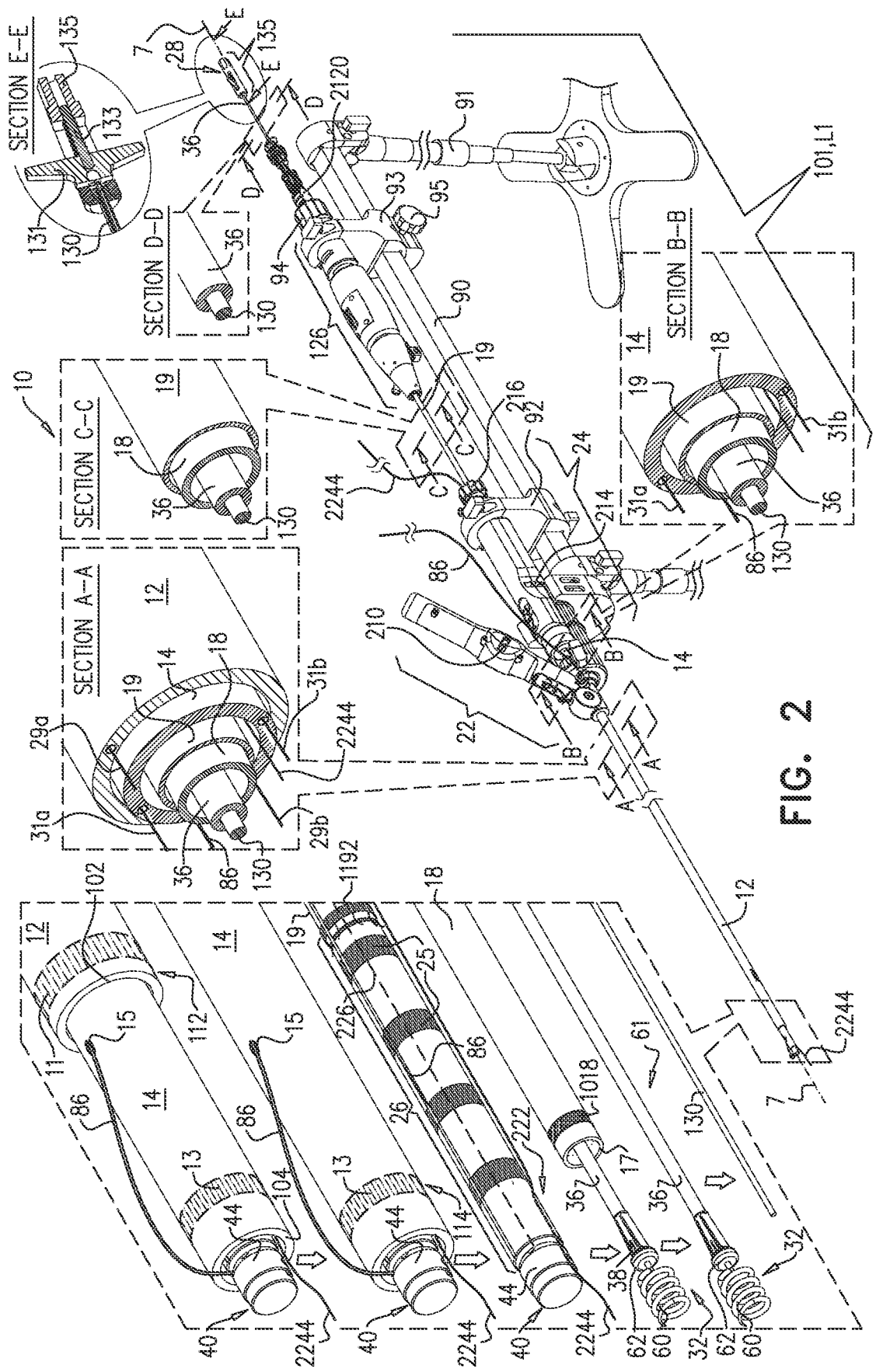
FIG. 2 is a schematic illustration of a multi-component tubular system for delivering and anchoring an implant and for controlling a relative spatial orientation of components of the catheter system, in accordance with some applications of the present invention.

Reference is now made to FIGS. 1-2, which are schematic illustrations of a multi-component tubular system 10 providing one or more rotationally-controlled steering catheters configured for delivering an implant to a heart of a subject, in accordance with some applications of the present invention.

FIG. 1 shows a distal portion of an implant that comprises an annuloplasty ring structure 222 (i.e., an implant, e.g., an annuloplasty band) comprising a flexible sleeve 26 (shown in the exploded view of FIG. 2). Sleeve 26 typically comprises a braided fabric mesh, e.g., comprising polyethylene terephthalate (such as Dacron™). Sleeve 26 is typically configured to be placed only partially around a cardiac valve annulus (i.e., to assume a C-shape), and, once anchored in place, to be contracted so as to circumferentially tighten the valve annulus. Alternatively, the ring structure is configured to be placed entirely around the valve annulus.

Sleeve 26 has (a) a tubular lateral wall 253 that (i) circumscribes a central longitudinal axis of the sleeve, and (ii) defines the lumen of the sleeve, and (a) at least one end wall 251 (e.g., a distal end wall) having a surface that is substantially transverse to a lateral surface of tubular wall 253. Typically, end wall 251 defines an end wall of annuloplasty ring structure 222.

In order to tighten the annulus, annuloplasty ring structure 222 comprises a flexible elongated contraction member 226 that extends along sleeve 26. Elongated contraction member 226 comprises a wire, a ribbon, a rope, or a band, which typically comprises a flexible and/or superelastic material, e.g., nitinol, polyester, stainless steel, or cobalt chrome. For some applications, the wire comprises a radiopaque material. For some applications, contraction member 226 comprises a braided polyester suture (e.g., Ticron). For some applications, contraction member 226 is coated with polytetrafluoroethylene (PTFE). For some applications, contraction member 226 comprises a plurality of wires that are intertwined to form a rope structure.

Annuloplasty ring structure 222 further comprises an adjustment mechanism 40, which facilitates contracting and expanding of annuloplasty ring structure 222 so as to facilitate adjusting of a perimeter of the annulus and leaflets of the cardiac valve. Adjustment mechanism 40 is described in more detail hereinbelow. Adjustment mechanism 40 comprises a rotatable structure (e.g., a spool, as described hereinbelow) that is disposed within a housing 44. For some applications of the present invention, adjustment mechanism 40 comprises the housing 44. Adjustment mechanism 40 may be surrounded by a braided mesh, coupled (e.g., by being sutured or otherwise coupled) to the braided mesh of sleeve 26. For some applications, adjustment mechanism 40 is coupled to an outer, lateral surface of sleeve 26.

Reference is now made to FIG. 2, which shows the concentric relationship between components of tubular system 10 (in an exploded view on the left side of FIG. 2). System 10 comprises an implant-delivery tool. Typically, system 10 comprises a first, outer catheter 12 comprising a sheath configured for transluminal advancement through vasculature of a subject. For some applications of the present invention, outer catheter 12 comprises a sheath configured for advancement through a femoral artery toward an interatrial septum of a heart of a subject. A distal end portion 112 of outer catheter 12 is configured to pass through the transatrial septum of the subject, and to be oriented in a desired spatial orientation within the left atrium. System 10 comprises a second catheter, or guide catheter 14, comprising a distal end portion 114 that is configured to pass through catheter 12 (i.e., a primary lumen thereof), to become disposed outside of a distal end 102 of the outer catheter, and to be oriented in a desired spatial orientation within the left atrium.

Distal end portion 112 of outer catheter 12 is steerable. That is, distal end portion 112 is deflectable with respect to an immediately more proximal portion of catheter 12 (e.g., by using extracorporeal elements of system 10). Distal end portion 112 comprises a pull ring 11 that is coupled to two or more pull wires 29a and 29b, that are disposed within respective secondary lumens within a lateral wall of catheter 12 (as shown in section A-A of FIG. 2). As shown in the exploded view, guide catheter 14 is configured to be concentrically disposed within the lumen of catheter 12. Distal end portion 114 of inner catheter 14 is steerable. That is, distal end portion 114 is deflectable with respect to an immediately more proximal portion of catheter 14 (e.g., by using extracorporeal elements of system 10). Distal end portion 114 comprises a pull ring 13 that is coupled to two or more pull wires 31a and 31b, that are disposed within respective secondary lumens within a wall of catheter 14 (as shown in sections A-A and B-B).

Guide catheter 14 is steerable to a desired spatial orientation in order to facilitate advancing and implantation of an implant in a body cavity of the subject.

For applications in which system 10 is used to deliver an implant to the mitral valve of the subject, typically, outer catheter 12 is configured for initial advancement through vasculature of the subject until a distal end 102 of catheter 12 is positioned in the left atrium. The distal steerable end portion of catheter 12 is then steered such that distal end 102 of catheter 12 is positioned in a desired spatial orientation within the left atrium. The steering procedure is typically performed with the aid of imaging, such as fluoroscopy, transesophageal echo, and/or echocardiography. Following the steering of the distal end portion of catheter 12, guide catheter 14 (which houses annuloplasty ring structure 222) is advanced through catheter 12 in order to facilitate delivery and implantation of structure 222 along the annulus of the mitral valve. During the delivery, at least a portion of steerable distal end portion 114 is exposed from distal end 102 of catheter 12 and is thus free for steering toward the annulus of the mitral valve, as is described hereinbelow.

During delivery of sleeve 26 to the annulus of the cardiac valve, sleeve 26 and mechanism 40 are disposed within a lumen of catheter 14 and are typically aligned longitudinally with a longitudinal axis of catheter 14. Mechanism 40 is coupled to sleeve 26 in a manner that allows mechanism 40 to move (e.g., to translate) from a state in which it is in line with the longitudinal axis of catheter 14 (FIG. 2) to a state in which it is disposed alongside sleeve 26 (FIG. 1). For example, adjustment mechanism 40 may be coupled to sleeve 26 via one or more connectors 27, such as sutures, which provide flexible and/or articulated coupling. For some applications, the positioning of adjustment mechanism 40 alongside a portion of sleeve 26 exposes a driving interface of the rotational structure (e.g., a driving interface 476, FIG. 16A), providing access to the interface for an adjustment tool that is subsequently guided toward adjustment mechanism 40 via a guide member 86.

Reference is again made to FIG. 1. A flexible, longitudinal guide member 86 (e.g., a wire) is coupled to a portion of adjustment mechanism 40 (e.g., a portion of the rotatable structure, as described hereinbelow). Guide member 86 has a thickness of 0.35-0.45 mm, e.g., 0.4 mm. Guide member 86 is configured to facilitate guiding of an adjustment tool via guide member 86 and toward the rotatable structure of adjustment mechanism 40. Typically, the adjustment tool is configured to engage the rotatable structure of adjustment mechanism 40 following implantation of sleeve 26 along the annulus of the cardiac valve. Guide member 86 extends from adjustment mechanism 40, alongside a portion of distal end portion 114 of guide catheter 14, and into a secondary lumen in the wall of guide catheter 14 via an opening 15 in guide catheter 14. Guide member 86 extends through the secondary lumen of guide catheter 14 (as shown in sections A-A and B-B in FIG. 2) and has a proximal end that is accessible from outside the body of the subject. The secondary lumen in the wall of guide catheter 14 facilitates passage of guide member 86 through system 10 without interfering with the other concentrically-disposed elongate tubular members that pass concentrically through the lumen of guide catheter 14.

Reference is again made to FIG. 2. In addition, system 10 comprises a plurality of anchors 32, typically between about 5 and about 20 anchors, such as about 10 or about 16 anchors. Each anchor 32 comprises a tissue-coupling element 60 (e.g., a helical tissue-coupling element), and a tool-engaging head 62 (e.g., a non-helically-shaped portion), fixed to one end of the tissue-coupling element. Only one anchor 32 is shown in FIG. 2 as being reversibly coupled to a deployment element 38 of an anchor driver 36 of an anchor deployment manipulator 61. However, each of anchors 32 is reversibly couplable to a deployment element 38 of one or more anchor drivers 36. When sleeve 26 is disposed along the annulus of the cardiac valve, deployment manipulator 61 is configured to advance within a lumen of sleeve 26 and deploy each anchor 32 from within sleeve 26 through a wall of sleeve 26 and into cardiac tissue, thereby anchoring sleeve 26 around a portion of the valve annulus. The insertion of the anchors into the sleeve and deployment of the anchors into cardiac tissue is described in detail hereinbelow.

Typically, but not necessarily, anchors 32 comprise a biocompatible material such as stainless steel 316 LVM. For some applications, anchors 32 comprise nitinol. For some applications, anchors 32 are coated fully or partially with a non-conductive material.

Deployment manipulator 61 comprises anchor driver 36 and deployment element 38.

For some applications, deployment manipulator 61 comprises channel 18.

As shown in the exploded view of FIG. 2, sleeve 26 is disposed within a lumen of guide catheter 14. Forces are applicable to a proximal end of sleeve 26 via a reference-force tube 19, a distal end of which is coupled to the proximal end of the sleeve. As shown, an implant-decoupling channel 18 is advanceable within a lumen of reference-force tube 19 and within a lumen of sleeve 26. As shown in the enlarged image of FIG. 1, a distal end 17 of implant-decoupling channel 18 is placeable in contact with an inner wall of sleeve 26, e.g., at a distal end thereof. The distal end portion of channel 18 may comprise a radiopaque marker 1018. As shown, tube 19 and sleeve 26 are longitudinally and coaxially disposed with respect to each other.

For some applications, channel 18 is steerable.

Typically, manipulator 61 advances within channel 18. For some applications, system 10 comprises a plurality of anchor drivers 36 of manipulator 61, each driver 36 being coupled to a respective anchor 32. Each driver 36 is advanced within channel 18 in order to advance and implant anchor 32 in tissue. Following implantation of anchor 32, anchor 32 is decoupled from driver 36, as described herein, and driver 36 is removed from within channel 18. A subsequent anchor 32 is then advanced within channel 18 while coupled to a driver 36 (e.g., a new driver).

As will be described hereinbelow, a first one of anchors 32 is configured to be deployed through end wall 251 of sleeve 26 into cardiac tissue, when sleeve 26 is positioned along the annulus of the valve. Following the deployment of the first tissue anchor, a distal portion of sleeve 26 is slid distally off a portion of implant-decoupling channel 18. In order to decouple sleeve 26 distally from a portion of outer surface of channel 18, (1) a proximal force is applied to channel 18, while (2) reference-force tube 19 is maintained in place in a manner in which a distal end of tube 19 provides a reference force to sleeve 26, thereby facilitating freeing of a successive portion of sleeve 26 from around channel 18. Channel 18 is then positioned at a successive location within the lumen of sleeve 26 while tube 19 and/or catheter 14 is steered toward a successive location along the annulus of the valve (as will be described hereinbelow). Consequently, the successive portion of sleeve 26 provides a free lumen for advancement of a successive anchor 32 and deployment of the anchor through the wall of the sleeve at the successive portion thereof. Such freeing of the successive portion of sleeve 26 creates a distance between successive anchors deployed from within the lumen of sleeve 26.

For some applications, sleeve 26 comprises a plurality of radiopaque markers 25, which are positioned along the sleeve at respective longitudinal sites. The markers may provide an indication in a radiographic image (such as a fluoroscopy image) of how much of the sleeve has been deployed at any given point during an implantation procedure, in order to enable setting a desired distance between anchors 32 along the sleeve. For some applications, the markers comprise a radiopaque ink.

Typically, at least some (e.g., at least three, such as all) of the longitudinal sites are longitudinally spaced at a constant interval. Typically, the longitudinal distance between the distal edges of adjacent/consecutive markers, and/or the distance between the proximal edges of adjacent markers, is set equal to the desired distance between adjacent anchors. For example, the markers may comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

Each anchor 32 is coupled to deployment element 38 of an anchor driver 36. Anchor driver 36 typically comprises an elongate and flexible shaft (which is typically tubular) having at least a flexible distal end portion. The elongate shaft of driver 36 extends within a lumen of channel 18, through system 10 toward a proximal end of a proximal handle portion 101 of system 10. The tube of anchor driver 36 provides a lumen for slidable advancement therethrough of an elongate rod 130. Rod 130 facilitates the locking and unlocking of anchor 32 to deployment element 38. As shown in Section E-E of FIG. 2, a proximal end of rod 130 is coupled to a component of an anchor-release mechanism 28 at a proximal end of system 10. Mechanism 28 comprises a housing 135 and a finger-engager 131 that is coupled to the proximal end of rod 130. Finger-engager 131 is coupled to a housing 135 via a spring 133 (section E-E of FIG. 2). A proximal end of the tube of anchor driver 36 is coupled to housing 135. The physician releases anchor 32 from deployment element 38 when finger-engager 131 is pulled proximally, thereby pulling rod 130 proximally.

Proximal handle portion 101 is supported by a stand having support legs 91 and a handle-sliding track 90. Handle portion 101 comprises an outer-catheter handle 22, a guide-catheter handle 24, an implant-manipulating handle 126, and anchor-release mechanism 28. Handle 22 is coupled to a proximal end of outer catheter 12. Handle 24 is coupled to a proximal portion of guide catheter 14. Handle 126 is coupled to a proximal portion of reference-force tube 19, and linear movement of handle 126 with respect to handle 24 moves reference-force tube 19 (and thereby typically structure 222) through catheter 14. As described hereinabove, housing 135 of anchor-release mechanism 28 is coupled to a proximal portion of the tube of anchor driver 36. The relative positioning of each of the concentrically-disposed components of system 10 is shown in the exploded view and sections A-A, B-B, C-C, and D-D of FIG. 2.

The stand supporting proximal handle portion 101 may be moved distally and proximally to control a position of the entire multi-component system 10, particularly so as to adjust a distance of distal end 102 of catheter 12 from the interatrial septum. Handle 22 comprises a steering knob 210 that is coupled to steering wires 29a and 29b disposed within respective secondary lumens in the wall of outer catheter 12. Rotation of knob 210 adjusts a degree of tension of wires 29a and 29b which, in turn, apply a force to pull ring 11 at the distal end portion of outer catheter 12. Such force steers the distal end portion of catheter 12 within the atrium of the heart of the subject in a manner in which the distal end portion of catheter 12 is steered in a first steering plane that is typically parallel with the plane of the annulus of the valve (e.g., in a direction from the interatrial septum toward surrounding walls of the atrium). For some applications of the present invention, the distal end portion of catheter 12 may be pre-shaped so as to point downward toward the valve. For other applications, the distal end portion of catheter 12 may be pulled to assume an orientation in which the distal end portion points downward toward the valve. For yet other applications of the present invention, the distal end portion of catheter 12 is not made to point downward toward the valve.

Handle 24 is coupled to track 90 via a first mount 92. Mount 92 is slidable proximally and distally along track 90 in order to control an axial position of guide catheter 14 with respect to outer catheter 12. Mount 92 is slidable via a control knob 216. For example, control knob 216 of mount 92 controls the proximal and distal axial movement of the distal steerable portion of guide catheter 14 with respect to distal end 102 of outer catheter 12. Handle 24 comprises a steering knob 214 that is coupled to steering wires 31a and 31b disposed within respective secondary lumens in the wall of guide catheter 14. Rotation of knob 214 adjusts a degree of tension of wires 31a and 31b which, in turn, apply a force to pull ring 13 at the distal end portion of guide catheter 14. Such force steers the distal end portion of catheter 14 in a second steering plane within the atrium of the heart of the subject, typically downward and toward the annulus of the cardiac valve. Typically, as described hereinbelow, the distal end portion of guide catheter 14 is steered in the second plane that is substantially perpendicular with respect to the first plane in which the distal end portion of outer catheter 12 is steered.

The combined steering of the respective distal end portions of catheters 12 and 14 directs sleeve 26 down toward the annulus (e.g., via the steering of the distal end portion of catheter 14) and along the perimeter of annulus (e.g., from the posterior section of the valve to the anterior section of the valve, and vice versa), via the steering of the distal end portion of catheter 12.

For some applications, handle 22 may be tilted by the operating physician, in order to further adjust a position of the distal end of catheter 12.

Handle 126 is slidably coupled to track 90 via a second mount 93. Mount 93 is slidable proximally and distally along track 90, in order to control an axial position of reference-force tube 19 and at least a proximal portion of sleeve 26 with respect to guide catheter 14. For some applications, mount 93 comprises a control knob 95. For some such applications, control knob reversibly locks mount 93 to track 90, thereby reversibly inhibiting sliding of the mount along the track. Alternatively or additionally, turning of control knob 95 may cause sliding of mount 93 along track 90 (e.g., acting like a rack and pinion). For some applications, friction between (i) reference-force tube 19 and (ii) catheter 14 and/or handle 24 reduces a likelihood of inadvertent sliding of tube 19 through catheter 14, and thereby obviates the need for locking of mount 93 to track 90. Taken together with the steering of the distal end portion of guide catheter 14, such movement of tube 19 and at least the proximal portion sleeve 26 moves the proximal portion of sleeve 26 toward a desired portion of tissue of the annulus of the valve during deployment of anchors 32 from within the lumen of sleeve 26, as is described hereinbelow.

As is described hereinabove, in order to decouple sleeve 26 from a portion of an outer surface of channel 18, (1) channel 18 is pulled proximally, while (2) reference-force tube 19 is maintained in place. A proximal end of channel 18 is coupled to a knob 94 which adjusts an axial position of channel 18 proximally and distally with respect to reference-force tube 19 and sleeve 26.

Typically, handle portion 101 comprises a release-decision-facilitation member 127, such as a latch or button, that automatically engages when a given length of sleeve 26 has advanced off channel 18 (e.g., when channel 18 is at a given position with respect to tube 19); typically just before sleeve 26 becomes completely decoupled from channel 18. Engagement of member 127 inhibits proximal movement of channel 18 with respect to tube 19, thereby reducing a likelihood of (e.g., preventing) inadvertent release of sleeve 26. In order to release sleeve 26 (e.g., to decouple channel 18 from the sleeve), the operating physician must disengage member 127, such as by pushing the button, before continuing to withdraw channel 18 proximally. Typically, when engaged, member 127 also inhibits distal movement of channel 18 with respect to tube 19.

Handle portion 101 (comprising handles 22, 24, and 126 and anchor-release mechanism 28) has a length L1 of between 65 and 85 cm, e.g., 76 cm. Typically, as shown, a majority of the body portion of outer-catheter handle 22 is disposed at a non-zero angle with respect to a longitudinal axis 7 of the multiple components of system 10. The steering mechanism provided by handle 22 in order to steer the distal end portion of catheter 12 is disposed within the portion of handle 22 that is disposed at the non-zero angle with respect to axis 7. Handle 22 comprises an in-line tubular portion which is longitudinally disposed in-line along axis 7 and coaxially with respect to handles 24 and 126 and release mechanism 28. The in-line tubular portion is shaped so as to define a lumen for inserting guide catheter 14 therethrough and subsequently into the lumen of outer catheter 12. The in-line tubular portion has a length L24 of between 7 and 11 cm, e.g., 7 cm. Such spatial orientation of the majority of handle 22 at an angle with respect to axis 7 reduces an overall functional length of handle portion 101.

Typically, but not necessarily, a guidewire 2244 extends alongside sleeve 26 to facilitate positioning of sleeve 26 along the annulus.

Reference is made to FIGS. 3A-G, and 4A-B, which are schematic illustrations of steps in the implantation of an annuloplasty ring structure to repair a mitral valve, in accordance with some applications of the invention. This procedure is one exemplary procedure that can be performed using system 10.

Anchor deployment manipulator 61 is advanced into a lumen of sleeve 26, and, from within the lumen, deploys the anchors through a wall of the sleeve and into cardiac tissue, thereby anchoring the sleeve around a portion of the valve annulus. For some application, annuloplasty ring structure 222 is implemented using techniques described in U.S. application Ser. No. 12/437,103, filed May 7, 2009 which published as US 2010/0286767, and/or U.S. application Ser. No. 12/689,635, filed Jan. 19, 2010 which published as US 2010/0280604, both of which are assigned to the assignee of the present application and are incorporated herein by reference. As described hereinabove, annuloplasty ring structure 222 comprises adjustment mechanism 40. The adjustment mechanism comprises a rotatable structure, such as a spool, arranged such that rotation of the rotatable structure contracts the implant structure. The implant further comprises a longitudinal member, such as a wire, which is coupled to the adjustment mechanism. An adjustment tool is provided for rotating the rotatable structure. The tool is configured to be guided along (e.g., over, alongside, or through) the longitudinal member, to engage the rotatable structure, and to rotate the rotatable structure in response to a rotational force applied to the tool.

The procedure typically begins by advancing a semi-rigid guidewire into a right atrium 220 of the subject. The procedure is typically performed with the aid of imaging, such as fluoroscopy, transesophageal echo, and/or echocardiography.

The guidewire provides a guide for the subsequent advancement of outer catheter 12 therealong and into the right atrium. Once a distal portion of catheter 12 has entered the right atrium, the guidewire is retracted from the subject's body. Catheter 12 typically comprises a 14-24 F sheath, although the size may be selected as appropriate for a given subject. Catheter 12 is advanced through vasculature into the right atrium using a suitable point of origin typically determined for a given subject. For example:

- catheter 12 may be introduced into the femoral vein of the subject, through an inferior vena cava 223, into right atrium 220, and into a left atrium 224 transseptally, typically through the fossa ovalis;
- catheter 12 may be introduced into the basilic vein, through the subclavian vein to the superior vena cava, into right atrium 220, and into left atrium 224 transseptally, typically through the fossa ovalis; or
- catheter 12 may be introduced into the external jugular vein, through the subclavian vein to the superior vena cava, into right atrium 220, and into left atrium 224 transseptally, typically through the fossa ovalis.

For some applications of the present invention, catheter 12 is advanced through inferior vena cava 223 of the subject (as shown) and into right atrium 220 using a suitable point of origin typically determined for a given subject.

Catheter 12 is advanced distally until the sheath reaches the interatrial septum, and the guidewire is withdrawn.

A resilient needle and a dilator are advanced through catheter 12 and into the heart. In order to advance catheter 12 transseptally into left atrium 224, the dilator is advanced to the septum, and the needle is pushed from within the dilator and is allowed to puncture the septum to create an opening that facilitates passage of the dilator and subsequently catheter 12 therethrough and into left atrium 224. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum. A distal-most end 102 of catheter 12 is tapered so as to facilitate passage of at least part of distal portion 112 of catheter 12 through the opening in the septum.

The advancement of catheter 12 through the septum and into the left atrium is followed by the extraction of the dilator and the needle from within catheter 12. Once distal portion 112 of catheter 12 is disposed within atrium 224, portion 112 is steered (i.e., deflected) in a first steering plane, typically parallel to a plane of the annulus of mitral valve 230. The steering of the distal portion of catheter 12 is performed via steering knob 210 of handle 22 in handle portion 101 (in FIG. 2).

As shown in FIG. 3A, catheter 14, containing annuloplasty ring structure 222 (with a distal portion of channel 18 disposed within sleeve 26 thereof), is advanced through catheter 12 into left atrium 224. For some applications, soon before implantation (e.g., within the operating theater or in an adjacent room) the distal portion of channel 18 is loaded into sleeve 26, and structure 222 is loaded into catheter 14. Distal end portion 114 of catheter 14 extends beyond distal end 102 of catheter 12. Distal end portion 114 is then steered (i.e., deflected) in a second steering plane, typically perpendicular with respect to the steering plane of catheter 12, and further typically toward the annulus of valve 230. The steering of the distal portion of catheter 14 is performed via steering knob 214 of handle 24 in handle portion 101 (in FIG. 2).

FIG. 3A shows annuloplasty ring structure 222, comprising sleeve 26 and adjustment mechanism 40, having been advanced, via catheter 14, to a mitral valve 230. As shown in FIG. 3A, and as described hereinabove, during advancement of structure 222, adjustment mechanism 40 is disposed distal to (i.e., in front of) sleeve 26. In this way, adjustment mechanism 40 is disposed on the longitudinal axis of sleeve 26 (e.g., collinearly with the sleeve), so as to advantageously maintain a small cross-sectional diameter of the implant for transluminal delivery. A proximal end of connector 27 is disposed proximally to mechanism 40 (e.g., by being fixed to a portion of sleeve 26 proximal to mechanism 40 or by being accessible outside the body of the subject). A distal end of connector 27 is coupled (e.g., by being fixedly coupled by a knot or other mechanical coupling) to mechanism 40. Guide member 86, described hereinabove, typically extends distally from catheter 14, between end wall 251 of sleeve 26 and adjustment mechanism 40, and there is coupled to the adjustment mechanism. For some applications it is advantageous to (1) advance the structure to the mitral valve while mechanism 40 is disposed on the longitudinal axis of sleeve 26 (e.g., collinearly with the sleeve), so as to maintain a small cross-sectional diameter of the structure for transluminal delivery; and (2) to subsequently move mechanism 40 away from the longitudinal axis, e.g., so as to allow end wall 251 of the sleeve to be placed against the annulus, and/or so as to allow an anchor to be driven through the end wall of the sleeve. Connectors 27 facilitate this technique by making mechanism 40 flexibly and/or articulatably coupled to sleeve 26. For some applications, connectors 27 are tensioned or relaxed to move mechanism 40 with respect to sleeve 26 to reposition mechanism 40. For some applications, guide member 86 is tensioned or relaxed in order to reposition mechanism 40.

Figure 3B:
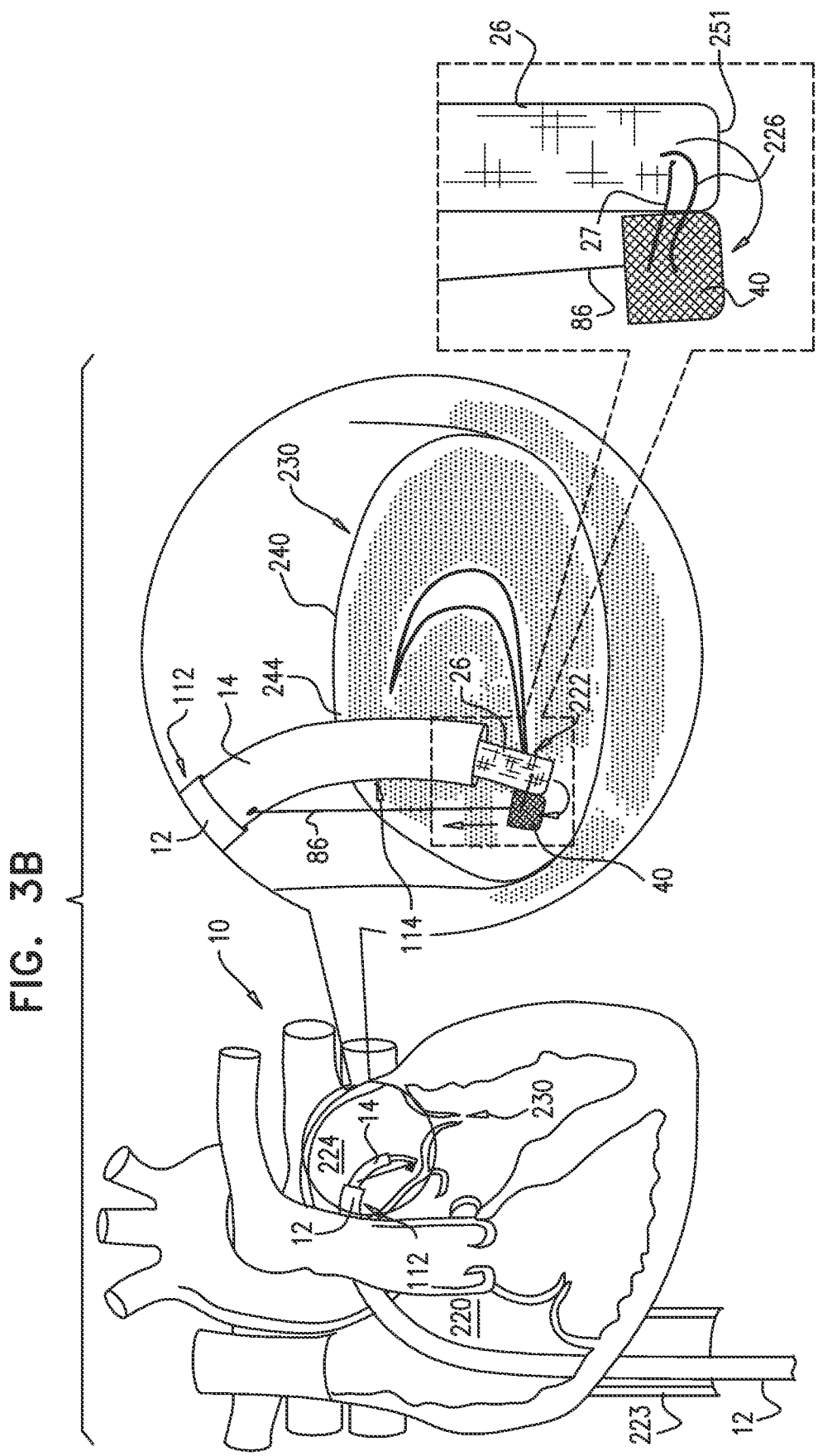

Subsequent to exposure of at least adjustment mechanism 40 (and typically at least end wall 251 of sleeve 26) from catheter 14, the adjustment mechanism is moved away from end wall 251. Typically, this is achieved by guide member 86 being moved proximally such that mechanism 40 moves (e.g., translates, deflects, and/or rotates) away from the longitudinal axis of the sleeve, typically to become disposed laterally from sleeve 26. FIG. 3B shows mechanism 40 having translated to such a position. The movement of mechanism 40 away from end wall 251 of sleeve 26 advantageously allows end wall 251 of sleeve 26 to be placed against an atrial surface of an annulus 240, and a first one of anchors 32 to be driven through end wall 251 of the sleeve and into the annulus (FIG. 3C).

Figure 3C:
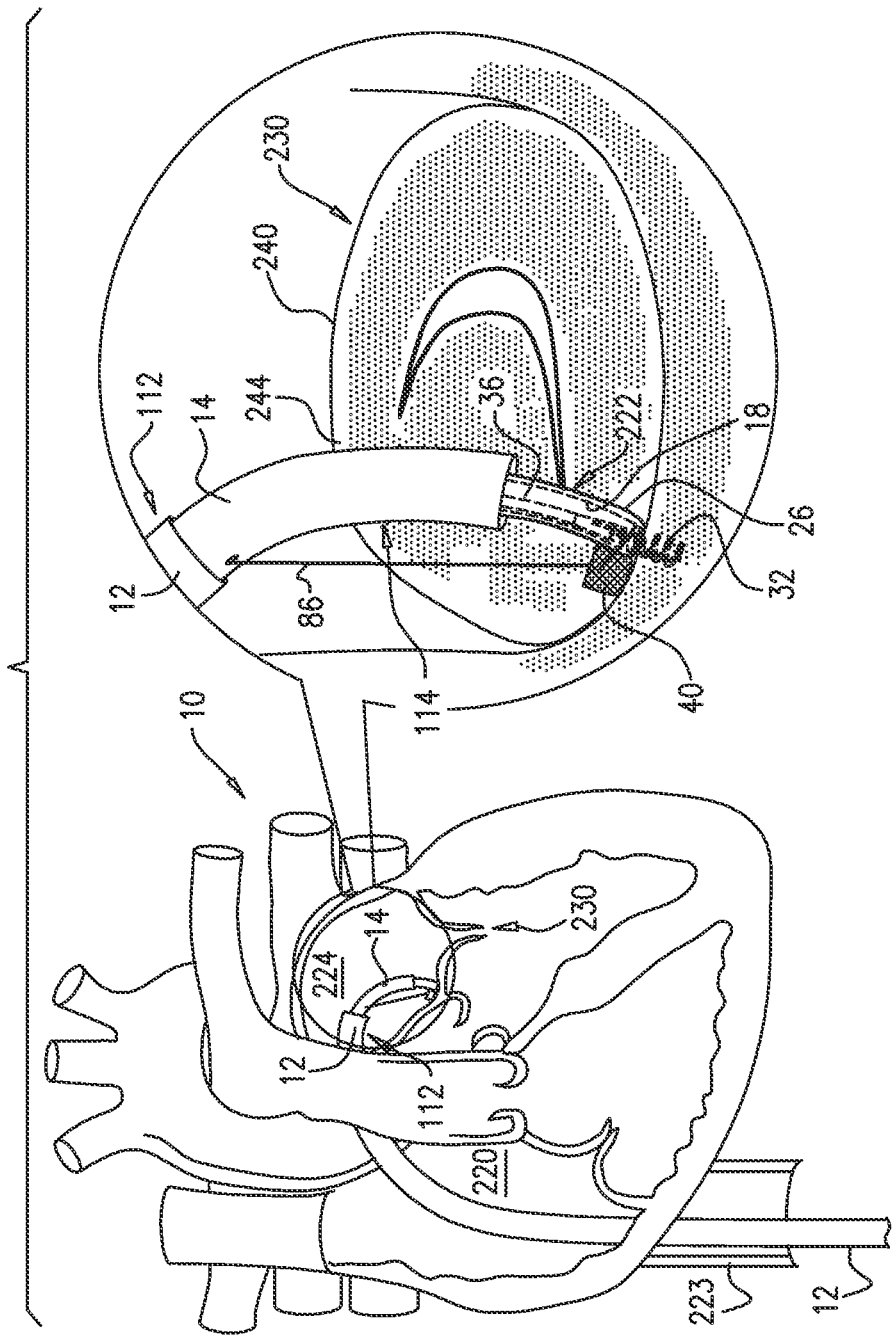

As shown in FIG. 3C, end wall 251 of sleeve 26 is positioned in a vicinity of a left fibrous trigone 242 of an annulus 240 of mitral valve 230. (It is noted that for clarity of illustration, distal end wall 251 of sleeve 26 is shown schematically in the cross-sectional view of the heart, although left trigone 242 is in reality not located in the shown cross-sectional plane, but rather out of the page closer to the viewer.) Alternatively, the distal end of sleeve 26 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site near the selected trigone, deployment manipulator 61 deploys the first one of anchors 32 through the wall of sleeve 26 (by penetrating and passing through the wall of the sleeve (i) in a direction parallel to a central longitudinal axis of deployment manipulator 61, or anchor driver 36, through the distal end of channel 18, and/or (ii) parallel to a central longitudinal axis of tissue-coupling element 60 of anchor 32) into cardiac tissue near the trigone. Following the deployment of anchor 32 in the cardiac tissue, deployment element 38 is decoupled from anchor 32.

Anchors 32 are typically deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the atrial surface of the cardiac tissue in a direction parallel to the central longitudinal axis through the distal end of manipulator 61. Such an angle is typically provided and/or maintained by channel 18 being more rigid than sleeve 26. Distal end 17 of channel 18 is typically brought close to the surface of the cardiac tissue (and the wall of sleeve 26 that is disposed against the surface of the cardiac tissue), such that little of each anchor 32 is exposed from channel 18 before penetrating the sleeve and the tissue. For example, distal end 17 of channel 18 may be placed (e.g., pushed) against the wall of the sleeve, sandwiching the sleeve against the cardiac tissue.

For some applications, such placement of distal end 17 of channel 18 against the cardiac tissue (via the wall of the sleeve), stabilizes the distal end during deployment and anchoring of each anchor 32, and thereby facilitates anchoring. For some applications, pushing of distal end 17 against the cardiac tissue (via the wall of the sleeve) temporarily deforms the cardiac tissue at the site of contact. This deformation may facilitate identification of the site of contact using imaging techniques (e.g., by identifying a deformation in the border between cardiac tissue and blood), and thereby may facilitate correct positioning of the anchor.

That is, typically the entire circular surface of distal end 17 of channel 18 is disposed in contact with the wall of sleeve 26 that is disposed against the surface of the cardiac tissue. As shown, distal end 17 is the lower-most circular tip of channel 18 and defines a distal opening of channel 18. In the configuration in which channel 18 is positioned in order to sandwich the portion of sleeve 26 against annulus 240, the distal end 17 is disposed in parallel with a planar surface 255 of the tissue of the annulus.

As shown in FIG. 3C, end wall 251 aligns against the tissue of annulus 240 in a manner in which a surface of end wall 251 is disposed in parallel with a planar surface of the tissue of annulus 240. Additionally, distal end 17 of implant-decoupling channel 18 flattens end wall 251 against the tissue of annulus 240 in a manner in which channel 18 sandwiches end wall 251 between (1) distal end 17 of the channel, and (2) the portion of the tissue of annulus 240 at the planar surface into which a first one of anchors 32 is implanted. In such a manner, end wall 251 lies flat against the tissue of annulus 240 in parallel with the planar surface, while at least a distal portion of lateral wall 253 is disposed substantially perpendicularly with respect to the portion of the tissue of annulus 240 at the planar surface into which the first one of anchors 32 is implanted.

As shown, anchor 32 is implanted using channel 18 and manipulator 61 contained within sleeve 26 of annuloplasty structure 222 while at least a portion of annuloplasty structure 222 (e.g., a proximal portion) is contained within surrounding catheter 14.

Figure 3D:
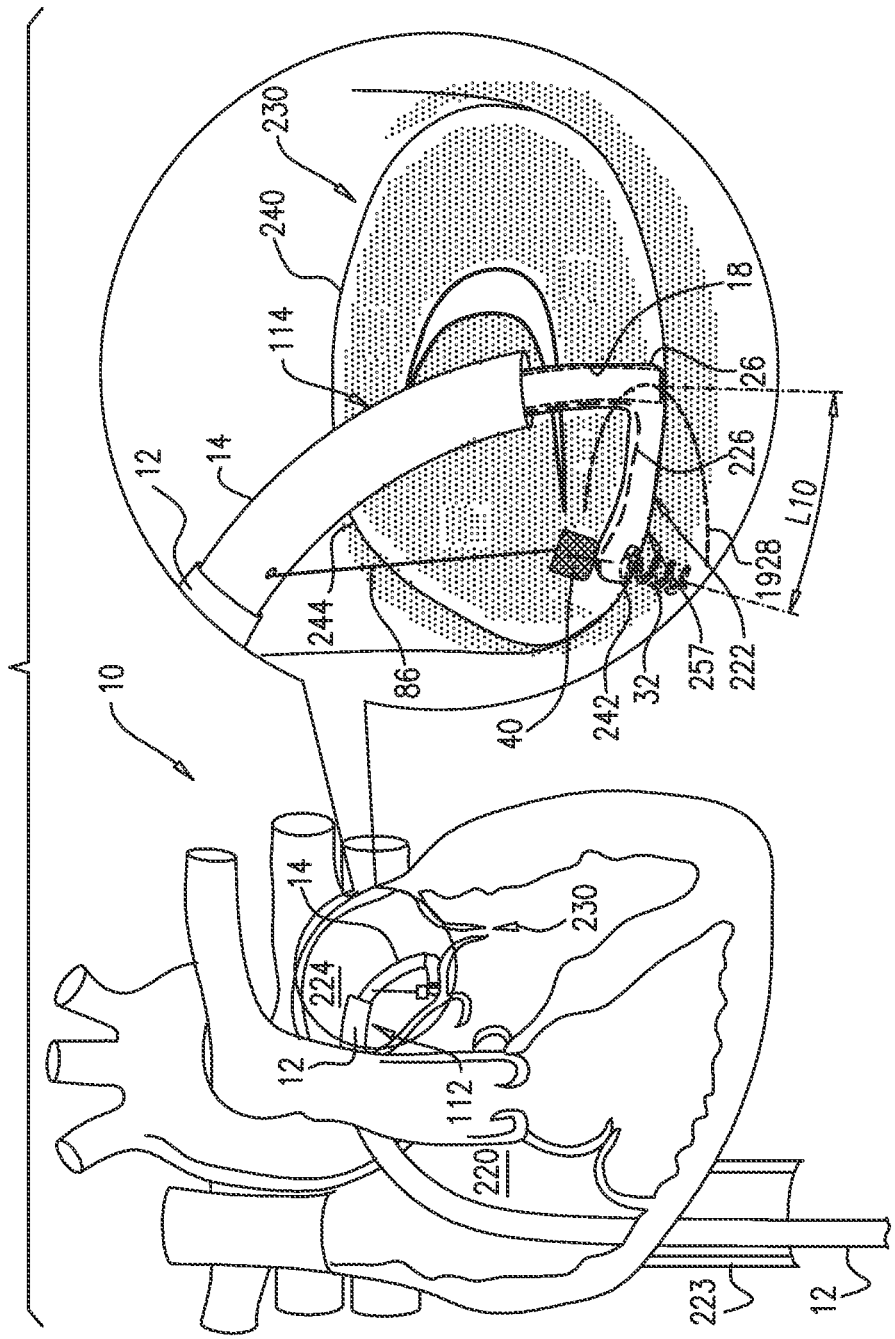

Reference is now made to FIGS. 2, 3C-D, and 4A-B. Following the deployment of the first tissue anchor, a distal portion of sleeve 26 is decoupled from a portion of implant-decoupling channel 18. In order to decouple the portion of sleeve 26 from outer surface of channel 18, (1) channel 18 is pulled proximally, while (2) reference-force tube 19 is maintained in place in a manner in which a distal end of tube 19 provides a reference force to sleeve 26 in order to facilitate freeing of a successive portion of sleeve 26 from around channel 18. In order to decouple sleeve 26 from the outer surface of channel 18, (1) channel 18 is pulled proximally, while (2) reference-force tube 19 is maintained in place. An indicator 2120 on handle 126 provides an indication of how much channel 18 is withdrawn from within sleeve 26 (i.e., how much the delivery tool is decoupled from sleeve 26, and how much the sleeve has advanced off channel 18 and against tissue). A proximal end of channel 18 is coupled to a knob 94 (FIG. 2) which adjusts an axial position of channel 18 proximally and distally with respect to reference-force tube 19 and sleeve 26. As shown in FIG. 3D, once the successive portion of sleeve 26 is freed, deployment manipulator 61 is repositioned along annulus 240 to another site selected for deployment of a second one of anchors 32.

Figure 4B:
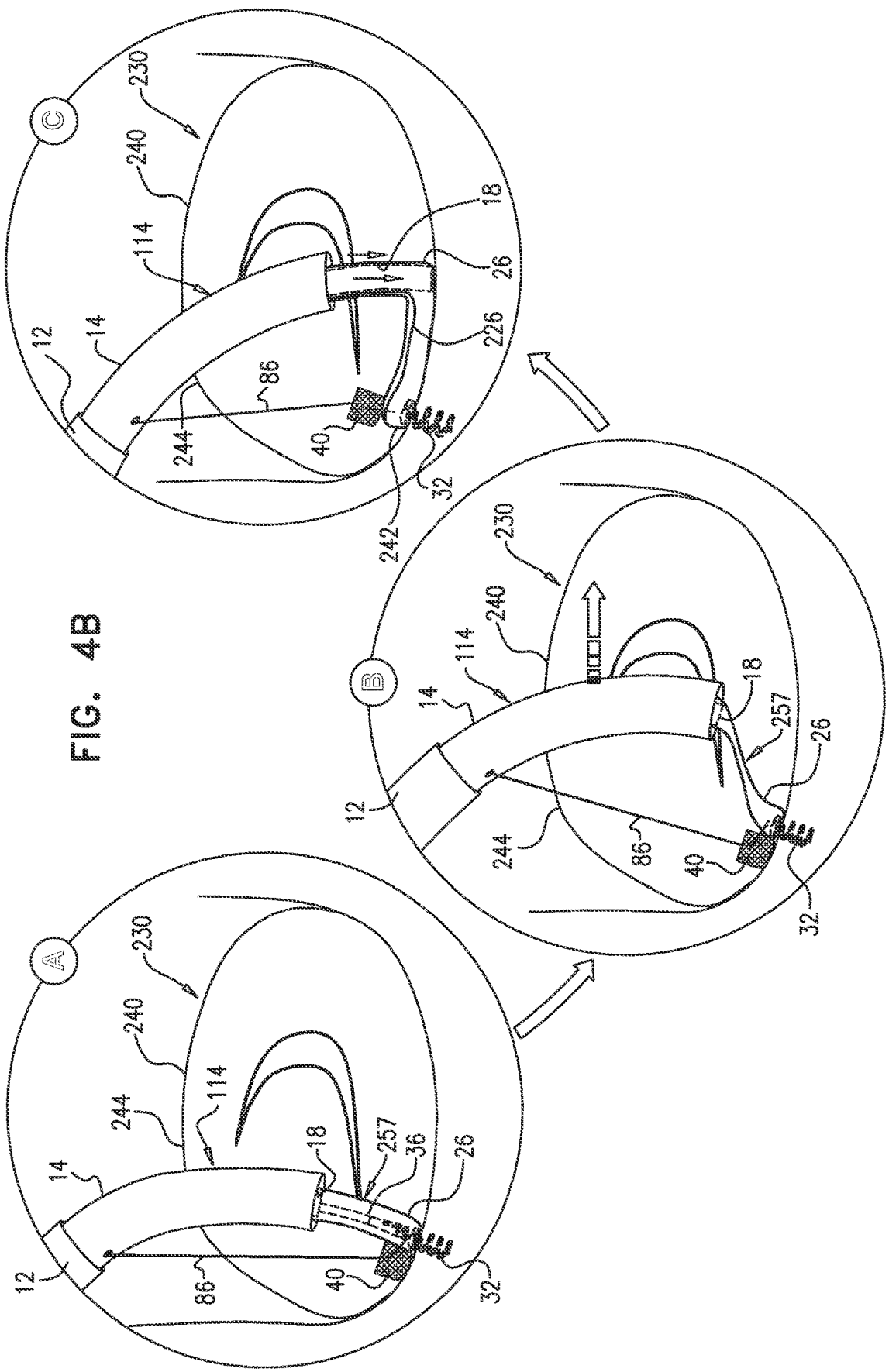

FIGS. 4A and 4B are schematic illustrations that show steps between the state shown in FIG. 3C and the state shown in FIG. 3D, in accordance with respective applications of the invention. Step C of each of FIGS. 4A and 4B shows a state that is generally equivalent to the state shown in FIG. 3D.

For some applications, and as shown in FIG. 4A, anchor driver 36 is decoupled from anchor 32 and is retracted through channel 18 prior to retracting channel 18 through sleeve 26 and repositioning channel 18.

For some applications, and as shown in FIG. 4B, anchor driver 36 remains coupled to anchor 32 during the retraction of channel 18 though sleeve 26. For some such applications, anchor driver 36 provides a reference force (e.g., a distally-directed reference force) that holds in place anchor 32 and the anchored portion of sleeve 26 while channel 18 is retracted, e.g., reducing a pulling force on anchor 32.

A method is therefore described, comprising: (1) percutaneously advancing toward a tissue of a subject structure 222, while a distal portion of channel 18 is disposed within the lumen defined by sleeve 26, such that a distal opening of the channel is disposed at a first portion of the sleeve; (2) anchoring the first portion of the sleeve to the tissue by using anchor driver 36 to drive tissue-coupling element 60 of a first anchor 32 through the distal opening of the channel, through the sleeve, and into the tissue; (3) subsequently, while providing a distally-directed reference force to the first anchor 32 via driver 36, proximally withdrawing the distal portion of channel 18 such that the distal opening of the channel is disposed at a second portion of the sleeve; (4) subsequently, proximally withdrawing driver 36 through the channel; and (5) subsequently, anchoring the second portion of the sleeve to the tissue by driving tissue-coupling element 60 of a second anchor 32 through the distal opening of the channel, through sleeve 26, and into the tissue.

Reference is now made to FIGS. 2, 3D, and 4A-B. Such repositioning of manipulator 61 is accomplished by performing one or more of the following:
(1) steering distal end portion 112 of catheter 12 (e.g., by steering knob 210 of handle 22) in the first steering plane, in a manner that bends portion 112,
(2) steering distal end portion 114 of catheter 14 (e.g., by steering knob 214 of handle 24) in the second steering plane, in a manner that portion 112,
(3) axially moving catheter 14 with respect to catheter 12 via knob 216,
(4) axially moving the stand supporting handles 22 and 24 to move both catheters 12 and 14,
(5) moving tube 19 and sleeve 26 axially by sliding mount 93 along track 90,
(6) by moving channel 18 relative to tube 19 by actuating knob 94.

Typically, the first tissue anchor is deployed most distally in the sleeve (generally at or within a few millimeters of the distal tip of the sleeve), and each subsequent anchor is deployed more proximally, such that the sleeve is gradually decoupled from channel 18 of deployment manipulator 61 in a distal direction during the anchoring procedure (i.e., channel 18 is withdrawn from within sleeve 26, and handle 126 is moved distally so as to retract the tool to make the successive proximal portion sleeve 26 ready for implantation of a subsequent anchor). The already-deployed first one of anchors 32 holds the anchored end of sleeve 26 in place, so that the sleeve is drawn from the site of the first tissue anchor towards the site of the second tissue anchor. As sleeve 26 is drawn and decoupled from channel 18, a distal portion 257 of sleeve 26 (i.e., the portion of the sleeve that is proximal to end wall 251) is positioned in a vicinity of tissue of annulus 240.

FIG. 3D shows distal portion 257 of sleeve 26 (i.e., the portion of the sleeve that is proximal to end wall 251) having been decoupled from a portion of channel 18 by retracting channel 18 proximally. Depending on the tension applied between the first and second tissue anchor sites, the portion of sleeve 26 therebetween may remain tubular in shape, or may become flattened.

FIG. 3E shows a second tissue anchor 32 (shown as a second tissue anchor 32b) being deployed through a portion of lateral wall 253 of sleeve 26. The first one of anchors 32 deployed through end wall 251 is labeled as anchor 32a. Deployment manipulator 61 deploys the second tissue anchor by driving the anchor to penetrate and pass through the wall of sleeve 26 into cardiac tissue at the second site.

As shown, anchor 32b is implanted using channel 18 and manipulator 61 contained within sleeve 26 of annuloplasty structure 222 while at least a portion of annuloplasty structure 222 (e.g., a proximal portion) is contained within surrounding catheter 14.

As described hereinabove, anchors 32a and 32b are each deployed from a distal end of manipulator 61 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 32 are deployed from the distal end of manipulator 61 into the atrial surface of the cardiac tissue in a direction parallel to the central longitudinal axis through the distal end of manipulator 61. Such an angle is typically provided and/or maintained by channel 18 being more rigid than sleeve 26. Distal end 17 of channel 18 is typically brought close to the surface of the cardiac tissue (and the wall of sleeve 26 that is disposed against the surface of the cardiac tissue), such that little of anchor 32b is exposed from channel 18 before penetrating the sleeve and the tissue. For example, distal end 17 of channel 18 may be placed (e.g., pushed) against the wall of the sleeve, sandwiching the sleeve against the cardiac tissue.

As shown in FIGS. 3D-E, a portion of the lateral wall of sleeve 26 aligns against the tissue of in a manner in which a surface of the portion of the lateral wall is disposed in parallel with the planar surface of the tissue. Additionally, distal end 17 of channel 18 flattens the portion of the lateral wall against the tissue of annulus 240 in a manner in which channel 18 sandwiches the portion of the lateral wall between (1) distal end 17 of implant-decoupling channel, and (2) the portion of the tissue of annulus 240 at the planar surface into which second tissue anchor 32b is implanted. In such a manner, the portion of the lateral wall being anchored lies flat against the tissue of annulus 240 (parallel with the planar surface thereof), while the remaining portion of the tubular lateral wall is disposed substantially perpendicularly with respect to the portion of the tissue into which second tissue anchor 32b is implanted.

It is to be noted that first and second tissue anchors 32a and 32b extend in a substantially same direction and into a common, substantially planar surface of a valve annulus, despite that first tissue anchor 32a is deployed through end wall 251 of sleeve 26, and tissue anchor 32b is deployed through lateral wall 253 of the sleeve. For some applications, anchors 32a and 32b are disposed with respect to each other at an angle of between 0 and 45 degrees, e.g., between 0 and 30 degrees, e.g., between 0 and 20 degrees.

For some applications, a maximum distance L10 between first tissue anchor 32a and a point of anchoring of second tissue anchor 32b is provided by the length of sleeve 26 that has been decoupled from the portion of channel 18 (e.g., by the distance that channel 18 has been retracted from sleeve 26, e.g., between 3 and 15 mm, e.g., 8 mm). That is, for some applications, second tissue anchor 32b may be placed anywhere within a circle having a radius that equals L10, centered on the first tissue anchor (e.g., indicated by arc 1928). For some such applications, sleeve 26 thereby serves as a constraining member (e.g., a tether) that is used to facilitate positioning of second tissue anchor 32b. Distance L10 is thereby set by the operating physician retracting channel 18 from sleeve 26 by a particular distance.

FIG. 3F shows the entire length of sleeve 26 having been anchored, via a plurality of anchors 32, to annulus 240, as described hereinabove. The deployment manipulator (i.e., deployment manipulator 61 described herein but not shown in FIG. 3F) is repositioned along the annulus to additional sites, at which respective anchors are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. Then, system 10 is removed, leaving behind annuloplasty ring structure 222, and guide member 86 coupled thereto.

Figure 3G:
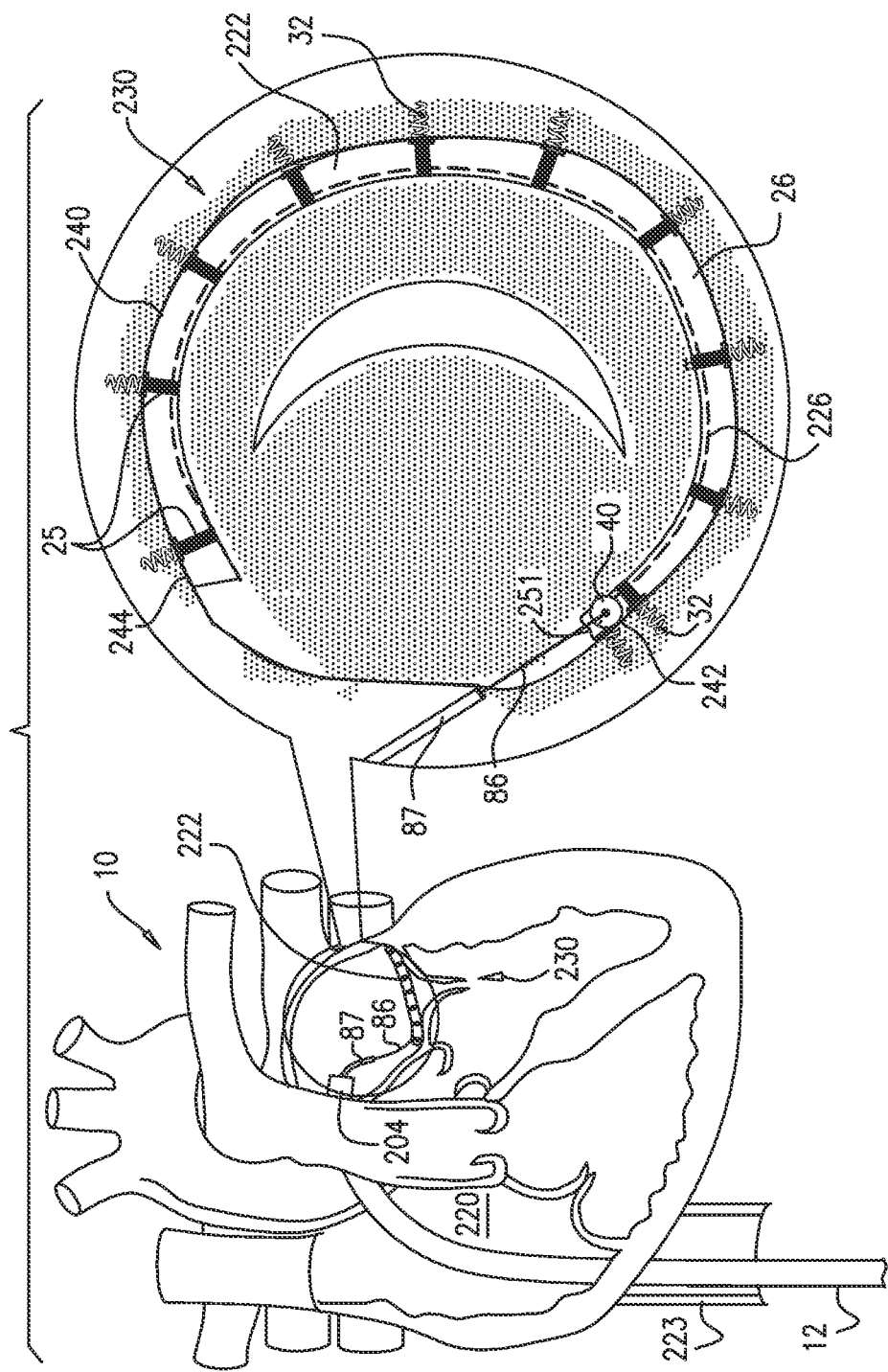

FIG. 3G shows an adjustment tool 87 being threaded over and advanced along guide member 86. Adjustment tool 87 typically comprises a rotation tool, and is configured to actuate (e.g., rotate) adjustment mechanism 40, so as to tension contraction member 226, and thereby contract sleeve 26, as described hereinabove. Typically, adjustment mechanism 40 comprises a housing which houses a spool, i.e., a rotatable structure, to which a first end of contraction member 226 is coupled. Typically, the spool is configured to adjust a perimeter of annuloplasty ring structure 222 by adjusting a degree of tension of contraction member 226 that is coupled at a first portion of member 226 to the spool. The contraction member 226 extends along sleeve 26 and a second portion of contraction member 226 (i.e., a free end portion) is coupled to a portion of sleeve 26 such that upon rotation of the spool in a first rotational direction, the contraction member is pulled toward adjustment mechanism 40 in order to contract annuloplasty ring structure 222. It is to be noted that the contraction of structure 222 is reversible. That is, rotating the spool in a second rotational direction that opposes the first rotational direction used to contract the annuloplasty structure, unwinds a portion of contraction member 226 from around the spool. Unwinding the portion of contraction member 226 from around the spool thus feeds the portion of contraction member 226 back into sleeve 26 of structure 222, thereby slackening the remaining portion of contraction member 226 that is disposed within the sleeve. Responsively, the annuloplasty structure gradually relaxes and expands (i.e., with respect to its contracted state prior to the unwinding).

Adjustment mechanism 40 typically comprises a locking mechanism that prevents actuation of the adjustment mechanism (e.g., rotation of the spool) after contraction member 226 has been tightened. For example, locking techniques may be used that are described with reference to FIG. 4 of U.S. Pat. No. 8,241,351 to Cabiri.

Tool 87 and is used to rotate the spool of adjustment mechanism 40 in order to tighten structure 222 by adjusting a degree of tension of contraction member 226 (not shown in FIG. 3G). Once the desired level of adjustment of structure 222 is achieved, e.g., by monitoring the extent of regurgitation of the valve using echocardiography (such as Doppler echocardiography and/or fluoroscopy), adjustment tool 87 and guide member 86 are removed from the heart. For some applications, a distal portion of guide member 86 may be left within the heart of the subject and the proximal end may be accessible outside the body, e.g., using a port. For such applications, adjustment mechanism 40 may be accessed at a later stage following initial implantation and adjustment of ring structure 222 (e.g., as described with reference to FIGS. 16A-18K).

Alternatively, annuloplasty ring structure 222 is implanted by right or left thoracotomy, mutatis mutandis.

Figure 5A:
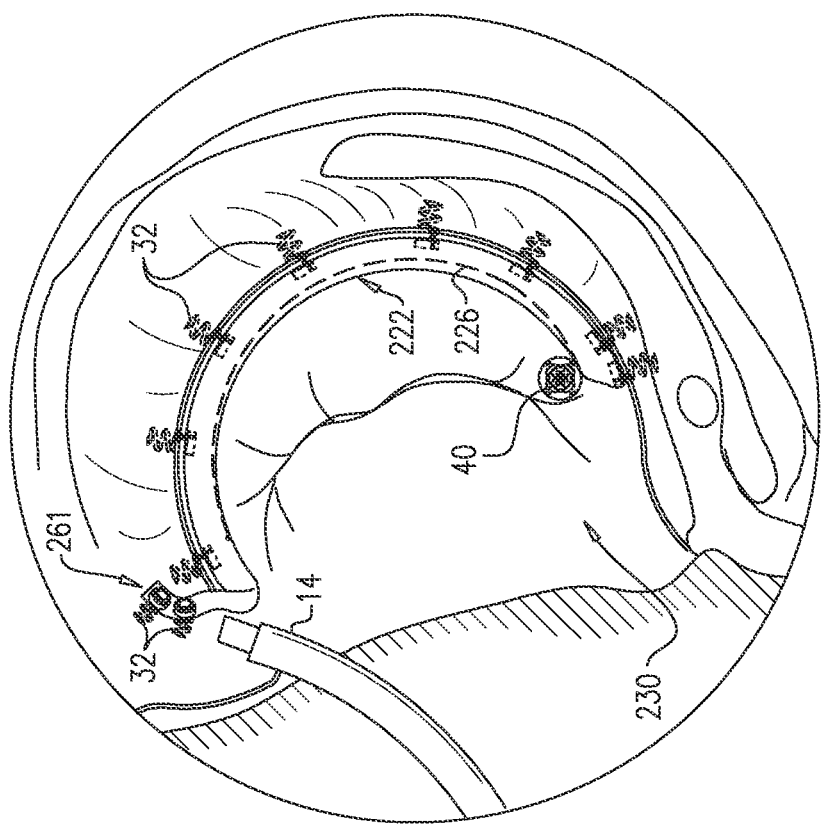
FIGS. 5A-B are schematic illustrations of techniques for use with an excess portion of sleeve, in accordance with some applications of the invention.
Figure 5B:
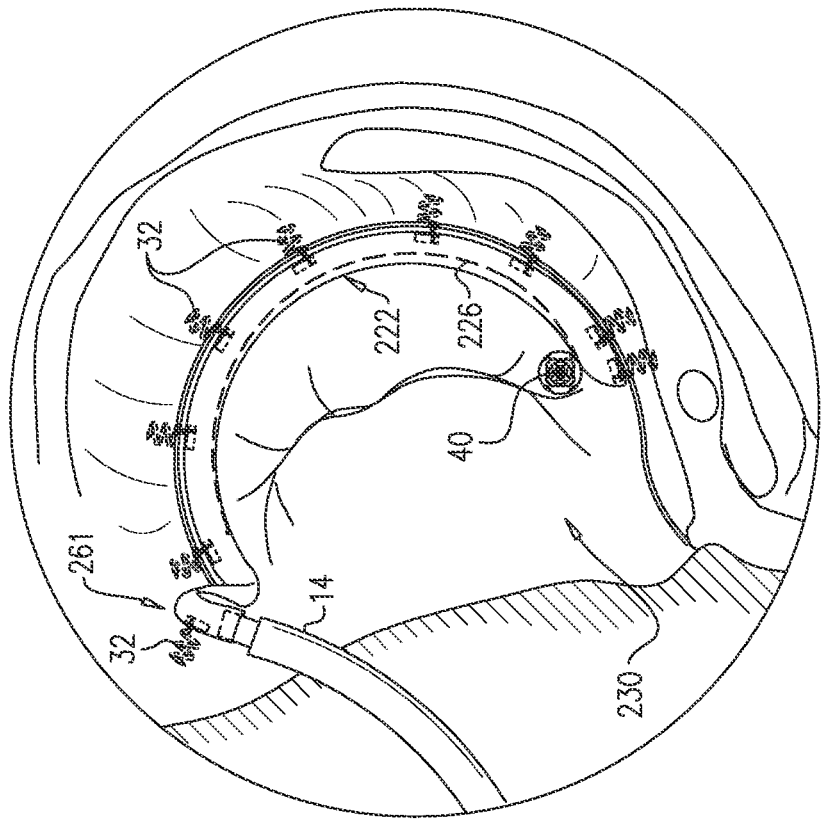

Reference is again made to FIGS. 3A-G, and is also made to FIGS. 5A-B, which are schematic illustrations of techniques for use with an excess portion 261 of sleeve 26, in accordance with some applications of the invention. For some applications of the present invention, following implantation of sleeve 26 along the annulus, an excess portion 261 of sleeve 26 may be present at the proximal portion of sleeve. For some such applications, excess portion 261 may be anchored to an atrial surface, such as an atrial wall, using anchors delivered via the lumen of sleeve 26, as described hereinabove, mutatis mutandis, as shown in FIG. 5A.

Alternatively or additionally, excess portion 261 may be anchored to the atrial surface using anchors driven from outside of sleeve 26, laterally through the sleeve, such that each anchor passes through the lateral wall of the sleeve twice (e.g., on opposite sides of the lumen of the sleeve), as shown in FIG. 5B. Therefore a method is described comprising: (1) percutaneously advancing toward a tissue of a subject structure 222, while a distal portion of a channel 18 is disposed within the lumen of sleeve 26, such that a distal opening of the channel is disposed at a first portion of the sleeve; (2) anchoring the first portion of the sleeve to a first tissue site by using anchor driver 36 to drive tissue-coupling element 60 of a first anchor 32 through the distal opening of the channel, through the first portion of the sleeve (e.g., through end wall 251 or lateral wall 253), and into the first tissue site; (3) pressing a second portion of the sleeve (i.e., excess portion 261) against a second tissue site; and (4) anchoring the second portion of the sleeve to the second tissue site by driving tissue-coupling element 60 of a second anchor 32 from outside the lumen, through opposing sides of the lateral wall at the second portion of the sleeve, and into the second tissue site.

For some applications, when the second portion (i.e., the excess portion) of the sleeve is pressed against the second tissue site (e.g., the atrial wall) the opposing sides of lateral wall 253 at the second portion of the sleeve contact each other.

Reference is again made to FIGS. 3A-G. For anatomical reasons, a transluminal (e.g., transfemoral) approach to the mitral valve via transseptal puncture typically provides access more directly and/or easily to the region of the anterior commissure (e.g., including left fibrous trigone 242) than to the region of the posterior commissure (e.g., including right fibrous trigone 244). It may therefore be advantageous to position and anchor distal end wall 251 of sleeve 26 in the vicinity of the left fibrous trigone; the positioning of the first point of anchoring of structure 222 may be more difficult than the positioning of subsequent points of anchoring (e.g., due to guidance provided by sleeve 26; FIG. 3E). Due to this same reason of accessibility, it may also be advantageous to deliver adjustment tool 87 to the region of the anterior commissure (as shown in FIG. 3G).

System 10 (e.g., structure 222 thereof) is configured to facilitate exploitation of these two advantages: By adjustment mechanism 40 being disposed at a distal end of sleeve 26, and being movable away from the longitudinal axis of the sleeve, (1) the first tissue anchor may be driven through end wall 251 into the region of the anterior commissure, despite the adjustment mechanism having previously been obstructively positioned, and (2) the adjustment tool may be delivered to the region of the anterior commissure because the adjustment mechanism is disposed in that region.

Figure 6B:
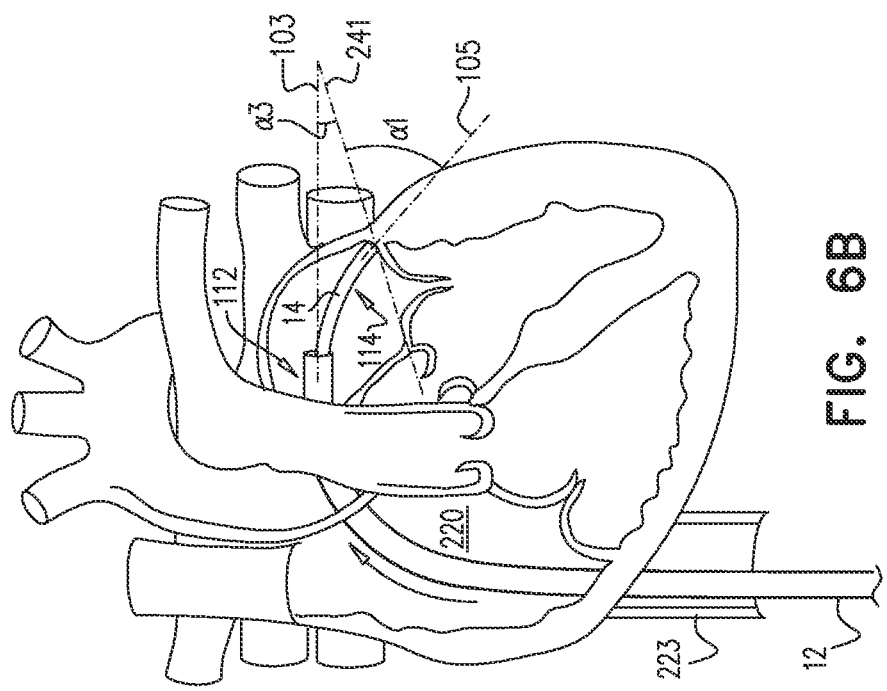
FIGS. 6A-B and 7A-B are schematic illustrations of steering of catheters, in accordance with respective applications of the invention.
Figure 6A:
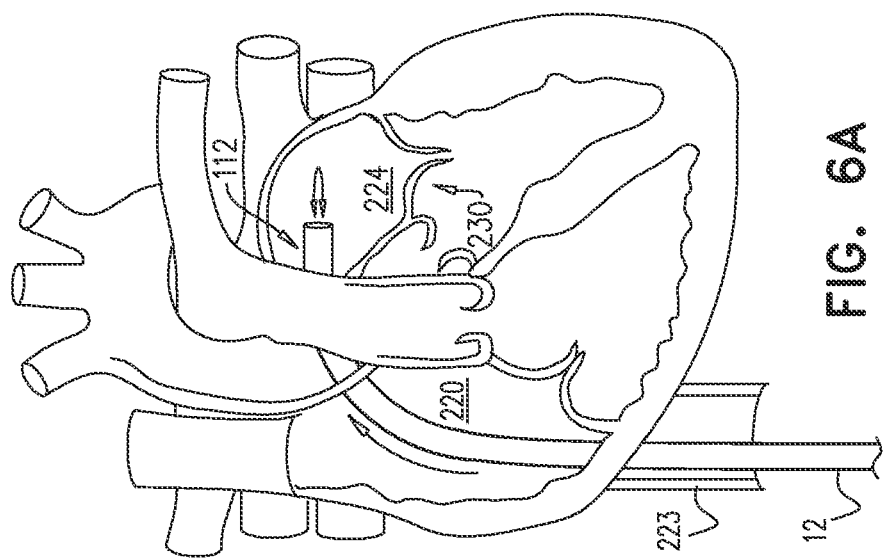
Figure 7B:
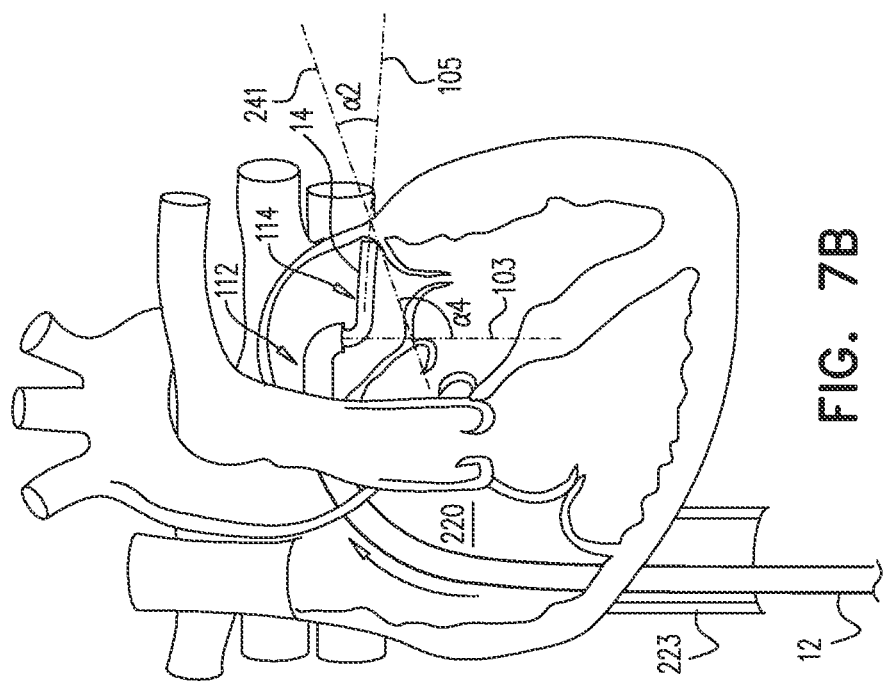
Figure 7A:
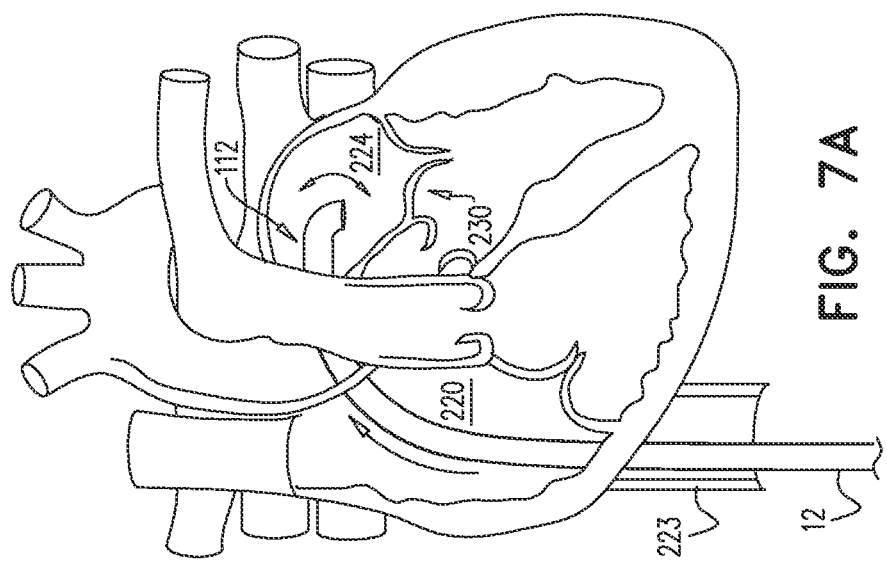

Reference is now further made to FIGS. 6A-B and 7A-B, which are schematic illustrations of steering of catheters 12 and 14, in accordance with respective applications of the invention. As described hereinabove, distal end portion 112 of catheter 12 is steerable in a first steering plane, and distal end portion 114 of catheter 14 is steerable in a second steering plane, typically perpendicular to the first steering plane. As also described hereinabove, typically (i) catheter 12 is steered in a steering plane that is parallel with the plane of the annulus of the valve (e.g., as shown in FIG. 6A), and (ii) catheter 14 is steered downward and toward the annulus of the valve (e.g., as shown in FIG. 6B), such that an angle alpha_1 is formed between (i) plane 241 of the annulus, and (ii) an exit direction 105 from distal end 104 of catheter 14. (Exit direction 105 is typically collinear with the central longitudinal axis through the distal end of manipulator 61, and/or the central longitudinal axis of tissue-coupling element 60 of anchor 32.) Typically, angle alpha_1 is greater than an angle alpha_3 formed between plane 241 and an exit direction 103 from distal end 102 of catheter 12.

Alternatively, catheter 12 may be steered in a different steering plane, such that catheter 14 may approach the tissue from a different angle, such that an anchor 32 may penetrate the tissue at a different angle of attack. For example, and as shown in FIG. 7, catheter 12 may be steered downward and toward the annulus of the valve, and catheter 14 may be steered such that an angle alpha_2 (formed between the plane of the annulus and the central longitudinal axis through the distal end of manipulator 61) is smaller than angle alpha_1. For such applications, angle alpha_2 is typically smaller than an angle alpha_4 formed between plane 241 and exit direction 103.

Reference is now made to FIGS. 8A-B, 9, 10A-C, 11, and 12A-B, which are schematic illustrations of tissue anchors, and the use of the tissue anchors for implantation of structure 222, in accordance with some applications of the invention.

FIG. 8A shows tissue anchor 32, described hereinabove. As shown in FIG. 8A, tissue-coupling element 60 is typically helical, and has a central longitudinal axis 33 (which, when element 60 is helical, is an axis of rotation of element 60). Tool-engaging head 62 has a width d1, and tissue-coupling element 60 has a width (e.g., a helix diameter) d2 that for some applications is about the same as width d1. Width d1 and width d2 are each smaller than the diameter of the lumen of channel 18, thereby facilitating delivery of anchor 32 through channel 18, as described hereinabove. A greatest transverse width of anchor 32 is smaller than the diameter of the lumen of channel 18.

Width d2 is typically between 0.1 and 0.5 cm (e.g., 0.25 cm). Element 60 has a helix length d7 that is typically 0.3-0.9 cm, such as 0.3-0.65 cm (e.g., 0.55 cm), and a helix pitch d8 that is typically 0.05-0.3 cm (e.g., 0.12 cm). Typically, element 60 has a helix wire thickness d9 of 0.02-0.1 cm (e.g., 0.05 cm).

FIG. 8B shows a tissue anchor 332, which is typically identical to tissue anchor 32 except where noted. Anchor 332 comprises a tool-engaging head 362, which is typically (but not necessarily) identical to head 62 of anchor 32. Anchor 332 further comprises a tissue-coupling element 360, and has a central longitudinal axis 333. A width d3 of head 362 is typically smaller than the diameter of the lumen of channel 18, whereas a width d4 of tissue-coupling element 360 is greater than the diameter of the lumen of the channel (and is therefore greater than width d2). For example, widths d1, d2, and d3, and the diameter of the lumen of channel 18 may each be 2-3 mm, and width d4 (which is typically the greatest transverse width of anchor 332) may be 3-4 mm (e.g., about 3.4 mm). Tissue-coupling element 360 therefore typically protrudes radially outward from longitudinal axis 333 further than does head 362, by a distance d5. Alternatively, width d3 may also be greater than the diameter of the lumen of channel 18.

The larger width of element 360 compared to that of element 60 provides increased anchoring strength. It is hypothesized that for some applications this increased anchoring strength is particularly useful for the first anchor used to anchor structure 222 (e.g., the anchor that penetrates end wall 251), due to increased forces exerted on that anchor compared to, for example, anchors further along sleeve 26. Due to width d4 being greater than the diameter of the lumen of channel 18, anchor 332 cannot be advanced through channel 18 in the same manner as anchor 32. FIGS. 9-12B show techniques for anchoring structure 222 (e.g., the distal end of sleeve 26) using anchor 332.

Typically, tissue-coupling element 360 has a helix wire thickness that is generally the same as thickness d9. Tissue-coupling element 360 typically has a helix length that is generally the same as length d7. For some applications, a helix pitch d10 of element 360 is different to pitch d8. For example, pitch d10 may be smaller than pitch d8, so as to maintain the helix length of element 360 as generally the same as length d7. For some applications, a helix angle alpha_6 (the angle between the helix and its central longitudinal axis) of element 360 is different to a helix angle alpha_5 of element 60. For example, angle alpha_6 may be greater than angle alpha_5, so as to maintain the helix length of element 360 as generally the same as length d7.

At least tissue-coupling element 360 of anchor 332 is disposed outside of distal end 17 of channel 18 at the time that channel 18 is loaded into the lumen of the sleeve. For example, deployment element 38 of anchor driver 36 may be advanced, without an anchor coupled thereto, through channel 18, and subsequently coupled to head 362 of anchor 332. An assembly comprising element 38 (and optionally head 362) may then be retracted into channel 18 before the channel, anchor 332, and driver 36 are advanced together into sleeve 26. For some applications, this assembly is advanced through catheter 14 (and out of the distal end thereof) prior to being advanced into sleeve 26. Therefore, tissue-coupling element 360 does not require passage through channel 18, thereby facilitating the use of anchor 332.

For some applications, and as shown in FIGS. 9-10C, during advancement of structure 222, tissue-coupling element 360 is disposed (i) outside of distal end 17 of channel 18, and (ii) inside the lumen of sleeve 26. This may be understood by comparing FIG. 9 with FIG. 1. The steps shown in FIGS. 10A-C generally correspond to the steps shown in FIGS. 3A-C, but with element 360 disposed outside of distal end 17 of channel 18, and inside the lumen of sleeve 26. Subsequent to the anchoring of anchor 332 (FIG. 10C), a plurality of anchors 32 are used to anchor the remainder of structure 222, as described hereinabove, mutatis mutandis.

Figure 12A:
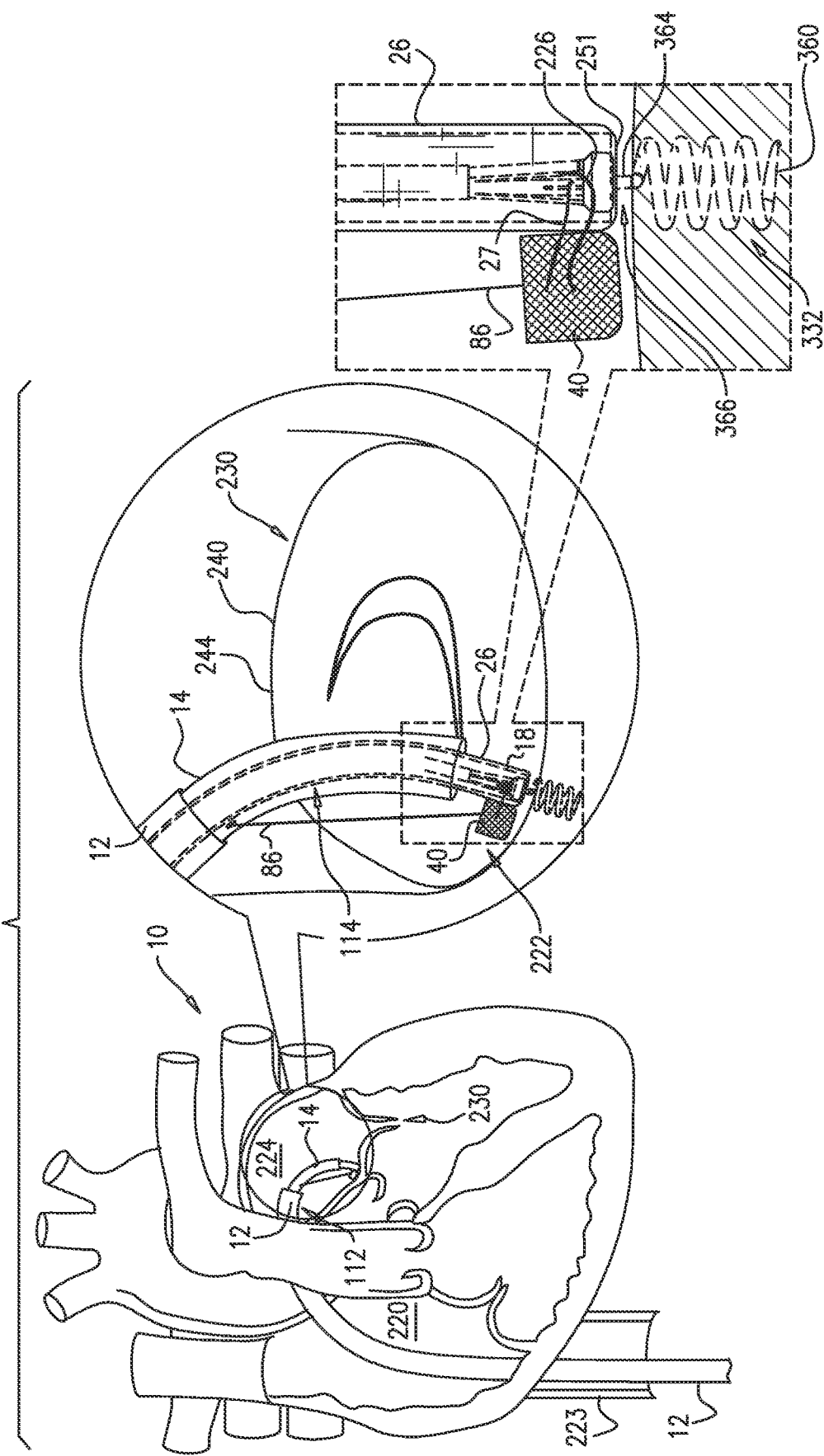
Figure 12B:
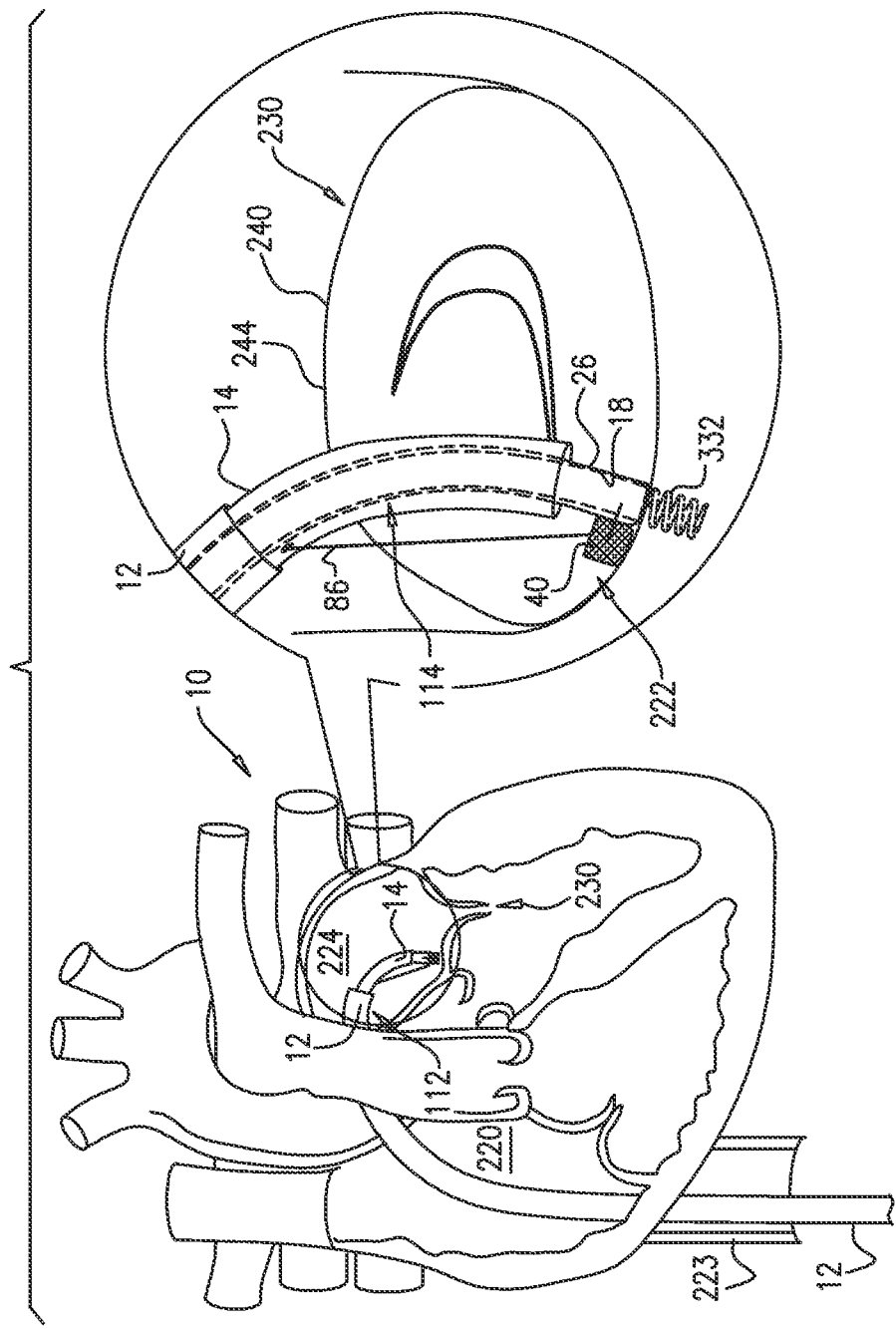

For some applications, and as shown in FIGS. 11-12B, during advancement of structure 222, tissue-coupling element 360 is disposed (i) outside of distal end 17 of channel 18, and (ii) outside of sleeve 26, e.g., having been driven through sleeve 26 (e.g., end wall 251 thereof). This may be understood by comparing FIG. 11 with FIG. 9 (and/or FIG. 1). The steps shown in FIGS. 12A-B generally correspond to the steps shown in FIGS. 10B-C, but with element 360 disposed outside of sleeve 26. Because element 360 protrudes through sleeve 26, at the time that element 360 contacts the tissue, the sleeve is not pressed against the tissue before driving anchor 332, and a gap 366 exists between the tissue and the sleeve. Tissue anchor 332 typically has a straight and/or central stem portion 364 that facilitates subsequent closure of this gap by allowing free rotation of the anchor within the sleeve, e.g., as is known in the art for captive screws. This feature is described in more detail in WO 2014/064694 to Sheps et al., which is incorporated herein by reference.

Reference is made to FIGS. 13A-D and 14A-F, which are schematic illustrations of a system 400, comprising a tissue anchor 402, an anchor driver 404, and a lance 406, and techniques for use with the system, in accordance with some applications of the invention.

Except for where noted, anchor driver 404 is typically identical to anchor driver 36 described herein, and is typically substitutable for anchor driver 36, mutatis mutandis. Except for where noted, tissue anchor 402 is typically identical to tissue anchor 32 described herein, and is substitutable for tissue anchor 32, mutatis mutandis. Anchor driver 404 comprises an elongate shaft 408 (which is typically tubular) and a deployment manipulator 410 coupled to a distal end of the shaft.

System 400 is shown being used to anchor structure 222, but it is to be noted that the scope of the invention includes using system 400 in other situations that require percutaneous delivery of tissue anchors. Tissue anchor 402 comprises a tissue-coupling element, which in FIGS. 13A-14F is shown as element 60, but which could comprise a different tissue-coupling element.

Lance 406 serves two functions: (1) to facilitate reversible locking of driver 404 to anchor 402, and (2) to stabilize system 400 at the tissue prior to driving of anchor 402 into the tissue.

Figure 14A:
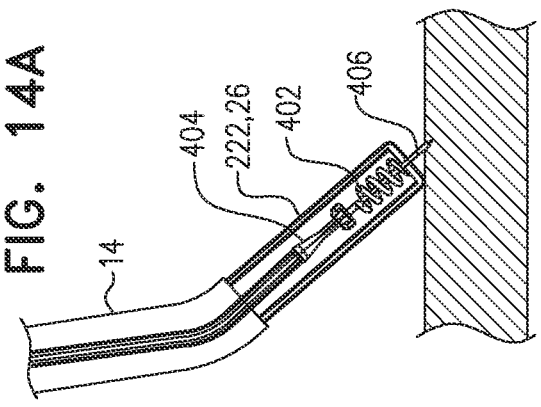
Figure 14B:
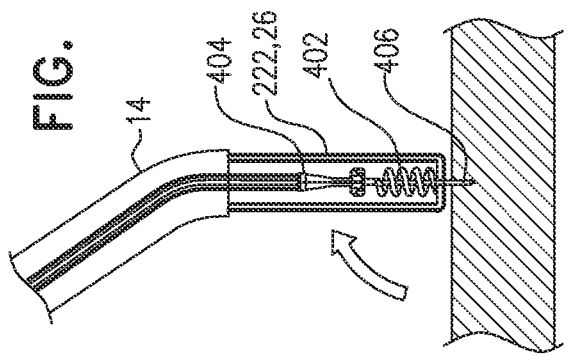

System 400 is advanced while a distal tip of lance 406 extends distally past a distal tip of tissue-coupling element 60 (e.g., in the state shown in FIG. 13A), such that the lance engages the tissue before element 60 does (FIG. 14A). Lance 406 penetrates the tissue, thereby stabilizing system 400 at the tissue. As illustrated by the transition between FIG. 14A and FIG. 14B, for some applications system 400 is used in combination with a catheter system that facilitates pivoting (i.e., deflection) of system 400 about the point at which lance 406 penetrates the tissue. For example, such a catheter system may comprise catheter 14 (as shown), catheter 12, and/or other elements of system 10. It is hypothesized that this facilitates separation between (i) correctly locating anchor 402 at the anchor site, and (ii) correctly orienting the anchor with respect to the tissue at the anchor site. That is, lance 406 can penetrate the tissue at the correct location but the incorrect orientation (e.g., angle) (FIG. 14A), and system 400 can be subsequently deflected about that location (e.g., using the lance as a pivot) so as to obtain the correct orientation (e.g., the correct angle of attack for anchor 402) (FIG. 14B).

Figure 14C:
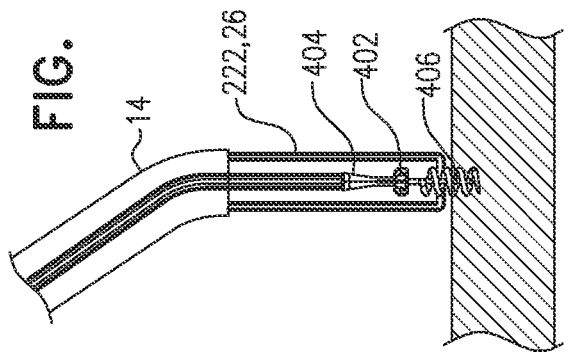
Figure 14D:
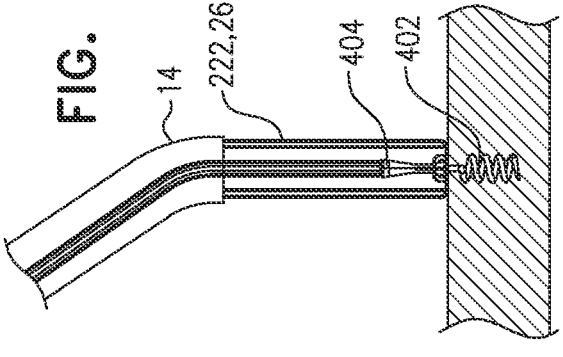
Figure 14E:
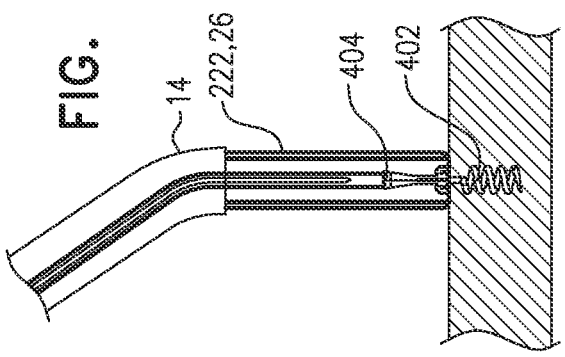

Anchor 402 is typically driven at least partway into the tissue before partially retracting lance 406 (FIGS. 14C-D). FIG. 13B shows lance 406 in this partly retracted position. The presence of lance 406 within deployment manipulator 410 retains the deployment manipulator locked to anchor 402 (e.g., to a tool-engaging head 412 thereof). For example, and as shown, deployment manipulator 410 may comprise one or more detents 414 that are held in a locking position (e.g., radially outward) by lance 406. The partial retraction of lance 406 shown in FIG. 13B does not remove the lance from deployment manipulator 410, and so the manipulator remains locked to anchor 402.

Figure 14F:
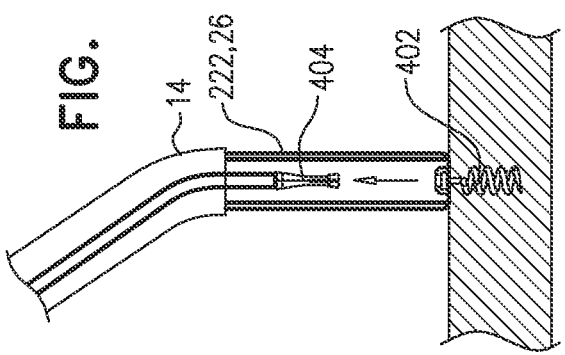

FIG. 14D shows anchor 402 fully anchored to the tissue, and lance 406 partially retracted. Subsequent to the anchoring, lance 406 is retracted further, thereby unlocking deployment manipulator 410 from anchor 402 (FIG. 14E), e.g., due to detents 414 responsively moving radially inward, as shown in FIG. 13C. Driver 404 may then be decoupled from anchor 402 (FIGS. 14F and 13D).

Apparatus is therefore described, comprising (1) an anchor, comprising (a) an anchor head, and (b) a tissue-engaging member, coupled to the anchor head, extending distally away from the anchor head until a distal tip of the tissue-engaging member, and configured to anchor the anchor to the tissue; (2) an anchor driver, comprising: (a) a longitudinal shaft, having a flexible distal portion and a distal end, (b) a deployment element at the distal end of the shaft, reversibly lockable to the anchor head, and reversibly movable between (i) a locked state that retains locking between the deployment element and the anchor head, and (ii) an unlocked state that unlocks the deployment element from the anchor head, and (c) a tissue-piercing lance, reversibly movable between an extended state in which (i) the lance extends distally from the shaft, (ii) while the deployment element is locked to the anchor head, the lance extends distally past the distal tip of the anchor, and (iii) the lance retains the deployment element in the locked state, and a retracted state in which the deployment element automatically moves into the unlocked state.

Apparatus is therefore also described, comprising (1) a percutaneous catheter; (2) an implant, dimensioned to be advanced into the subject via the catheter; (3) an anchor-delivery channel, shaped to define a lumen therethrough, the lumen having a diameter, and the channel being dimensioned to be disposable within the catheter; (4) at least one anchor, comprising an anchor head coupled to a tissue-coupling element, the anchor head defining an aperture therethrough, and (5) an anchor driver (i) comprising a stem, and a driver head coupled to the distal end of the stem, the driver head being reversibly couplable to the anchor head, (ii) configured to advance the anchor through the lumen of the channel while the driver head is coupled to the anchor head, (iii) further comprising a lance that is reversibly extendable with respect to the driver head, such that when the driver head is coupled to the anchor head, extension of the lance causes the lance to slide through the aperture such that a tip of the lance becomes disposed distally beyond a distal tip of the tissue-engaging element, and (iv) configured to drive the tip of the lance through a portion of the implant and into the tissue of the subject, and to drive the tissue-coupling element of the anchor through the portion of the implant and into the tissue of the subject, independently of the driving of the tip of the lance.

Apparatus is therefore also described, comprising (1) an anchor, comprising (i) an anchor head, having a proximal side and a distal side, and defining an aperture from the proximal side to the distal side, (ii) a tissue-engaging member, coupled to the anchor head, extending distally away from the anchor head until a distal tip of the tissue-engaging member, and configured to anchor the anchor to the tissue; (2) an anchor driver, comprising (i) a longitudinal shaft, having a flexible distal portion and a distal end, (ii) a tissue-piercing lance, reversibly extendible distally from the shaft, (iii) a deployment element coupled to the distal end of the shaft, and reversibly couplable to the anchor head in a position in which extension of the lance distally from the shaft moves the lance through the aperture and past the distal tip of the anchor; and (3) a catheter system, comprising (i) a catheter through which the anchor driver is intracorporeally advanceable (a) while the deployment element is coupled to the anchor head, and (b) such that the distal portion of the shaft extends distally out of the catheter, and having a distal segment that is intracorporeally deflectable with respect to another segment of the catheter immediately proximal to the distal segment, and (ii) an extracorporeal controller configured, while the distal portion of the shaft is extended distally out of the catheter, and the lance is extended distally from the shaft and is disposed in the tissue, to cause deflection of the distal segment with respect to the other segment, such that the distal portion of the shaft deflects with respect to another portion of the shaft immediately proximal to the distal portion, the anchor driver being configured to drive the tissue-engaging member into the tissue while the distal portion of the shaft is deflected with respect to the other portion of the shaft.

A method is therefore also described, comprising (1) advancing a distal end of an anchor driver through a catheter and toward a tissue of a subject, the anchor driver including a shaft, a tissue-piercing lance, and a deployment element; (2) subsequently, piercing the tissue with the lance; (3) deflecting a distal portion of the shaft with respect to another portion of the shaft immediately proximal to the distal portion, by moving a distal segment of the catheter while at least some of the lance is disposed within the tissue; and (4) while (i) the distal portion of the shaft is deflected with respect to the other portion of the shaft, and (ii) the deployment element is locked to a head of an anchor, driving a tissue-engaging member of the anchor into the tissue using the anchor driver.

Reference is made to FIGS. 15A-B, which are schematic illustrations of implants 422a and 422b that each comprise a contracting wire, in accordance with some applications of the invention. Each of implants 422a and 422b comprise an annuloplasty structure that comprises (1) a sleeve, having a first end and a second end, a bearing site, and comprising a lateral wall that defines a lumen from the first end to the second end, (2) adjustment mechanism 40, and (3) a contraction member (a) having a first end coupled to the adjustment mechanism, (b) having a first portion that extends from the adjustment mechanism along the sleeve toward the second end, until the bearing site, and (c) having a second portion that extends from the bearing site back toward the adjustment mechanism and the first end, the adjustment mechanism being configured to reduce a length of the sleeve between the first end and the second end by pulling on the first portion of the contraction member such that the second portion of the contraction member progressively slides past the bearing site.

Typically, implants 422a and 422b are identical to structure 222, except where noted, and may be used, in place of structure 222, in techniques described herein. Similarly, the sleeve of each implant is typically identical to sleeve 26, mutatis mutandis, and the reference numeral 26 is also used for these sleeves.

Implant 422a comprises a contraction member 426a. A first end of contraction member 426a is coupled to mechanism 40. A first portion 424a of contraction member 426a extends from mechanism 40 through the lumen of sleeve 26 toward proximal end 252 of the sleeve, until a bearing site 430. A second portion 428a of contraction member 426a extends from bearing site 430 back toward adjustment mechanism 40 and the distal end of the sleeve (e.g., end wall 251), weaving through lateral wall 253 of sleeve 26.

Implant 422b comprises a contraction member 426b. A first end of contraction member 426b is coupled to mechanism 40. A first portion 424b of contraction member 426a extends from mechanism 40 toward proximal end 252 of sleeve 26, weaving through lateral wall 253, until a bearing site 430. A second portion 428b of contraction member 426a extends from bearing site 430 back toward adjustment mechanism 40 and the distal end of the sleeve (e.g., end wall 251), weaving through lateral wall 253 of sleeve 26. Implant 422b is typically identical to implant 422a, except that the first portion of contraction member 426b also weaves through lateral wall 253 of sleeve 26.

For each of implants 422a and 422b, when adjustment mechanism 40 tensions the contraction member, the second portion of the contraction member progressively slides past (e.g., through) bearing site 430. (This typically occurs as bearing site 430 moves toward adjustment mechanism 40 due to the contraction of the implant). Typically, and as shown, bearing site 430 is defined by a hole in sleeve 26, reinforced by an eyelet (e.g., a metal ring, such as a grommet). For some applications, bearing site 430 may comprise a different bearing, such as a wheel (e.g., a sheave). It is to be noted that for both implant 422a and implant 422b, both the first portion and the second portion of the contraction member become shortened during contraction of sleeve 26.

Typically, for both implant 422a and implant 422b, the first portion of the contraction member enters sleeve 26 via a hole in the sleeve, reinforced by an eyelet (e.g., a metal ring, such as a grommet). This hole may also serve as a bearing site 431, through which the first portion of the contraction member slides when adjustment mechanism 40 tensions the contraction member.

Typically, a second end 429 of the contraction member (i.e., the end not coupled to adjustment mechanism 40) is fixedly coupled to the sleeve (e.g., using a crimp bead, as shown).

Reference is made to FIGS. 16A-B, 17A-C and 18A-K, which are schematic illustrations of a system 440 for docking with and adjusting an adjustment mechanism of a percutaneously-implantable implant, and techniques for use therewith, in accordance with some applications of the invention.

Apparatus is described, comprising: (1) a percutaneously-implantable implant (e.g., annuloplasty ring structure 222, comprising sleeve 26); (2) an adjustment device 442, comprising (i) an adjustment mechanism (e.g., mechanism 40), coupled to the implant, and configured to change a dimension of the implant upon actuation of the adjustment mechanism; and (ii) a lock 444, (a) having a locked state in which the lock inhibits actuation of the adjustment mechanism, (b) having an unlocked state in which the adjustment mechanism is actuatable, and (c) reversibly movable between the locked state and the unlocked state; (3) a longitudinal guide member (e.g., guide member 86); and (4) an adapter 446: (i) coupled to the guide member, (ii) comprising a fastener 448 that couples the adapter to the adjustment device, and is intracorporeally decouplable from the adjustment device, (iii) configured to be percutaneously delivered while coupled to the adjustment device, and (iv) comprising an unlocking mechanism 450, configured such that, while the adapter is coupled to the adjustment device, actuation of the unlocking mechanism moves the lock between the locked state and the unlocked state.

FIGS. 16A-B are schematic illustrations of adapter 446 coupled to adjustment device 442, in accordance with some applications of the invention. As described hereinbelow, adapter 446 is typically coupled to adjustment device 442 before delivery and implantation of the implant (e.g., the adapter is provided pre-coupled to device 442, or is coupled to device 442 by the physician prior to implantation), and the implant is delivered and implanted with adapter 446 coupled to device 442. FIG. 16A shows an exploded view of adjustment device 442 and adapter 446, and FIG. 16B shows an assembled view, with the adapter coupled to the adjustment device.

Adapter 446 comprises a trunk 452 (i.e., a main body portion) that is coupled to fastener 448. Typically, unlocking mechanism 450 comprises a pin disposed in a channel, and actuation of the unlocking mechanism to unlock lock 444 of adjustment device 442 (described hereinbelow) comprises sliding of the pin within the channel. For some applications, and as shown, at least part of this channel is defined by fastener 448. For some applications, and as shown, at least part of this channel is defined by trunk 452. Trunk 452 typically comprises a lateral opening 474 through which an appendage 451 of the pin protrudes.

Lock 444 comprises a depressible portion 443 that defines, or is coupled to, a detent 445, and is unlocked by unlocking mechanism 450 pressing on the depressible portion, thereby moving the detent, as described hereinbelow.

Trunk 452 is shaped such that an external shape of a transverse cross-section of at least a proximal portion of the trunk (the upper portion as shown in the figures) is non-circular. This facilitates application of torque to trunk 452, so as to decouple (e.g., unscrew) adapter 446 from adjustment device 442, as described hereinbelow.

For some applications, and as shown, fastener 448 is shaped to define a screw thread that screws into a corresponding screw thread defined by adjustment device 442, and adapter 446 is decouplable from adjustment device 442 by unscrewing.

Figure 17A:
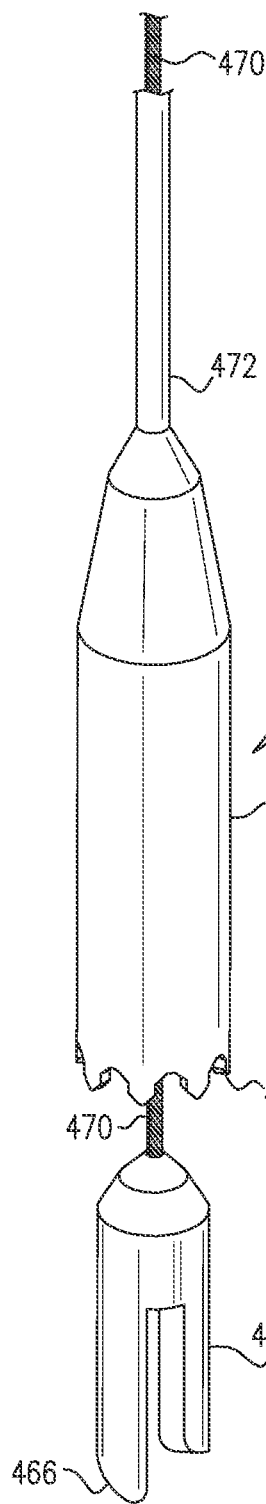
Figure 17B:
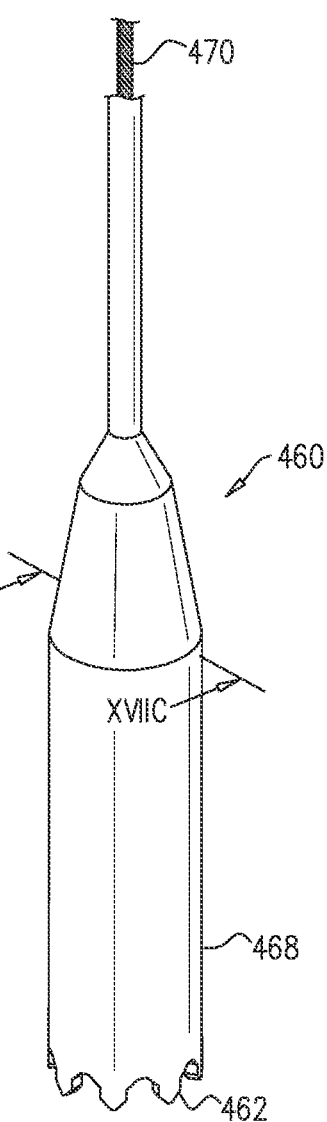
Figure 17C:
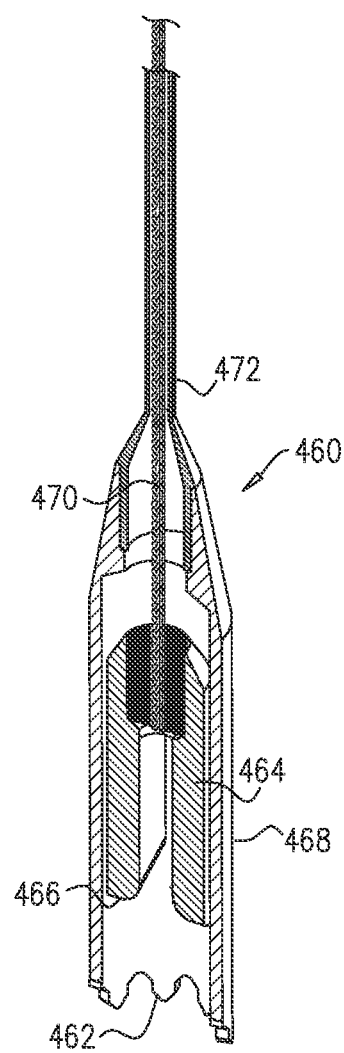

FIGS. 17A-C are schematic illustrations of an adjustment tool 460, in accordance with some applications of the invention. Adjustment tool 460 is percutaneously advanceable along guide member 86 to adapter 446 subsequently to implantation of structure 222, and comprises (i) an adjustment-mechanism interface 462, dimensioned to interface with (e.g., to engage) mechanism 40, and (ii) an adapter interface 464, dimensioned to interface with (e.g., to engage) adapter 446, and comprising a force applicator 466. For some applications, and as shown, force applicator 466 is defined by a distal portion of adapter interface 464. Tool 460 is configured (1) to move lock 444 into its unlocked state by, while adapter 446 is coupled to adjustment device 442, actuating unlocking mechanism 450 by applying, with force applicator 466, a force to the unlocking mechanism, and (2) to actuate adjustment mechanism 40 via the interface between adjustment-mechanism interface 462 and the adjustment mechanism. Typically, tool 460 is also configured to decouple adapter 446 from adjustment device 442.

For some applications, and as shown, force applicator 466 is axially slidable with respect to adapter 446, and is configured to actuate unlocking mechanism 450 by applying an axial force (e.g., a distal force) to the unlocking mechanism. For such applications, adapter interface 464 (or at least applicator 466 thereof) is typically axially slidable with respect to adjustment-mechanism interface 462. FIG. 17A shows force applicator 466 slid axially distally with respect to interface 462, and FIGS. 17B-C show (in isometric and cutaway views, respectively) the force applicator slid axially proximally with respect to interface 462, e.g., such that the force applicator is disposed within a tubular portion 468 of interface 462. This sliding is typically driven via a control rod 470, coupled to adapter interface 464 and accessible from outside the subject, e.g., extending from the adapter interface to outside the subject, such as to a handle of tool 460 (not shown).

For some applications, and as shown, the slidability of tool 460 along guide member 86 is provided by rod 470 being tubular and being slidable over rod 470. For some applications, and as shown, movement of adjustment-mechanism interface 462 is facilitated via an outer tube 472, a distal end of which may define interface 462, and tubular portion 468.

As described hereinabove, contraction of structure 222 may be performed while monitoring the heart (e.g., using Doppler echocardiography) so as to determine a desired amount of contraction (typically an amount of contraction that results in the least regurgitation). It is hypothesized that for some applications, contact between the adjustment tool and the adjustment mechanism may interfere with such monitoring, e.g., by applying a force that temporarily deforms the anatomy of the valve. As described hereinbelow, system 440 provides reversible and repeatable coupling of adjustment tool 460 to adjustment device 442, and repeatable unlocking, adjustment and relocking of the adjustment device (e.g., of adjustment mechanism 40 thereof), and thereby facilitates such monitoring by allowing the monitoring to be performed while the adjustment tool is not in contact with the adjustment device.

Figure 18B:
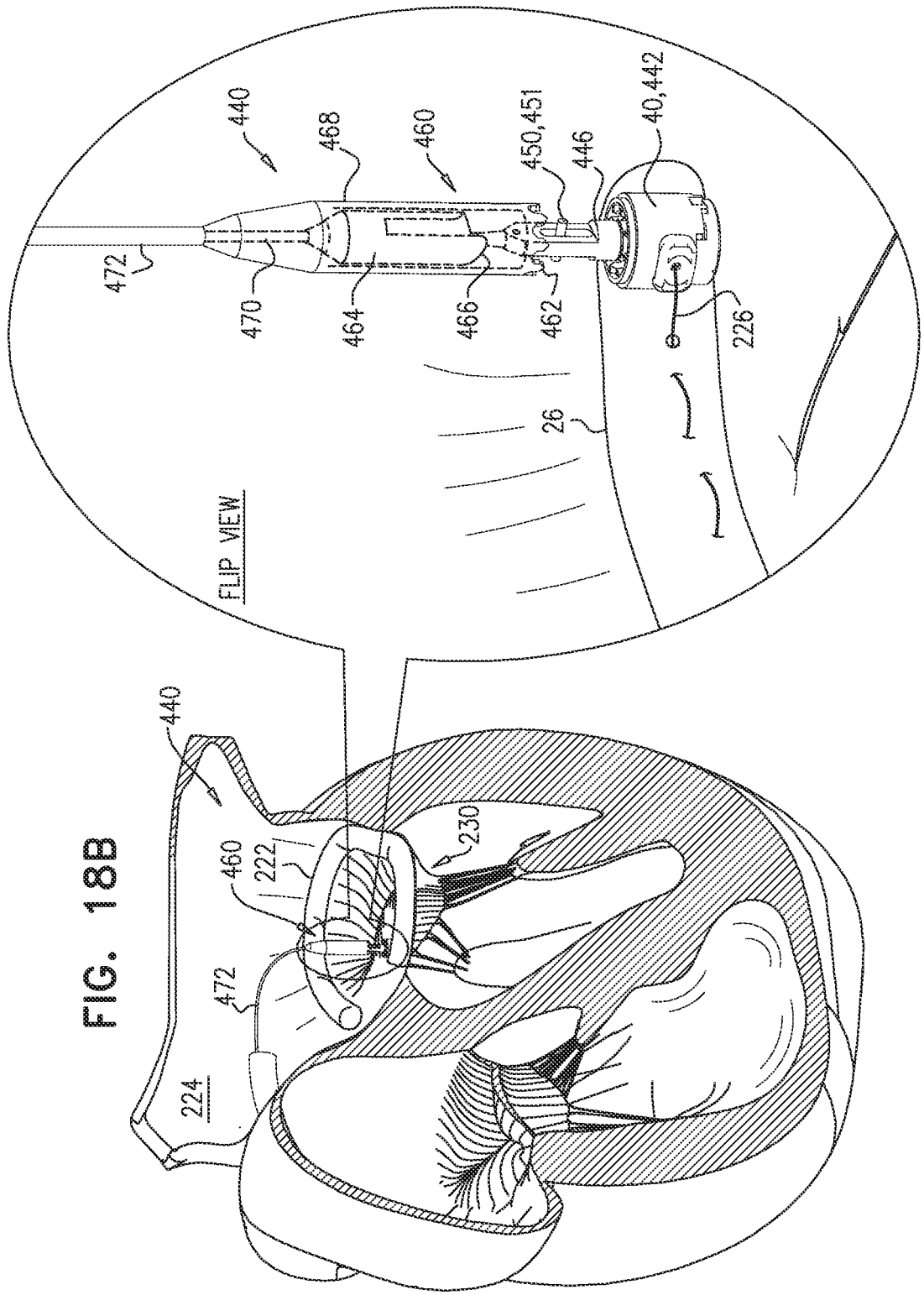

FIGS. 18A-K show techniques for use with system 440, in accordance with some applications of the invention. FIG. 18A shows structure 222 having been implanted at valve 230. Adapter 446 is coupled to adjustment device 442; structure 222 is typically percutaneously advanced and implanted while the adapter is coupled to the adjustment device.

Subsequently, tool 460 is advanced over guide member 86 toward adjustment device 442, as described for tool 87, mutatis mutandis (FIG. 18B). Adapter interface 464 is slidable over trunk 452 to a sufficient extent that force applicator 466 reaches appendage 451. For some applications, and as shown, a distal portion of adapter interface 464 (e.g., force applicator 466) is angled such that, in response to sliding of the adapter interface axially over the proximal portion of trunk 452, the adapter interface automatically assumes a pre-determined rotational orientation with respect to the trunk; typically such that the force applicator aligns with appendage 451. For some applications, and as shown, a proximal portion of adapter 446 is angled such that, in response to sliding of adapter interface 464 axially over the proximal portion of trunk 452, the adapter interface automatically assumes the pre-determined rotational orientation. For example, and as shown, trunk 452 may define one or more shoulders 454 that are angled in this way.

This automatic rotational alignment is illustrated by FIGS. 18C-E. In FIG. 18C, tool 460 arrives at adapter 446 with adapter interface 464 and force applicator 466 misaligned. For example, adapter interface 464 is rotationally oriented such that force applicator 466 is not aligned with appendage 451. FIG. 18D shows that, in response to further axial sliding of adapter interface 464 over trunk 452, the adapter interface automatically rotates into the pre-determined orientation in which force applicator 466 aligns with appendage 451. As described hereinabove, this may be facilitated by an angled portion of adapter interface 464 and/or an angled portion of trunk 452. FIG. 18E shows further axial advancement of tool 460, such that adjustment-mechanism interface 462 interfaces with adjustment mechanism 40. As shown, at this time, lock 444 is locked, e.g., with detent 445 inhibiting actuation (e.g., rotation) of adjustment mechanism 40.

Figure 18F:
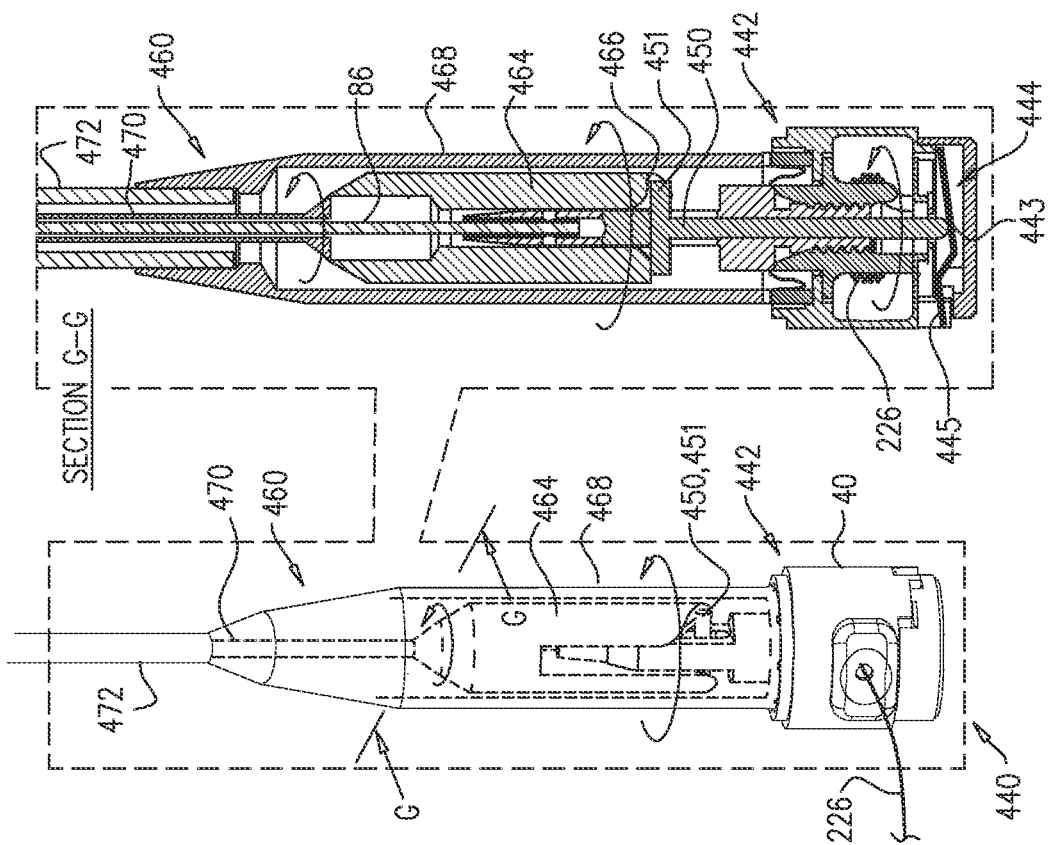

Subsequently, force applicator 466 actuates unlocking mechanism 450 (e.g., by applying an axial force thereto, such as via appendage 451), which responsively unlocks lock 444 (FIG. 18F). For example, and as shown, the pin of unlocking mechanism 450 may slide axially within its channel, and press on depressible portion 443 of lock 444, thereby disengaging detent 445 from adjustment mechanism 40. It is to be noted that, while (i) adapter interface 464 is disposed over trunk 452, and (ii) force applicator 466 is in contact with unlocking mechanism 450 (e.g., appendage 451 thereof), the non-circular shape of the trunk inhibits the adapter interface from rotating further in response to further sliding of the adapter interface axially over the trunk. For example, the angle of force applicator 466 that causes adapter interface 464 to rotate when axially pushed over trunk 452 may also provide a rotational force to the adapter interface when axially pushed against appendage 451. Such rotational force is resisted by the non-circular shape of trunk 452, and a corresponding (e.g., mating) shape of adapter interface 464.

Figure 18G:
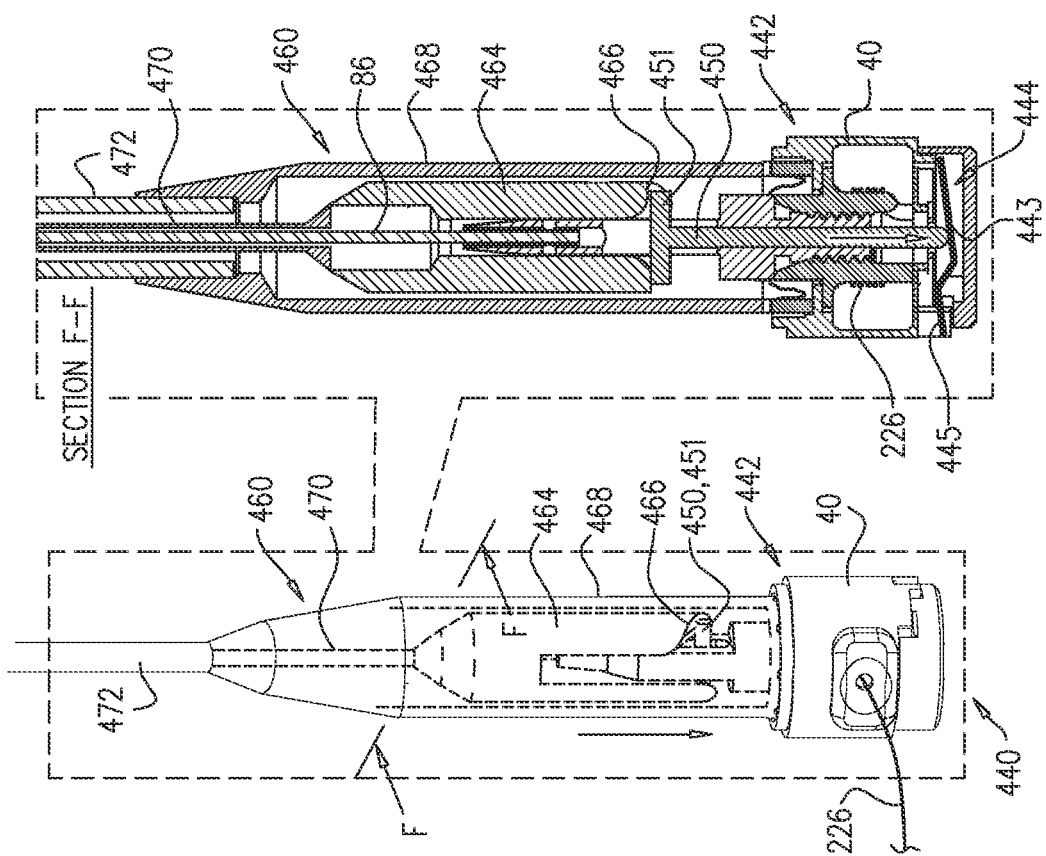

While lock 444 is unlocked, adjustment-mechanism interface 462 actuates adjustment mechanism 40, thereby changing a dimension of the implant (e.g., contracting the implant), e.g., by adjusting tension of contraction member 226 (FIG. 18G).

Figure 18H:
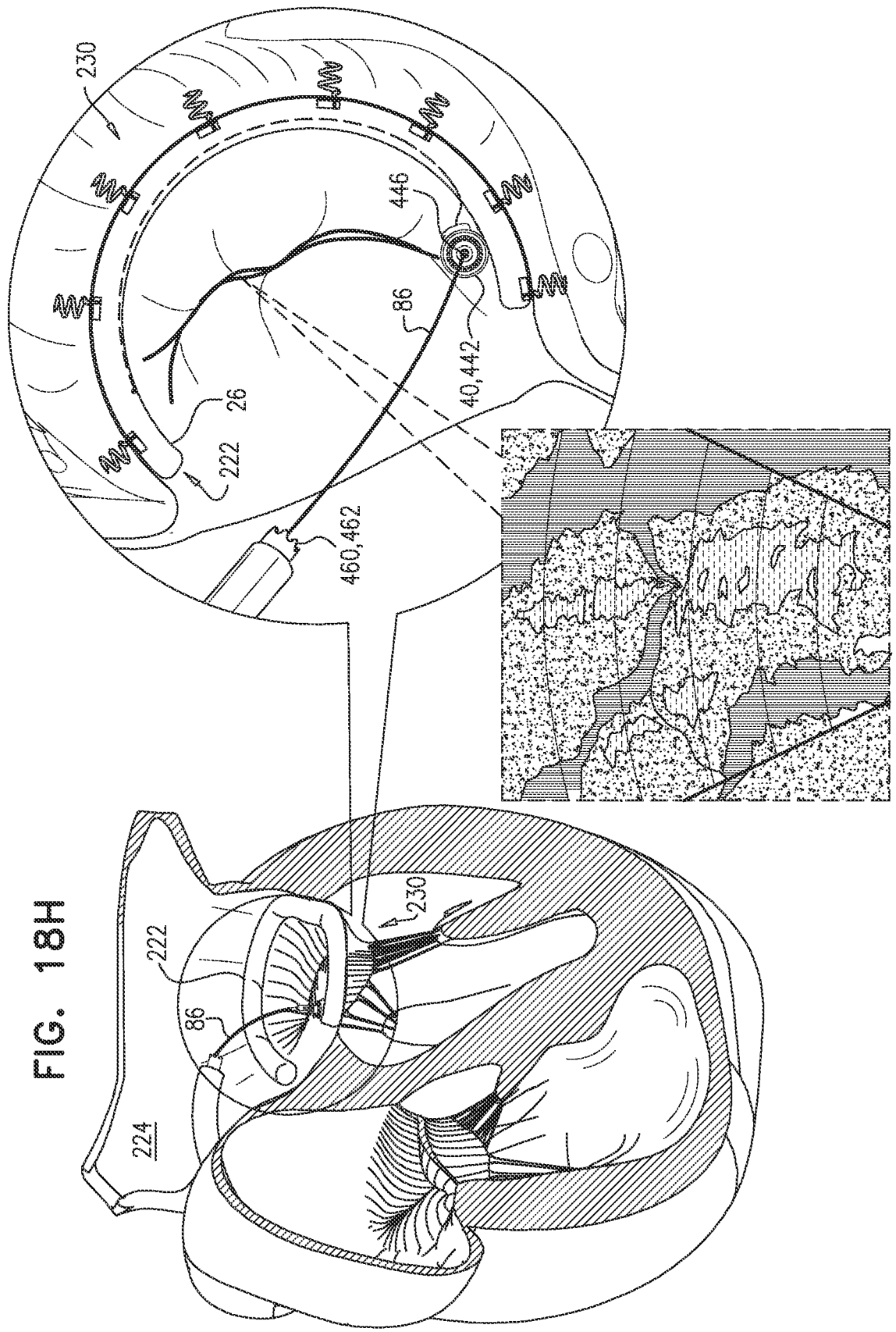
Figure 18I:
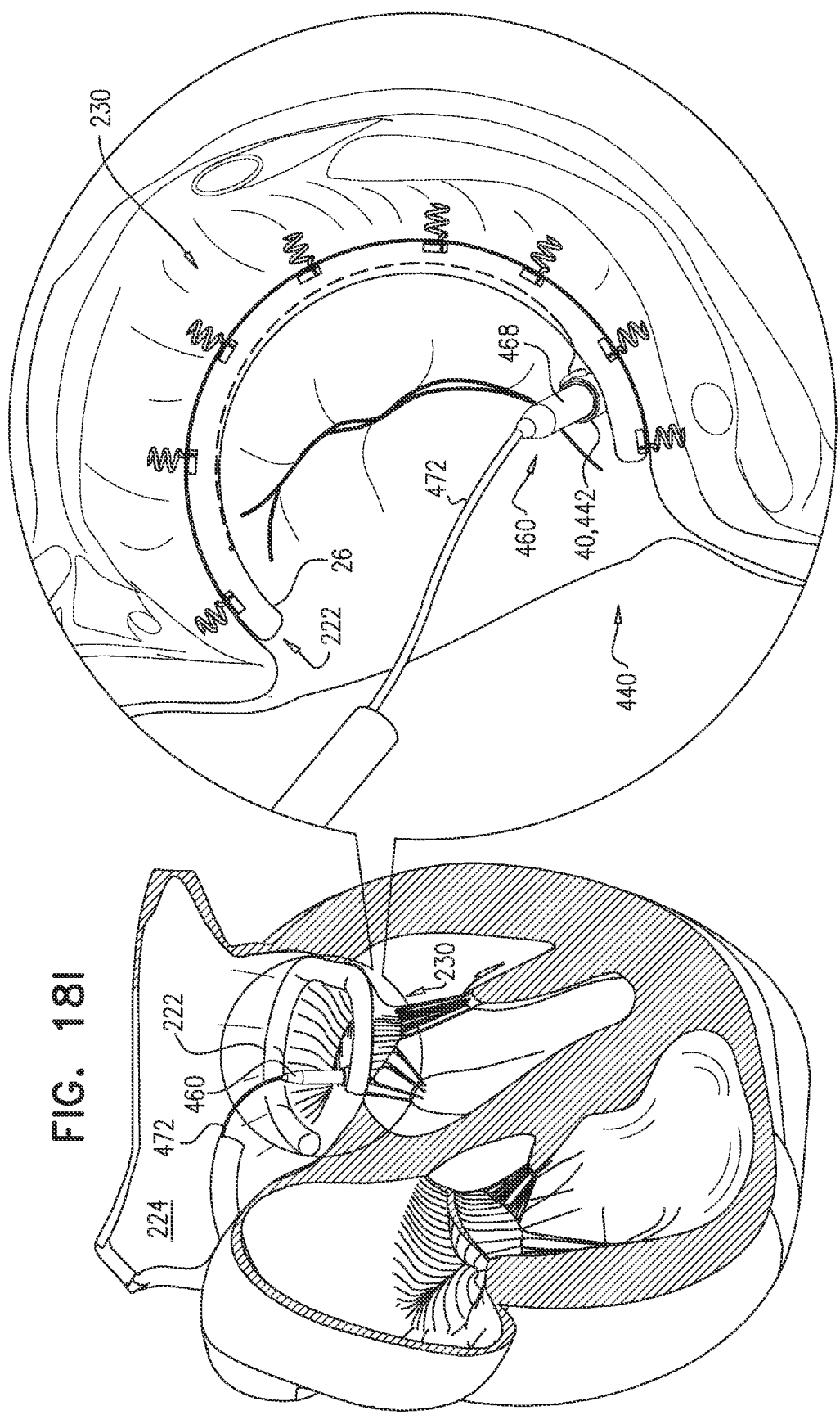

After this adjustment, tool 460 is retracted along guide member 86 away from structure 222, e.g., partially or completely into catheter 12, while the guide member remains coupled to the implant (e.g., coupled to adjustment device 442 via adapter 446) (FIG. 18H). At this time, lock 444 is in a locked state, having been relocked prior to de-interfacing (e.g., disengagement) of adjustment-mechanism interface 462 from adjustment mechanism 40. For some applications, lock 444 is actively locked by a force applied thereto by unlocking mechanism 450. However, lock 444 is typically biased to be in its locked state, and so automatically locks upon removal of the pressing force, e.g., by retracting force applicator 466, or by retracting tool 460 as a whole.

In this state, the anatomical and/or functional condition of valve 230 is observed, e.g., using Doppler echocardiography (as illustrated by the inset schematic in FIG. 18H), or another imaging technique, so as to determine whether a desired amount of contraction has been achieved. For example, regurgitation from valve 230 may be observed, so as to determine whether the regurgitation has been sufficiently reduced (e.g., eliminated). Tool 460 may then be returned to adjustment device 442, and readjustment performed (18I).

System 440 facilitates repeated cycles of engagement with, adjustment of, and disengagement from adjustment device 442. It is hypothesized that for some applications, in the absence of the locking of lock 444 before (or upon) each disengagement, structure 222 might return at least partway toward its previous shape or size. For example, in the absence of this locking, a tendency of the native annulus to return toward its previous circumference might otherwise cause contraction member 226 to unspool from adjustment mechanism 40 each time that adjustment-mechanism interface 462 disengages from the adjustment mechanism. Additionally, the independence between (i) the decoupling of guide member 86 from adjustment device 442, and (ii) the unlocking and locking of lock 444 further facilitates repeated retraction and re-engagement of tool 460. Together, these features facilitate (i) post-adjustment observation of the condition of valve 230 in the absence of force applied to the valve and/or to structure 222 by tool 460, and (ii) subsequent readjustment of the implant at least in part responsively to that observation.

Once a desired amount of adjustment has been achieved, tool 460 is used to decouple adapter 446 (and thereby guide member 86) from adjustment device 442. Typically, this is achieved by (i) rotating adapter 446 (e.g., by applying torque to trunk 452) using adapter interface 464, while (ii) providing a reference force to adjustment device 442 (e.g., holding driving interface 476 still) using adjustment-mechanism interface 462, thereby decoupling (e.g., unscrewing) fastener 448 from the adjustment device (FIG. 18J). Tool 460 and guide member 86 are then withdrawn from the subject (FIG. 18K).

For some applications, adapter 446 (and thereby guide member 86) are not decoupled from adjustment device 442 at the end of the procedure, and a proximal end of guide member 86 remains accessible from outside the body, e.g., using a port. For such applications, adjustment mechanism 40 may be accessed and readjusted during a subsequent procedure.

Reference is made to FIGS. 19A-F, which are schematic illustrations of a force gauge 500, and techniques for use thereof, in accordance with some applications of the invention. It is hypothesized that for some applications it is advantageous to test the anchoring strength of individual anchors subsequent to their anchoring, and prior to anchoring of a subsequent anchor. For some applications this is achieved using a force gauge such as force gauge 2800 described in PCT application publication WO 2014/064694, which is incorporated herein by reference in its entirety. For some applications, and as described with reference to FIGS. 19A-F, this is achieved using force gauge 500.

A method is described, comprising: (1) using implant-manipulating handle 126, coupled to structure 222 (via reference-force tube 19), to percutaneously advance structure 222 toward the implant site (e.g., as described hereinabove); (2) by applying a first force to the implant-manipulating handle, sliding the implant with respect to catheter 14 without causing the implant to apply force to tissue at the implant site (FIG. 19B); (3) measuring a magnitude of the first force (FIG. 19B); (4) subsequently, anchoring the implant to tissue at the implant site (FIG. 19E); (5) subsequently, by applying a second force to the implant-manipulating handle, causing the implant to apply a third force to tissue at the implant site via the anchoring of the implant (FIG. 19F); (6) measuring a magnitude of the second force; and (7) determining a magnitude of the third force at least in part responsively to a difference between the magnitude of the first force and the magnitude of the second force.

Force gauge 500 is provided on handle 126, and is coupled to structure 222 via reference-force tube 19. Gauge 500 indicates the strength of a force (e.g., a pulling force) applied to structure 222 via the gauge. For some applications, and as shown, gauge 500 comprises a grip 502, which facilitates applying the force to structure 222 using handle 126 in a similar manner to if the gauge were absent.

Figure 19A:
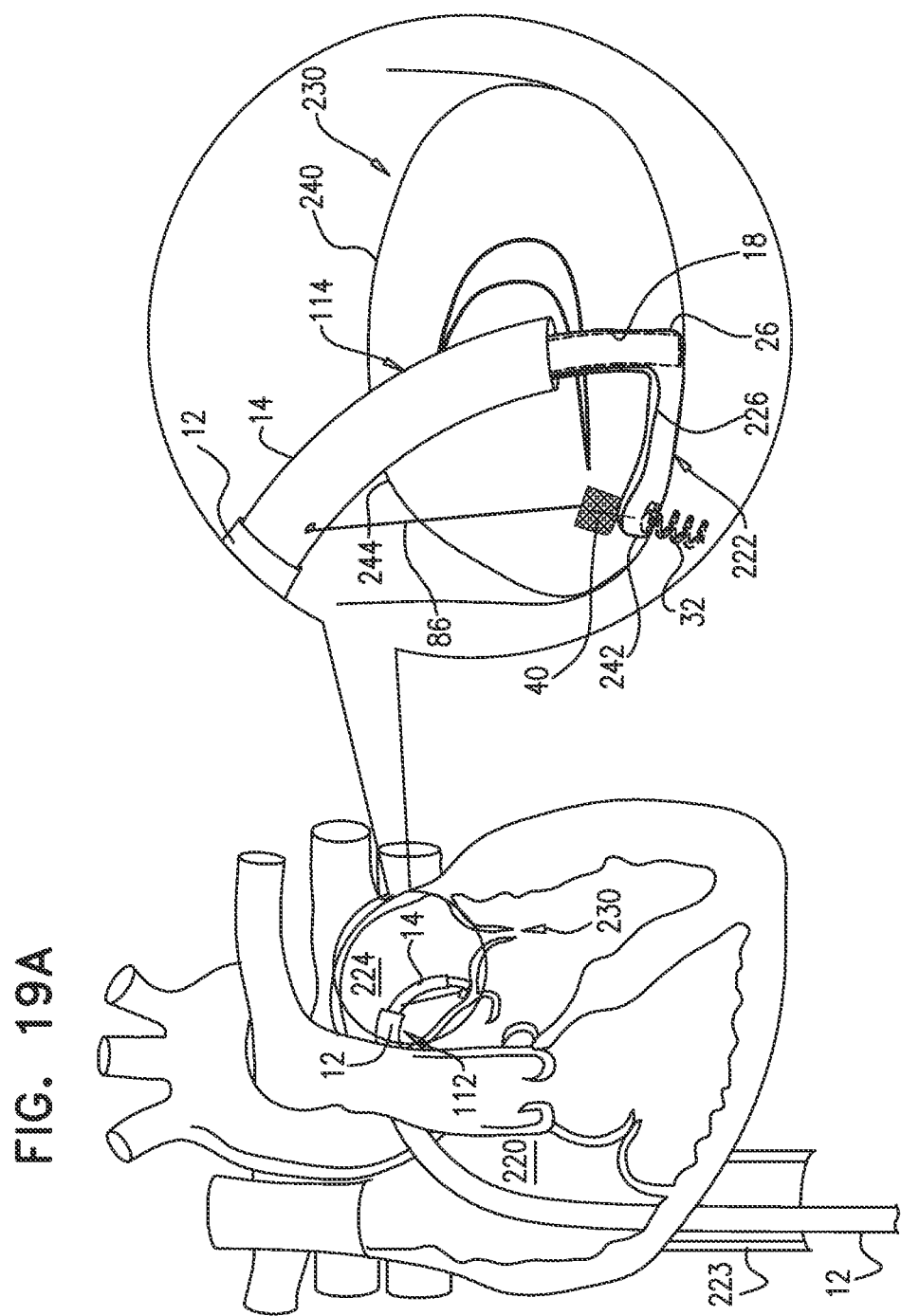
Figure 19B:
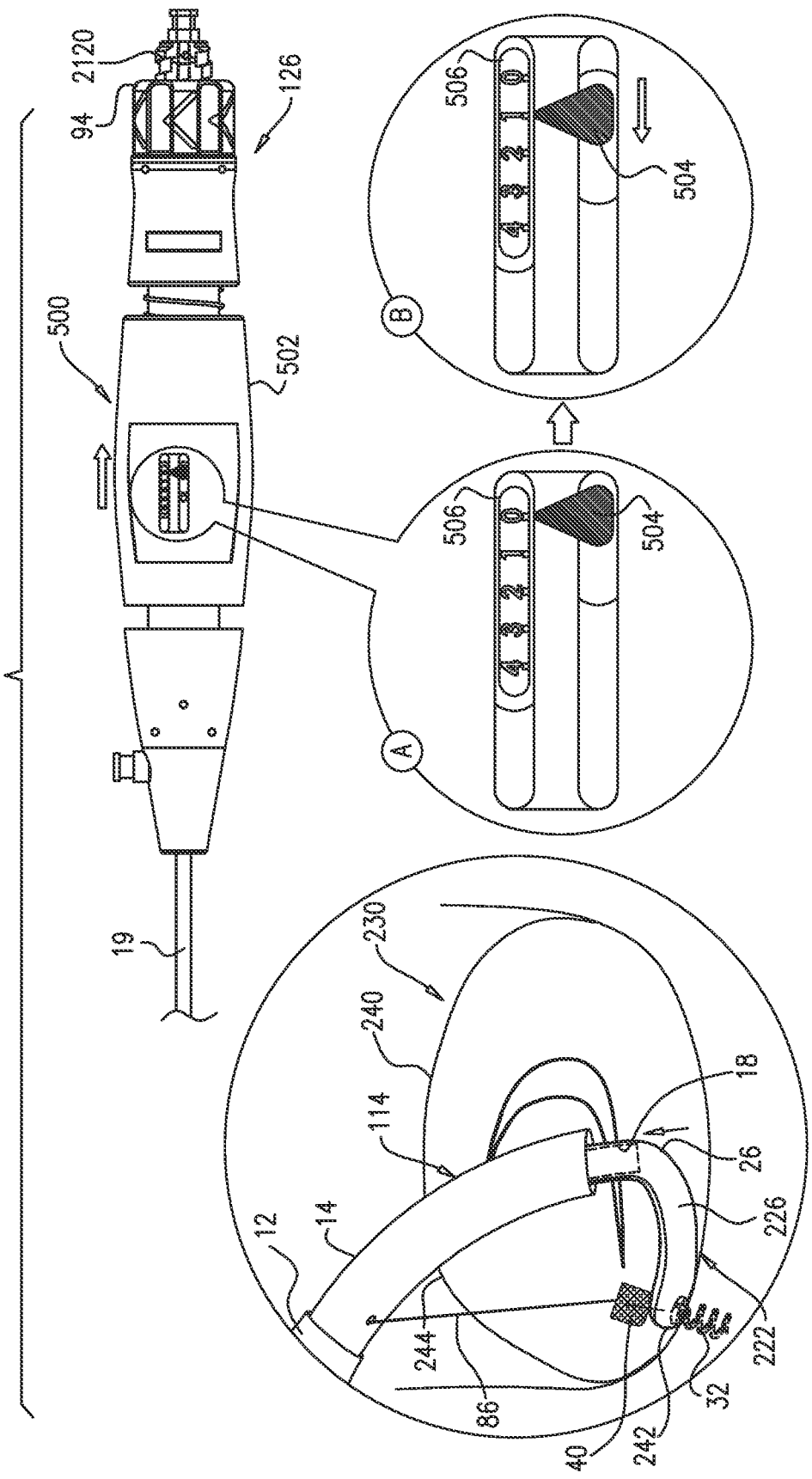

FIG. 19A shows a state of structure 222 being implanted at valve 230, in which (i) a first anchor 32 has been used to anchor the distal end of sleeve 26 to annulus 240, (ii) a successive portion of sleeve 26 has been freed from channel 18, and (iii) channel 18 is in position to anchor a second anchor, sandwiching sleeve 26 against the tissue. The state shown in FIG. 19A is typically the same as that shown in FIG. 3D, mutatis mutandis.

Prior to anchoring the second anchor, structure 222 is slid with respect to catheter 14 by applying a force via grip 502, without causing the implant to apply force to tissue at the implant site. FIG. 19B shows grip 502 being pulled proximally such that reference-force tube 19 (and thereby a proximal portion of sleeve 26, which is coupled thereto) and channel 18 (disposed through tube 19) are together pulled proximally. (Tube 19 and channel 18 do not move with respect to each other because knob 94 remains stationary.) The pulling is typically stopped as soon as movement of handle 126 is observed, and the portion of sleeve 26 disposed between channel 18 and the first anchor is typically not tensioned, therefore structure 222 is not caused to apply force to the tissue. The force required to cause handle 126 to move proximally is measured using an indicator 504 of gauge 500. Indicator 504 is typically a peak force indicator, which continues to indicate the maximum force experienced when that force is no longer present. Frame (i) of FIG. 19B shows indicator 504 indicating "0" on a scale 506, prior to pulling on grip 502, and frame (ii) shows indicator 504 indicating "1" on scale 506, subsequent to pulling on the grip.

Because no force is applied to the tissue (e.g., because the portion of sleeve 26 disposed between channel 18 and the first anchor is not tensioned), the measured force is indicative of friction between (i) tube 19 (and in some cases a proximal portion of sleeve 26), and (ii) catheter 14. Such friction is typically present in transcatheter systems, and for some applications, as described hereinabove, such friction is intentionally provided so as to reduce a likelihood of inadvertent sliding of tube 19 through catheter 14. Typically, the force required to overcome static friction (i.e., that required to initiate the sliding of the implant) is greater than that required to overcome kinetic friction (i.e., that required to maintain sliding of the implant). Therefore measurement of the force is possible even if the pulling is stopped as soon as movement of handle 126 is observed. This therefore facilitates avoiding applying force to the tissue via structure 222 (which (i) might otherwise occur if a greater degree of movement were required, and (ii) would interfere with measurement of friction alone).

As described hereinabove, the force used to slide the implant without causing the implant to apply force to the tissue is subsequently compared with a force used to apply force to the tissue via the previously-implanted anchor (FIG. 19F). The result of this comparison is indicative of the magnitude of the net force applied to the anchor via sleeve 26 (i.e., the total force applied, minus the force required to overcome friction). Successfully pulling on the anchor with a force greater than a pre-determined threshold force, without the anchor becoming de-anchored, is indicative of successful anchoring of the anchor. Gauge 500 facilitates accurately identifying that the pre-determined threshold force has been achieved, thereby allowing the operator not to pull harder than is necessary to identify this. Gauge 500 therefore reduces the likelihood of applying an unnecessarily strong pulling force to the anchor via sleeve 26.

FIGS. 19B-C show an application of the invention for facilitating the comparison of the pre- and post-anchoring forces. For such an application, scale 506 is zeroable (e.g., resettable). Once the pre-anchoring force is measured (FIG. 19B), scale 506 is zeroed to the value indicated by peak indicator 504. This is shown by the sliding of scale 506 in FIG. 19C, but it to be noted that the scope of the present invention includes other techniques for zeroing a scale. Therefore, the indicated post-anchoring force shown in FIG. 19F is the net force applied to the anchor via sleeve 26, ignoring the force required to overcome friction.

For some applications, a force gauge is alternatively or additionally provided on a proximal portion of anchor driver 36 (not shown). In this case, the anchor could be pulled directly, rather than via sleeve 26. However, for applications in which channel 18 remains sandwiching sleeve 26 against the tissue until after anchor driver 36 is decoupled from anchor 32 (e.g., illustrated by FIG. 3C and step (A) of FIG. 4A, in sequence), resistance to the pulling may disadvantageously be provided the channel, making accurate measurement difficult. For some applications in which channel 18 is withdrawn prior to decoupling of anchor driver 36 from anchor 32 (e.g., illustrated by FIG. 3C and step (A) of FIG. 4B, in sequence), this disadvantage may not apply.

FIGS. 19A-F show the measured force as a pulling force. However for some applications, the measured force (or at least one measured force) is a pushing force. It is hypothesized that for some applications the resistance (e.g., friction) between (i) tube 19 (and optionally part of sleeve 26) and (ii) catheter 14 is generally equal in either axial direction. For some such applications, the pre-anchoring measured force is a pushing force, which is used in the same way, mutatis mutandis, to determine the net force applied to the anchor. It is hypothesized that for some applications this advantageously facilitates measurement of the pre-anchoring force during the movement of channel 18 and sleeve 26 toward the anchoring site (e.g., illustrated by the transition from step B to step C of FIGS. 4A and 4B), thereby shortening the overall procedure by eliminating the step shown in FIG. 19B.

Alternatively or additionally, such measurement of resistance to a pushing force may be used to confirm successful positioning of the distal end of channel 18 against tissue. For example, distal movement of the distal end of channel 18 (and/or if handle 126) before the applied pushing force reaches a particular threshold, may indicate that channel 18 was placed against weaker tissue (e.g., leaflet tissue), whereas higher resistance may indicate that the tube was placed against stronger tissue (e.g., annulus 240, or a fibrous trigone).

Figure 20:
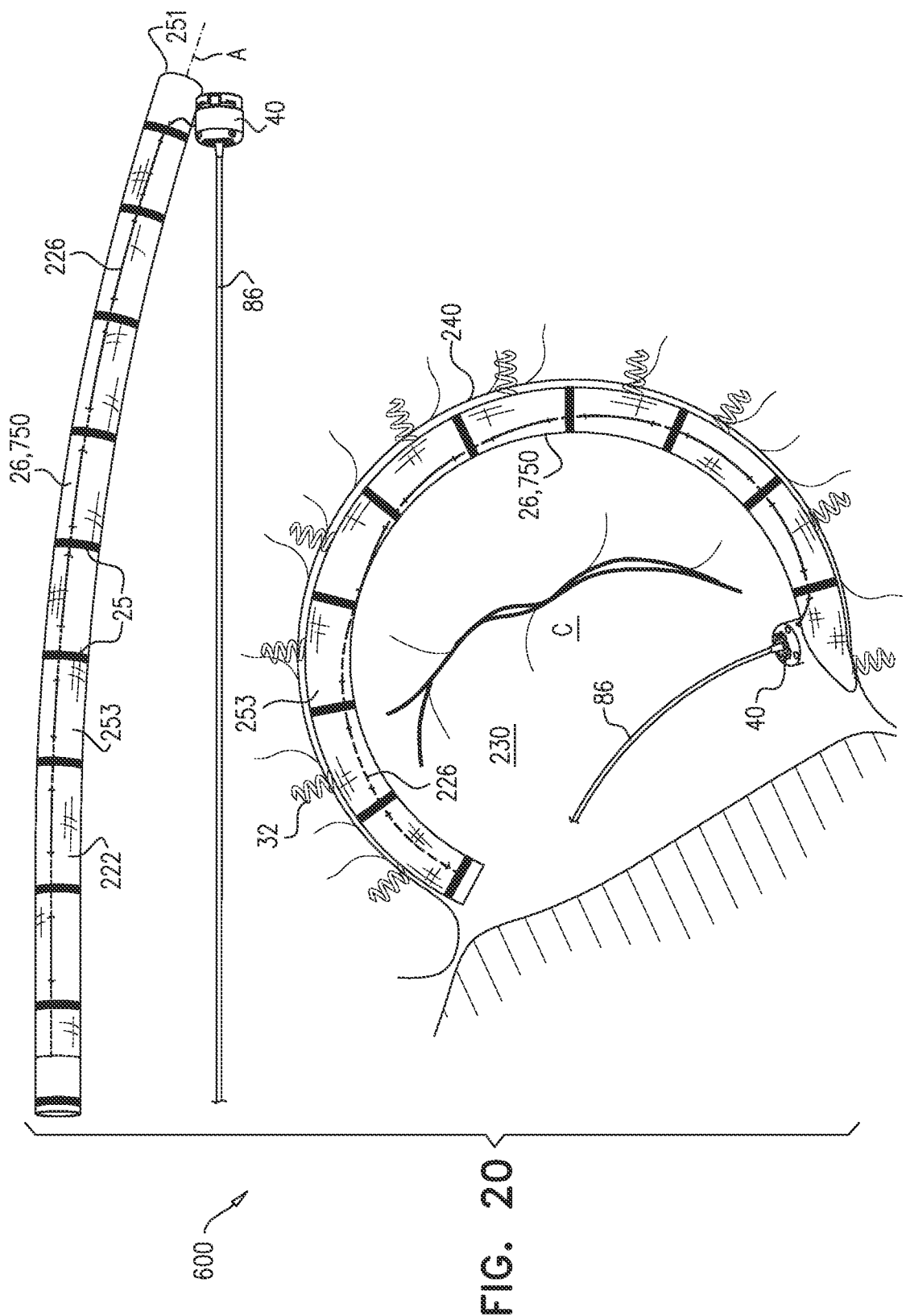
FIG. 20 is a schematic illustration of an annuloplasty structure in a delivery and implanted state, in accordance with some applications of the invention.

Reference is now made to FIG. 20, which is a schematic illustration of a system 600 comprising an implant configured for delivery into a heart of a subject, in accordance with some applications of the present invention. The implant comprises annuloplasty ring structure 222 (i.e., an implant, e.g., an annuloplasty band) comprising flexible sleeve 26 (as described hereinabove with reference to FIG. 1). As described hereinabove, structure 222 comprises contraction member 226 that extends along sleeve 26.

As shown in the lower image of FIG. 20, during anchoring of sleeve 26 along the circumference of annulus 240, with each successive deployment of anchors 32, sleeve 26 gets successively twisted helically around its longitudinal axis at the point of entry of each successive anchor 32. That is, with each successive deployment of anchor 32, tension and torsion of sleeve 26 increases as it is positioned circumferentially around annulus 240. Since contraction member 226 is threaded through sleeve 26, as the sleeve twists, the twist and torsion of sleeve 26 causes contraction member 226 to assume a helical path with respect to the tissue of annulus 240. In response to twisting of the sleeve, parts of contraction member 226 are disposed further away from the tissue (i.e., the parts of member 226 at the parts of sleeve 26 that are positioned first against the annulus), while other parts of contraction member 226 are disposed closer to the tissue of annulus 240 (i.e., the parts of member 226 at the parts of sleeve 26 that are positioned later against the annulus, after the sleeve assumes a curved shape corresponding to the curve of the annulus 240). Thus, the twisting of some parts of sleeve 26, for a given part of the sleeve 26, a part of contraction member 226 is brought in line with and against tissue of annulus 240, and in some cases, in the path of anchor 32 passing through that part of sleeve 26. In such a case, the part of contraction member 226 is likely to become entangled with anchor 32 passing through that part of sleeve 26, and ultimately, compromising the smooth tensioning of contraction member 226 in response to actuation of adjustment mechanism 40. For some applications, the entangling of contraction member 226 with anchor 32 increases friction between the part of contraction member 226 and the part of sleeve 26.

Figure 21:
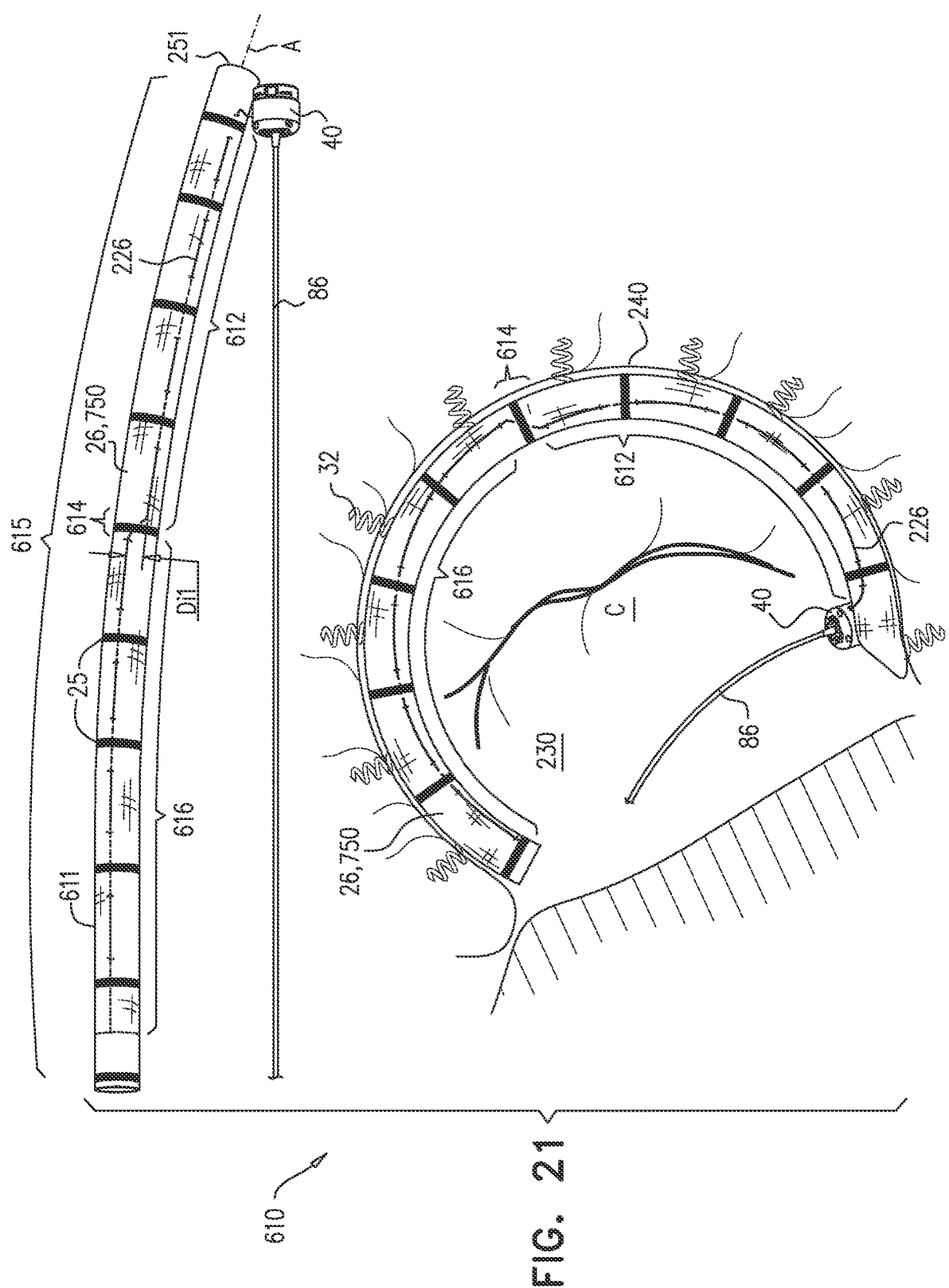
FIG. 21 is a schematic illustration of an annuloplasty structure in a delivery and implanted state showing a contraction member having an offsetting region, in accordance with some applications of the invention.

Reference is now made to FIG. 21, which is a schematic illustration of a system 610 comprising an implant configured for delivery into a heart of a subject, in accordance with some applications of the present invention. The implant comprises annuloplasty ring structure 611 (i.e., an implant, e.g., an annuloplasty band) comprising a flexible sleeve 26 defining a primary body portion 750 of structure 611. It is to be noted that annuloplasty structure 611 is similar to structure 222 as described throughout the application and specifically, hereinabove with reference to FIG. 1, with the exception of the coupling of contraction member 226 with respect to sleeve 26, as is described hereinbelow.

Contraction member 226 of structure 611 has a first end portion that is coupled to adjustment mechanism 40 and a second end portion that is coupled to a portion of a body portion 615 of structure 611. Member 226 defines a first longitudinal portion 612 extending from the first end portion and through a contracting portion of body portion 615 of structure 611. First longitudinal portion 612 extends along a first longitudinal path. For some applications, the first longitudinal path is parallel with respect to a longitudinal axis of body portion 615 when structure 611 assumes a linear shape and when structure 611 is in a state in which no torsion or twisting is applied to sleeve 26. For some applications of the present invention, and as shown in FIG. 21, body portion 615 comprises sleeve 26. Member 226 also defines a second longitudinal portion 616 extending through the contracting portion of body portion 615 of structure 611 and to the second end portion of member 226. Second longitudinal portion 616 extends along a second longitudinal path that is offset with respect to the first longitudinal path when structure 611 is in a state in which no torsion or twisting is applied to sleeve 26. For some applications, the second longitudinal path is parallel with respect to a longitudinal axis of body portion 615 when structure 611 assumes a linear shape. Additionally, member 226 defines an offsetting portion 614 which offsets first and second longitudinal portions 612 and 616 of contraction member 226.

For some applications of the present invention, offsetting portion 614 extends along a stepped path when structure 611 is in a state in which no torsion or twisting is applied to sleeve 26. For some applications of the present invention, offsetting portion 614 extends along a helical path. For some applications of the prevent invention, contraction member 226 is coupled to sleeve 26 in a manner in which at least a part of contraction member 226 is disposed helically around longitudinal axis A of sleeve 26 of structure 222. For some applications, portion 614 defines at least between 1-5%, e.g., between 1-2%, of contraction member 226 that is disposed helically around longitudinal axis A.

For some applications, and as shown in FIG. 21, body portion 615 of annuloplasty structure 611 comprises is tubular and first and second longitudinal portions 612 and 616 are offset by a distance Di1 of 0.3-0.7 radians, e.g., 0.5 radians. For some applications, first and second longitudinal portions 612 and 616 are offset by a distance of 0.8-1.2 mm, e.g., 1 mm.

For some applications of the present invention, first and second longitudinal portions 612 and 616 and offsetting portion 614 are threaded in and out of a woven material of sleeve 26.

Sleeve 26, for some applications, comprises a flexible tubular wall that circumscribes a central longitudinal axis of sleeve 26 when structure 611 assumes a linear shape. Sleeve 26 has a lumen having a distal end (i.e., at end wall 251 of sleeve 26), a proximal end, and a length therebetween. Contraction member 226 is coupled to sleeve 26 such that tensioning contraction member 226 reduces a length of the lumen. Contraction member 226 is woven, or threaded, through the lateral wall such that, in an absence of torsion of the sleeve around the longitudinal axis, as shown in the upper image of FIG. 21, at least part of contraction member 226 is disposed helically around the longitudinal axis.

Once sleeve 26 is curved to correspond to the shape of annulus 240, sleeve 26 is naturally twisted during the curving, as described hereinabove with reference to FIG. 20. Even during and following the twisting of sleeve 26, offsetting portion 614 enables second longitudinal portion 616 of member 226 to either (1) face the atrium and/or (2) face a center C of structure 611 following the curving of structure 611 to correspond to the shape of annulus 240. As such, portion 616 is positioned away from the portion of sleeve 26 that is against the tissue of annulus 240 and away from any path of anchor 32 that passes through the portion of sleeve 26 that is against the tissue of annulus 240.

Additionally, since offsetting portion 614 enables second longitudinal portion 616 of member 226 to either face center C of structure 611 following the curving of structure 611 to correspond to the shape of annulus 240, contraction member 226 extends more uniformly along the inner wall of sleeve 26 facing center C, once structure 611 is curved to correspond to the shape of the annulus. That is, portion 616 is not disposed helically with respect to the tissue, nor is any section of portion 616 disposed against tissue of annulus 240. With this more uniform extending of member 226 along the inner wall of sleeve 26 facing center C, once structure 611 is curved to correspond to the shape of the annulus, contraction member 226 is able to more uniformly radially contract structure 611, since the force of member 226 is distributed more evenly along the curved path of sleeve 26 from the inner wall of sleeve 26 facing center C, once structure 611 is curved to correspond to the shape of the annulus.

Additionally, once structure 611 is curved to correspond to the shape of the annulus, offsetting portion 614 enables structure to assume a configuration in which the entire contraction member 226 is disposed along an inner perimeter of structure 611 (i.e., facing center C) and not along any portion of the outer perimeter of structure 611. As such, the configuration prevents entangling of member 226 with any anchor that is anchored through sleeve 26 at the outer perimeter of structure 611, as described hereinabove, for example, with reference to FIGS. 3A-G and 4A-B.

It is to be noted that the coupling of member 226 to sleeve 26 of structure 611 in the helical orientation such that member 226 defines portions 612, 614, and 616, may be applied to any annuloplasty structure 222 described herein. Additionally, it is to be noted that any system described herein for use with annuloplasty structure 222 may be used in combination with annuloplasty structure 611.

Figure 22A:
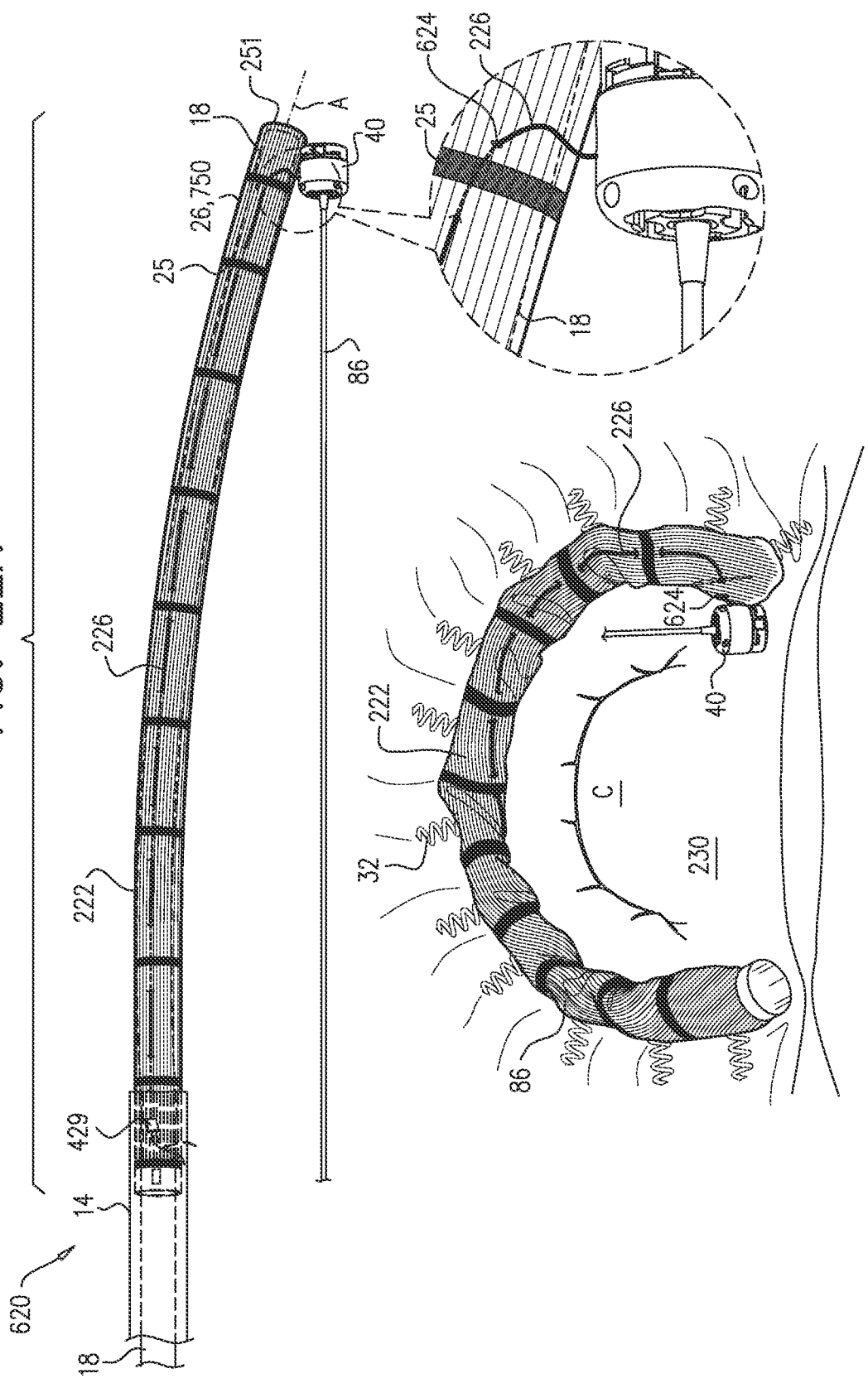
Figure 22C:
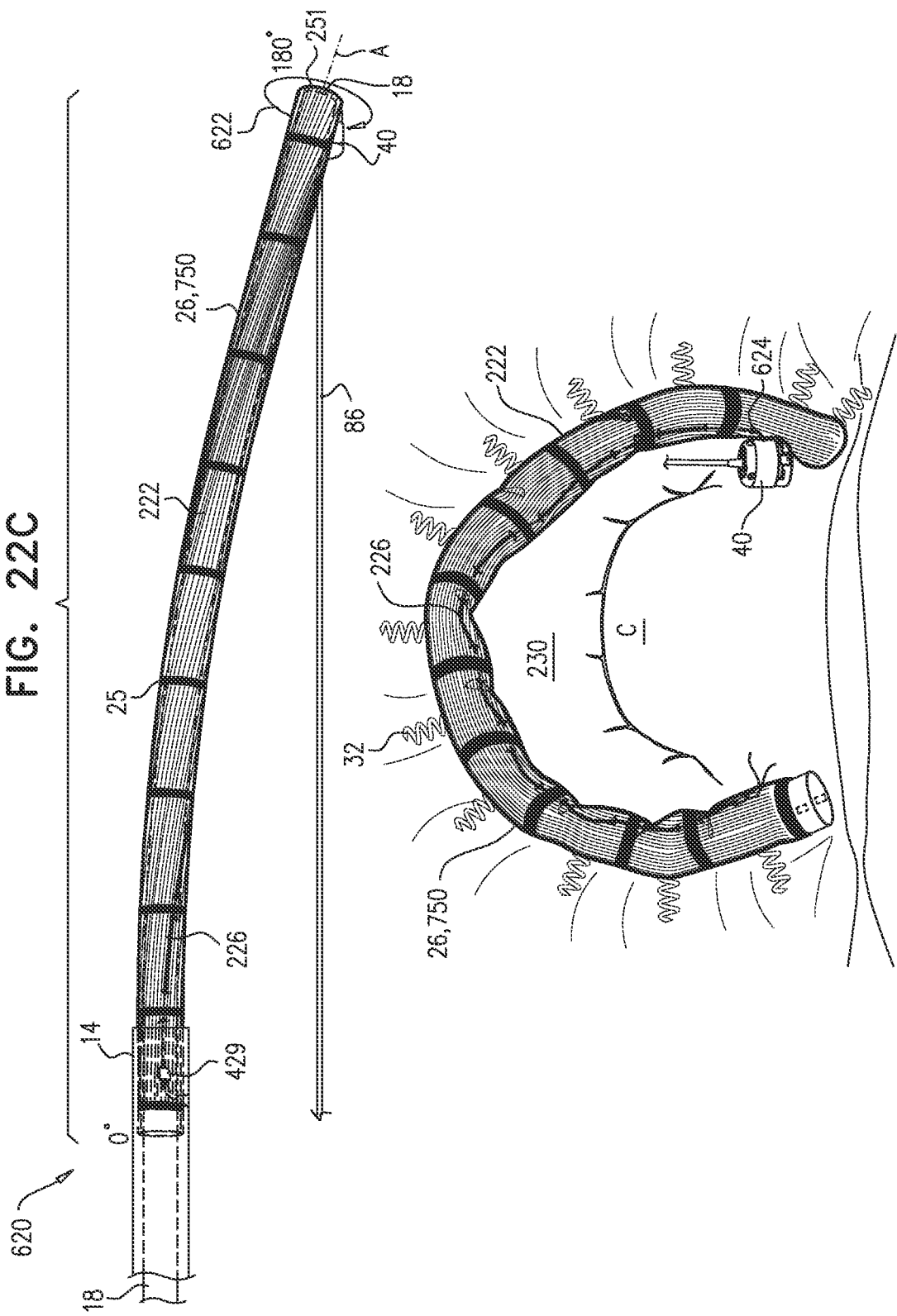

Reference is now made to FIGS. 22A-C, which are schematic illustrations of a system 620 comprising an implant configured for delivery into a heart of a subject, in accordance with some applications of the present invention. The implant comprises annuloplasty ring structure 222 (i.e., an implant, e.g., an annuloplasty band) comprising flexible sleeve 26 (as described hereinabove with reference to FIG. 1) defining a primary body portion 750 of structure 222.

FIG. 22A is similar to FIG. 20, as described hereinabove, with the exception that sleeve 26 of structure 222 is shown as being twisted even more than sleeve 26 of FIG. 20 such that a portion of contraction member 226 is disposed on the underside of structure 222 once structure 222 is curved to correspond to the curved shape of annulus 240. In such a manner, during anchoring of anchors 32 through the portion of sleeve 26 that is twisted, it is possible that anchors 32 can entangle with the portion of contraction member 226 that is disposed adjacent to the tissue of annulus 240. Additionally, in the twisted state of sleeve 26, contraction member 226 is not uniformly and consistently disposed along the inner wall of sleeve 26 facing center C, once structure 222 is curved to correspond to the shape of the annulus. As will be described hereinbelow with reference to FIGS. 22B-C, in order to prevent any portion of contraction member 226 being disposed adjacent the tissue of the annulus which is shown in FIG. 22A, prior to delivery of structure 222, sleeve 26 is actively twisted around a central longitudinal axis A of channel 18 disposed within sleeve 26 and when sleeve 26 assumes a linear shape and/or structure 222 is rotated around axis A.

Typically, second end 429 of contraction member 226 (i.e., the end not coupled to adjustment mechanism 40) is fixedly coupled to sleeve 26 (e.g., using a crimp bead, as shown). As shown in FIG. 22A, in the upper image, in a resting state of structure 222, second end 429 of contraction member 226 is at a distance of between 0 and 0.25 radians from a location 624 along sleeve 26 at which contraction member 226 exits away from sleeve 26 and to adjustment mechanism 40. In the resting state, as shown in the upper image of FIG. 22A, an angle of twist between second end 429 of contraction member 226 and location 624 is between 0 and 10 degrees.

FIG. 22B shows structure 222 being actively twisted about longitudinal axis A of channel 18. In the twisted state, as shown in the upper image of FIG. 22B, second end 429 of contraction member 226 is at a distance of between 2.5 and 3.5 radians from location 624 along sleeve 26 at which contraction member 226 exits away from sleeve 26 and to adjustment mechanism 40. In the twisted state, as shown in the upper image of FIG. 22B, an angle of twist between second end 429 of contraction member 226 and location 624 is between 170 and 190 degrees, e.g., 180 degrees.

As described throughout the application, and specifically, hereinabove with reference to FIGS. 1-2, structure 222 is advanced within catheter 14. Channel 18 is disposed within the lumen of structure 222. As shown in FIGS. 22B-C, structure 222 comprises flexible sleeve 26 that defines a lumen having a proximal end, a distal end, and a central longitudinal axis therebetween. Structure 222 is longitudinally slidable through catheter 14 while sleeve 26 is twisted about the axis of sleeve 26 and about axis A of channel 18. Channel 18 is longitudinally slidable through catheter 14 while flexible sleeve 26 of the structure 222 encases a distal portion of channel 18 while twisted about the axis of the sleeve. Structure 222 is longitudinally slidable through catheter 14 with channel 18, while sleeve 26 encases the distal portion of channel 18 while sleeve 26 twisted about the axis of sleeve 26.

For some applications of the present invention, sleeve 26 is twisted such that an angle of twist between the proximal end and the distal end is 170-190 degrees, e.g., 180 degrees. That is, adjustment mechanism 40 is twisted from second end 429 of contraction member 226 at an angle of twist between 140-180 degrees, e.g., between 155 and 175 degrees.

During the placement of sleeve 26 around annulus 240, successive portions of sleeve 26 are progressively released off channel 18, as described hereinabove. As the successive portions of sleeve 26 are released off channel 18, the angle of twist of sleeve 26 naturally and passively becomes reduced in a manner in which contraction member 226 is disposed facing center C of valve 230.

Additionally, once structure 222 is curved to correspond to the shape of the annulus, as shown in the lower image of FIG. 22B, the active twisting of sleeve 26 prior to delivery followed by the reducing of the angle of twist during the releasing of sleeve 26, enables structure 222 to assume a configuration in which the entire contraction member 226 is disposed along an inner perimeter of structure 222 (i.e., facing center C) and not along any portion of the outer perimeter of structure 222. As such, the configuration pre- vents entangling of member 226 with any anchor that is anchored through sleeve 26 at the outer perimeter of structure 222, as described hereinabove, for example, with reference to FIGS. 3A-G and 4A-B.

FIG. 22C shows structure 222 being rotated around central longitudinal axis A of channel 18 while sleeve 26 is twisted, as described hereinabove with reference to FIG. 22B. When structure 222 is rotated around central longitudinal axis of channel 18 in a first rotational direction as indicated by arrow 622, and when the distal end of sleeve 26 is distal to a distal end of catheter 14, adjustment mechanism 40 adjacent a first location of sleeve 26 corresponding to a first point along a perimeter of a distal end of channel 18, as shown in the upper image of FIG. 22C.

Additionally, once structure 222 is curved to correspond to the shape of the annulus, the rotating of sleeve 26 prior to delivery followed by the reducing of the angle of twist during the releasing of sleeve 26, enables structure 222 to assume a configuration in which the entire contraction member 226 is disposed along an inner perimeter of structure 222 (i.e., facing center C) and not along any portion of the outer perimeter of structure 222. As such, the configuration prevents entangling of member 226 with any anchor that is anchored through sleeve 26 at the outer perimeter of structure 222, as described hereinabove, for example, with reference to FIGS. 3A-G and 4A-B.

Reference is now made to FIGS. 22B-C. For some applications of the present invention, only sleeve 26 is twisted about axis A, as shown in FIG. 22B while structure 222 is not rotated around axis A as shown in FIG. 22C. For some applications of the present invention, sleeve 26 is twisted about axis A, as shown in FIG. 22B and structure 222 is rotated around axis A as shown in FIG. 22C.

Reference is now made to FIGS. 21 and 22A-C. It is to be noted that structure 611 described hereinabove with reference to FIG. 21 may be used in place of structure 222 shown in FIGS. 22A-C.

Figures 23A, 23B:
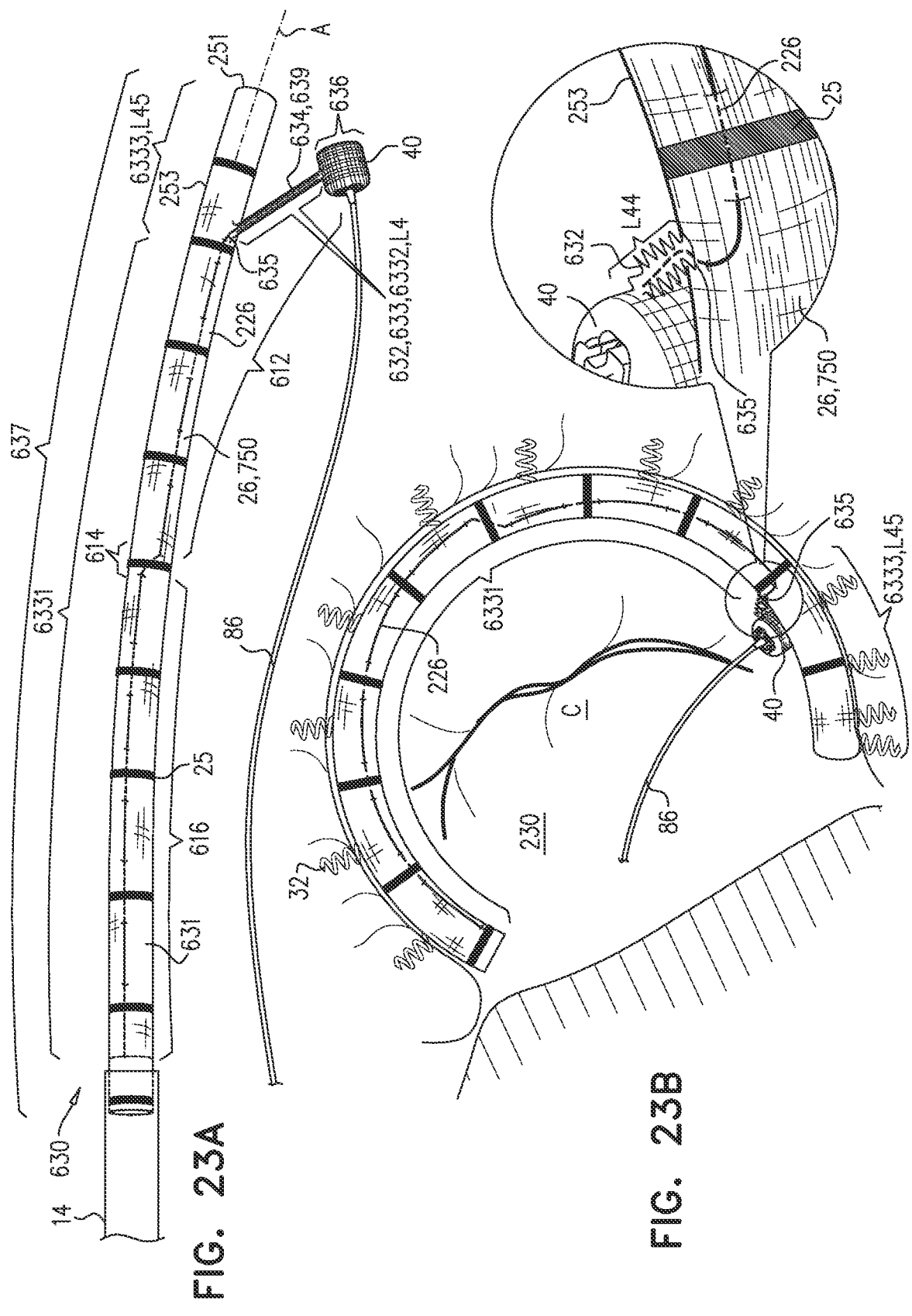
FIGS. 23A-B are schematic illustrations of an annuloplasty structure comprising a primary and secondary sleeve, in accordance with some applications of the invention.

Reference is now made to FIGS. 23A-B, which are schematic illustrations of a system 630 comprising an implant configured for delivery into a heart of a subject, in accordance with some applications of the present invention. The implant comprises annuloplasty ring structure 631 (i.e., an implant, e.g., an annuloplasty band) comprising a flexible sleeve 26. It is to be noted that annuloplasty structure 631 is similar to structure 611 as described hereinabove with reference to FIG. 21, with the exception of structure 631 comprising a contraction-member-protecting element 633. Sleeve 26 defines a primary body portion 750 of annuloplasty structure 631.

Contraction member 226 defines (1) a first portion 6331 that extends along a contracting portion of sleeve 26 and extends away from sleeve 26 at a connection point 635, and (2) a second portion 6332 which extends away from sleeve 26 and to adjustment mechanism 40. Contraction-member-protecting element 633 protects second portion of 6332 since portion 6332 is disposed outside of wall 253 of sleeve 26 and away from sleeve 26. Additionally, element 633 provides a path along which portion 6332 slides during the tensioning and pulling of contraction member 226. This path provided by element 633 prevents entangling of portion 6332 during the tensioning and pulling of contraction member 226.

Additionally, contraction-member-protecting element 633 protects second portion of 6332 from any tool that is placed in proximity of the implant. In particular, contraction-member-protecting element 633 protects second portion of 6332 by at least mostly covering portion 6332.

As shown in FIGS. 23A-B, contraction-member-protecting element 633 comprises a contraction-member-protecting element sleeve 634 defining a lumen therethrough, and second portion 6332 of contraction member 226 is disposed within the secondary lumen and extends to adjustment mechanism 40. Thus, sleeve 26 of structure 631 defines a primary sleeve 637, while contraction-member-protecting element sleeve 634 defines a secondary sleeve 639 defining a secondary lumen therethrough, and second portion 6332 of contraction member 226 is disposed within the secondary lumen of secondary sleeve 639 and extends to adjustment mechanism 40. Secondary sleeve 639 functions as a connector to couple adjustment mechanism 40 to primary sleeve 637 of structure 631.

For some applications of the present invention, secondary sleeve 639 functions as connector 27 described hereinabove with reference to FIG. 1.

For some applications of the present invention, sleeve 634 comprises the same material as sleeve 26, as described hereinabove with reference to FIG. 1. For some applications of the present invention, sleeve 634 covers adjustment mechanism 40. For some applications of the present invention, the sleeve 26, sleeve 634, and the fabric covering adjustment mechanism 40 are fabricated from the same material. For some applications of the present invention, the sleeve 26, sleeve 634, and the fabric covering adjustment mechanism 40 are fabricated from a single piece (i.e., structure 631 is entirely encased in fabric except for the proximal opening in sleeve 26).

Contraction-member-protecting element 633 has (1) a first end that is coupled to a primary body portion 750 (i.e., sleeve 26) of the structure 631, and (2) a second end that is coupled to adjustment mechanism 40. Contraction member 226 extends from adjustment mechanism 40 via contraction-member-protecting element to primary body portion 750 (i.e., sleeve 26) of structure 631. Contraction member 226 enters sleeve 26 at connection point 635, then continues to extend along a contracting portion of sleeve 26. That is, structure 631 defines a contracting portion of structure 631 (i.e., the portion of sleeve along which a first portion 6331 of contraction member 226 extends) and a non-contracting portion 6333 (i.e., the part of sleeve 26 along which contraction member 226 does not extend). Typically the non-contracting portion of sleeve 26 comprises the portion of sleeve 26 that is distal to connection point 635 and extends to distal end wall 251. Typically, connection point 635 is at least 10 mm, e.g., at least 15 mm, from any end of structure 631, e.g., connection point 635 is at least 10 mm, e.g., at least 15 mm, from end wall 251. That is, typically, the first end of contraction-member-protecting element 633 is connected to the annuloplasty structure at connection point 635 that is at least 10 mm, e.g., at least 15 mm, from any end of the annuloplasty structure, e.g., from end wall 251, as shown. For some applications of the present invention, connection point 635 is 10-15 mm from end wall 251.

Reference is now made to FIGS. 3A-B and 23A-B. As shown in FIG. 3A, adjustment mechanism 40 advances toward the annulus of the mitral valve distally to the distal end of sleeve 26. In this way, adjustment mechanism 40 is disposed on the longitudinal axis of sleeve 26 (e.g., collinearly with the sleeve), so as to advantageously maintain a small cross-sectional diameter of the implant for transluminal delivery. In FIG. 3B, subsequent to exposure of at least adjustment mechanism 40 (and typically at least end wall 251 of sleeve 26) from catheter 14, the adjustment mechanism is moved away from end wall 251. As shown in FIGS. 23A-B, contraction-member-protecting element 633 facilitates this movement of adjustment mechanism 40 by making mechanism 40 flexibly and/or articulatably coupled to sleeve 26. For some applications, element 633 is tensioned or relaxed to move mechanism 40 with respect to sleeve 26 to reposition mechanism 40. For some applications, guide member 86 is tensioned or relaxed in order to reposition mechanism 40.

Element 633 is connected to sleeve 26 at connection point 635 in order to enable portion 6333 of sleeve 26 to be free of contraction member 226 for a length L45 of between 10-15 mm of portion 6333. That is, during delivery of the annuloplasty structure, mechanism 40 is disposed most-distally followed by portion 6333 which does not have any contraction member 226 threaded therethrough. During delivery, element 633 is disposed alongside portion 6333. Thus, L4 is slightly larger than L45. Once the annuloplasty structure has been contracted, as shown in FIG. 23B, adjustment mechanism 40 is brought adjacent to the outer surface of sleeve 26 at connection point 635.

Contraction-member-protecting element 633 has a longitudinal length L4 of 10-15 mm prior to the tensioning of contraction member 226 when measured along a central longitudinal axis of contraction-member-protecting element 633. As described herein above, prior to adjusting of structure 631 by adjustment mechanism 40, structure 631 is advanced through catheter 12. As structure 631 is advanced through catheter 12, in a delivery state of structure 631, adjustment mechanism 40 is disposed distal to (i.e., in front of) sleeve 26. This configuration is shown in FIG. 3A, which shows the distal part of sleeve 26 and adjustment mechanism 40 disposed distal to the distal part of sleeve 26 immediately following deployment from catheter 12 and exposed from catheter 14, although this configuration is maintained throughout advancement of sleeve 26 and mechanism 40 through catheter 12 in the delivery state of the annuloplasty structure. In this delivery state, contraction-member-protecting element 633 extends from connection point 635 alongside a portion of wall 253 of sleeve 26 to adjustment mechanism 40 disposed distal to sleeve 26. In this way, adjustment mechanism 40 is disposed on the central longitudinal axis of sleeve 26 (e.g., collinearly with the sleeve), so as to advantageously maintain a small cross-sectional diameter of the implant for transluminal delivery.

As shown in FIG. 3A, a distal-most portion of contraction member 226 is disposed distally to the distal end of guide catheter 14 (i.e., a tube) at a first distance from the distal end of the catheter 14, and a portion (i.e., a distal portion) adjustment mechanism 40 is disposed distally to contraction member 226 at a second distance from the distal end of catheter 14 that is greater than the first distance. During initial deployment of catheter 12 from within catheter 12 (i.e., a tube), a distal-most portion of contraction member 226 is disposed distally to the distal end of guide catheter 12 (i.e., a tube) at a first distance from the distal end of the catheter 12, and a portion (i.e., a distal portion) adjustment mechanism 40 is disposed distally to contraction member 226 at a second distance from the distal end of catheter 12 that is greater than the first distance. That is, during the initial deployment of catheter 14 from within catheter 12, a portion of adjustment mechanism 40 (e.g., a distal portion) is disposed distally to the distal end of catheter 12 while contraction member 226 is disposed entirely within catheter 12.

Reference is now made to FIGS. 3B and 23A. Once a distal portion of sleeve 26 is deployed within the atrium of the heart, adjustment mechanism 40 is movable away from body portion 750 and distanced from sleeve 26 (i.e., body portion 750 of structure 631) by a distance of 10-15 mm, e.g., 10 mm, which corresponds to longitudinal length L4, as shown in FIG. 23A. Typically, adjustment mechanism 40 is distanced from the sleeve via second portion 6332 of contraction member 226 and/or as shown, adjustment mechanism 40 is distanced from the sleeve via contraction-member-protecting element 633.

As shown in FIG. 23B, subsequently to the deploying of the distal portion of sleeve 26, structure 631 assumes a deployed state in which mechanism 40 moves closer to connection point 635 and the distance between adjustment mechanism 40 and the body portion 750 of structure 631 (i.e., sleeve 26) is reduced by actuating adjustment mechanism 40 and adjusting the tension of contraction member 226, as shown in FIG. 23B.

As adjustment mechanism 40 is actuated, tension is applied to contraction member 226 as successive portions of member 226 are wound around the spool of mechanism 40. Responsively to the tensioning of member 226, successive portions of primary sleeve 637 contract. Once primary sleeve 637 contracts, secondary sleeve 639 (i.e., contraction-member-protecting element 633) contracts and changes shape as tension is applied to second portion 6332 of contraction member 226. During tensioning of second portion 6332 of contraction member 226, contraction-member-protecting element 633 protects second portion 6332 of contraction member 226.

During the reducing of the distance between adjustment mechanism 40, a length of contraction-member-protecting element 633 is reduced and a shape of contraction-member-protecting element 633 changes. As shown in FIG. 23, contraction-member-protecting element 633 is brought closer to wall 253 of sleeve 26 while being compressed and/or folded, and a portion of element 633 is pressed against wall 253 of sleeve 26 of structure 631. That is, at least a portion of element 633 is pressed against wall 253 of sleeve 26 and element 633 has a pressed longitudinal length L44 of 0.5-1.5 mm, e.g., 1 mm, measured along the longitudinal axis of element 633. As shown in FIG. 23B, the distance between adjustment mechanism 40 and sleeve 26 is smaller than the distance between adjustment mechanism 40 and sleeve 26 corresponding to length L4 shown in FIG. 23A, prior to actuation of adjustment mechanism 40.

As shown in FIG. 23B, once structure 631 is in the deployed state, a plurality of tissue anchors 32 are used to anchor structure 631 to annulus 240. The plurality of tissue anchors 32 comprises (i) at least three tissue anchors 32 disposed at the distal portion of structure 631 (i.e., at non-contracting portion 6333), and (ii) at least one tissue anchor 32 (e.g., a plurality, as shown) is disposed in the contracting portion of structure 631 (i.e., the portion of sleeve along which a first portion 6331 of contraction member 226 extends).

For some applications of the present invention, adjustment mechanism 40 is surrounded by a sheath 636 that is an extension of secondary sleeve 639.

Reference is again made to FIGS. 23A-B. For some applications, contraction-member-protecting element 633 comprises a radiopaque material which functions as an adjustment indicator 632 which provides an indication of the adjustment of contraction member 226 and of the annuloplasty structure. For some applications of the present invention, adjustment indicator 632 functions as a tension indicator which provides an indication of the tension of contraction member 226 and of the annuloplasty structure. As element 633 changes shape according to an increase or a decrease in a degree of tension of contraction member 226 (i.e., portion 6332 passing through sleeve 639), the radiopaque material in element 633 enables element 633 to function as indicator 632. As shown in FIG. 23B, a portion of indicator 632 is pressed against sleeve 26 of structure 631.

Adjustment indicator 632 is typically coupled to a body portion 750 of the implant, for some applications of the present invention. For example, the implant comprises an annuloplasty ring structure having a body portion 750 (e.g., sleeve 26), and indicator 632 is directly coupled to the body portion 750 of the annuloplasty ring structure. As shown, indicator 632 is directly coupled to an external surface of the body portion 750 of the annuloplasty ring structure.

It is to be noted that contraction-member-protecting element 633 may be used in combination with any annuloplasty structure described herein (e.g., structures 222, 611, or any other annuloplasty structure described hereinbelow). It is to be noted that for some applications of the present invention, annuloplasty structures described herein may be provided with or without contraction-member-protecting element 633.

Figures 24A, 24B:
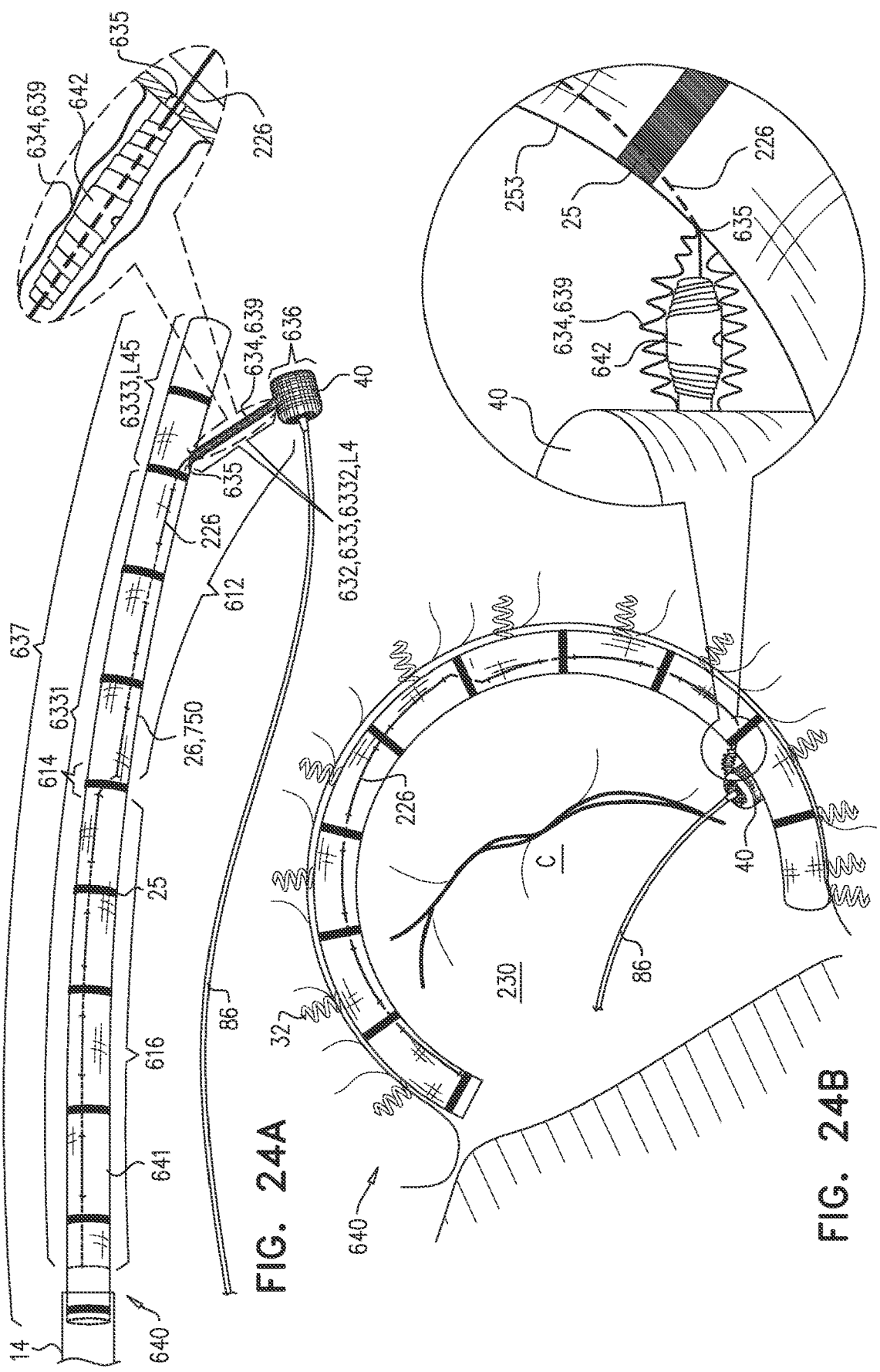
FIGS. 24A-B are schematic illustrations of the annuloplasty structure of FIGS. 23A-B comprising a volute spring, in accordance with some applications of the invention.

Reference is now made to FIGS. 24A-B, which are schematic illustrations of a system 640 comprising an implant configured for delivery into a heart of a subject, in accordance with some applications of the present invention. The implant comprises annuloplasty ring structure 641 (i.e., an implant, e.g., an annuloplasty band) comprising a flexible sleeve 26. It is to be noted that annuloplasty structure 641 is similar to structure 631 as described hereinabove with reference to FIGS. 23A-B, with the exception of structure 641 comprising a spring 642. Sleeve 26 defines a primary body portion 750 of annuloplasty structure 641.

Spring 642 is shaped so as to define a lumen which surrounds second portion 6332 of contraction member 226. For some applications, second portion 6332 extends alongside spring 642. Spring 642 is disposed within contraction-member-protecting element sleeve 634. For some applications of the present invention, spring 642 comprises a telescoping spring, e.g., a volute spring, as shown. It is to be noted that any suitable spring may be positioned within contraction-member-protecting element sleeve 634. For example, a helical spring may be positioned within contraction-member-protecting element sleeve 634.

For some applications of the present invention, spring 642 comprises a radiopaque material such that contraction-member-protecting element 633 functions as adjustment indicator 632. Adjustment indicator 632 is typically coupled to a body portion of the implant, for some applications of the present invention. For example, the implant comprises an annuloplasty ring structure having a body portion (e.g., sleeve 26), and indicator 632 is directly coupled to the body portion of the annuloplasty ring structure. As shown, indicator 632 is directly coupled to an external surface of the body portion of the annuloplasty ring structure.

During the reducing of the distance between adjustment mechanism 40 and sleeve 26, as described hereinabove with reference to FIGS. 23A-B, the length of contraction-member-protecting element 633 is reduced and a shape of contraction-member-protecting element 633 changes. That is, during the reducing of the distance between adjustment mechanism 40 and sleeve 26, spring 642 compresses, as shown in FIG. 24B. During the compressing of spring 642, a shape of spring 642 changes, and thus, the radiopaque material of spring 642 provides an indication of contraction of structure 641. That is, in response to an increase in the degree of tension of contraction member 226 the shape of the radiopaque element of spring 642 changes by compressing spring 642. As shown in FIG. 24B, a portion of indicator 632 is pressed against sleeve 26 of structure 641.

It is to be noted that contraction-member-protecting element 633 and/or spring 642 may be used in combination with any annuloplasty structure described herein (e.g., structures 222, 611, 631, or any other annuloplasty structure described hereinbelow). It is to be noted that for some applications of the present invention, annuloplasty structures described herein may be provided with or without contraction-member-protecting element 633.

Figures 25A, 25B:
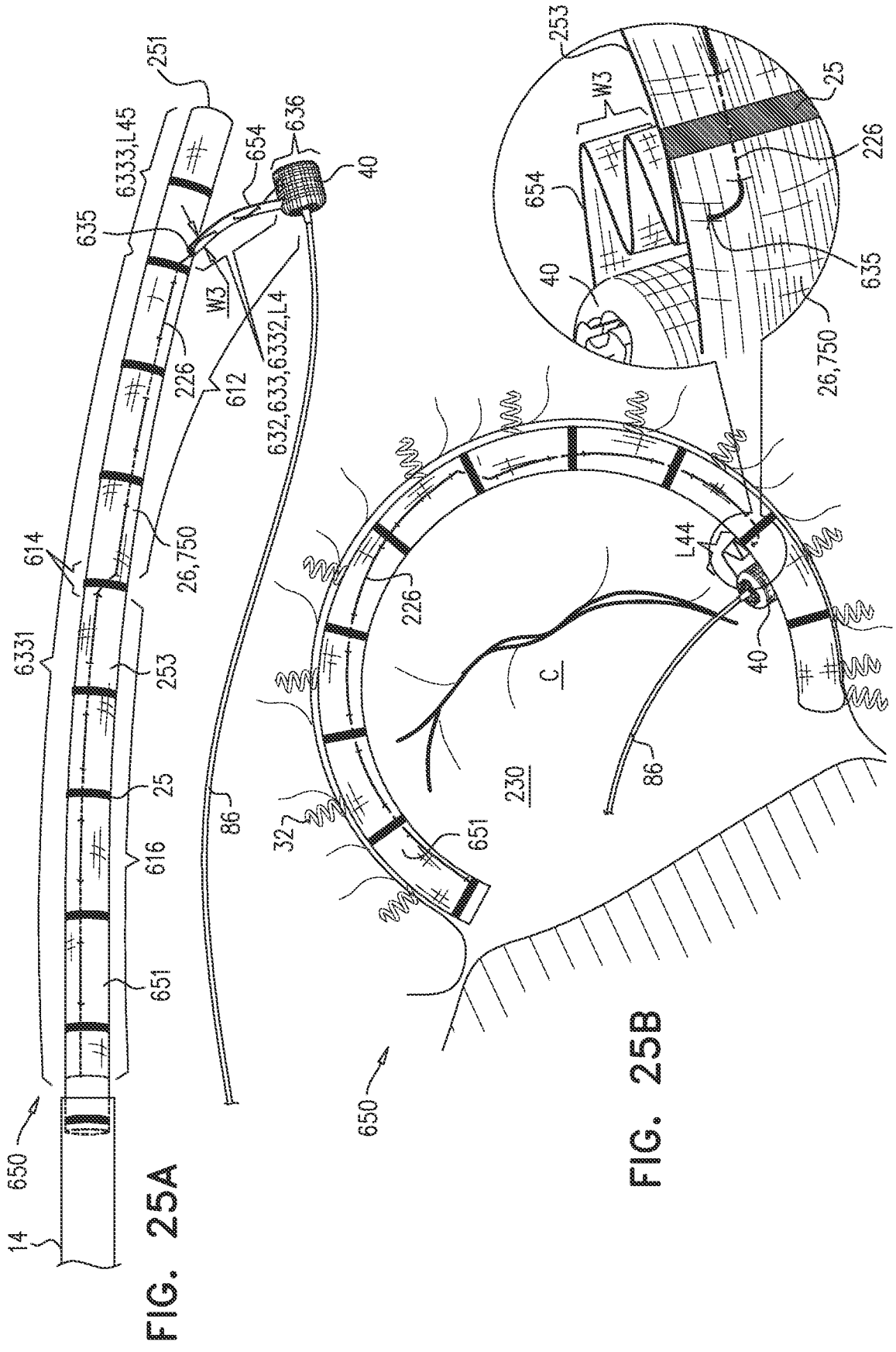
FIGS. 25A-B are schematic illustrations of an annuloplasty structure comprising a contraction-member protecting band, in accordance with some applications of the invention.

Reference is now made to FIGS. 25A-B, which are schematic illustrations of a system 640 comprising an implant configured for delivery into a heart of a subject, in accordance with some applications of the present invention. The implant comprises annuloplasty ring structure 651 (i.e., an implant, e.g., an annuloplasty band) comprising a flexible sleeve 26. It is to be noted that annuloplasty structure 651 is similar to structure 631 as described hereinabove with reference to FIGS. 23A-B, with the exception of structure 651 comprising a band 654. Sleeve 26 defines a primary body portion 750 of annuloplasty structure 641.

Band 654 defines contraction-member-protecting element 633 since second portion 6332 of contraction member 226 is woven, e.g., threaded, through band 654, and thereby band 654 protects portion 6332 of contraction member 226 and prevents interference of portion 6332 with actuation of adjustment mechanism 40. FIG. 25A shows structure 651 before contraction member 226 is fully pulled tight. In such a state, second portion 6332 is not pulled tight and band 654 is in a relaxed state and is not pressed against sleeve 26 (i.e., it is in an unpressed state). In the relaxed, unpressed state, band 654 defines a longitudinal length L4 of 10-15 mm measured along a longitudinal axis of the band, a width W3 of 3-5 mm, and a thickness of 0.1-0.3 mm. Typically, width W3 of band 654 is 10 times greater than a width of contraction member 226.

In the relaxed, unpressed state of band 654, adjustment mechanism 40 is distanced from sleeve 26 (i.e., the body portion of structure 631) by a distance of 10-15 mm which corresponds to longitudinal length L4, as shown in FIG. 25A. Typically, adjustment mechanism 40 is distanced from sleeve 26 via second portion 6332 of contraction member 226 and/or as shown, adjustment mechanism 40 is distanced from sleeve 26 via band 654 of contraction-member-protecting element 633.

For some applications of the present invention, contraction-member-protecting element 633 comprises a strip which functions as band 654.

When contraction member 226 is fully pulled tight by adjustment mechanism 40 (i.e., when there is an increase in the degree of tension of member 226), band 654 changes shape (e.g., compresses and/or is folded, as shown in FIG. 25B), in order to bring adjustment mechanism 40 closer to wall 253 of sleeve 26. During the pulling of contraction member 226, portion 6332 slides along the length of band 654 which protects and provides a path for the sliding of portion 6332 of contraction member 226 during the sliding of portion 6332 along band 654. Additionally, band 654 prevents entangling of portion 6332 during the pulling of contraction member 226.

During the pulling of contraction member 226, and the sliding of portion 6332 along band 654, at least a portion of band 654 is pressed against wall 253 of sleeve 26 and band 654 has a pressed longitudinal length L44 of 0.5-1.5 mm, e.g., 1 mm, measured along the longitudinal axis of band 654.

For some applications of the present invention, band 654 comprises the same material as sleeve 26, as described hereinabove with reference to FIG. 1. For some applications band 654 of contraction-member-protecting element 633 comprises a radiopaque material which functions as an adjustment indicator 632 which provides an indication of the adjustment of structure 651. As element 633 changes shape according to an increase or decrease in the degree of tension of contraction member 226 (i.e., portion 6332 passing along band 654), the radiopaque material in element 633 enables element 633 to function as indicator 632. As shown in FIG. 25B, a portion of indicator 632 is pressed against sleeve 26 of structure 651.

Adjustment indicator 632 is typically coupled to a body portion of the implant, for some applications of the present invention. For example, the implant comprises an annuloplasty ring structure having a body portion (e.g., sleeve 26), and indicator 632 is directly coupled to the body portion of the annuloplasty ring structure. As shown, indicator 632 is directly coupled to an external surface of the body portion of the annuloplasty ring structure.

It is to be noted that band 654 may be used in combination with any annuloplasty structure described herein (e.g., structures 222, 611, 631, 641, or any other annuloplasty structure described hereinbelow).

Reference is now made to FIGS. 23A-25B, which show adjustment mechanism 40 being coupled to contraction member 226 at a first end portion of contraction member 226, and indicator 632 being coupled to contraction member 226 at a second portion 6332 of contraction member 226. In FIGS. 23A-25B, second portion 6332 is adjacent to adjustment mechanism 40 such that indicator 632 and the radiopaque material are disposed adjacent to adjustment mechanism 40.

Figure 26A:
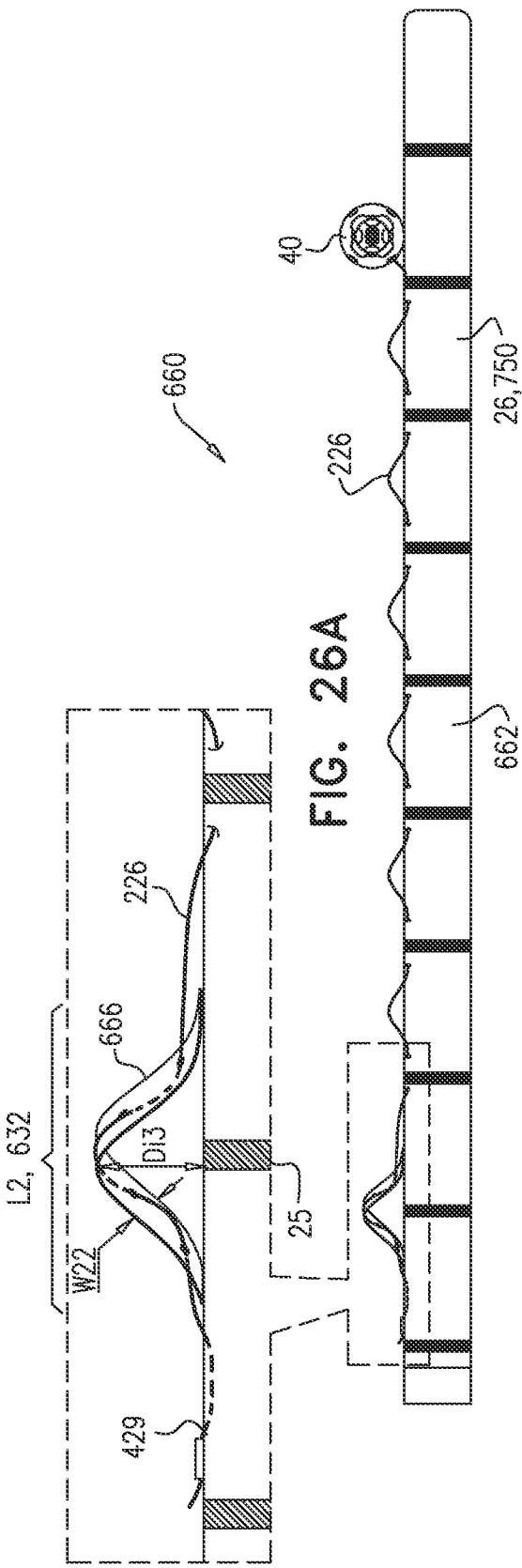
Figure 26B:
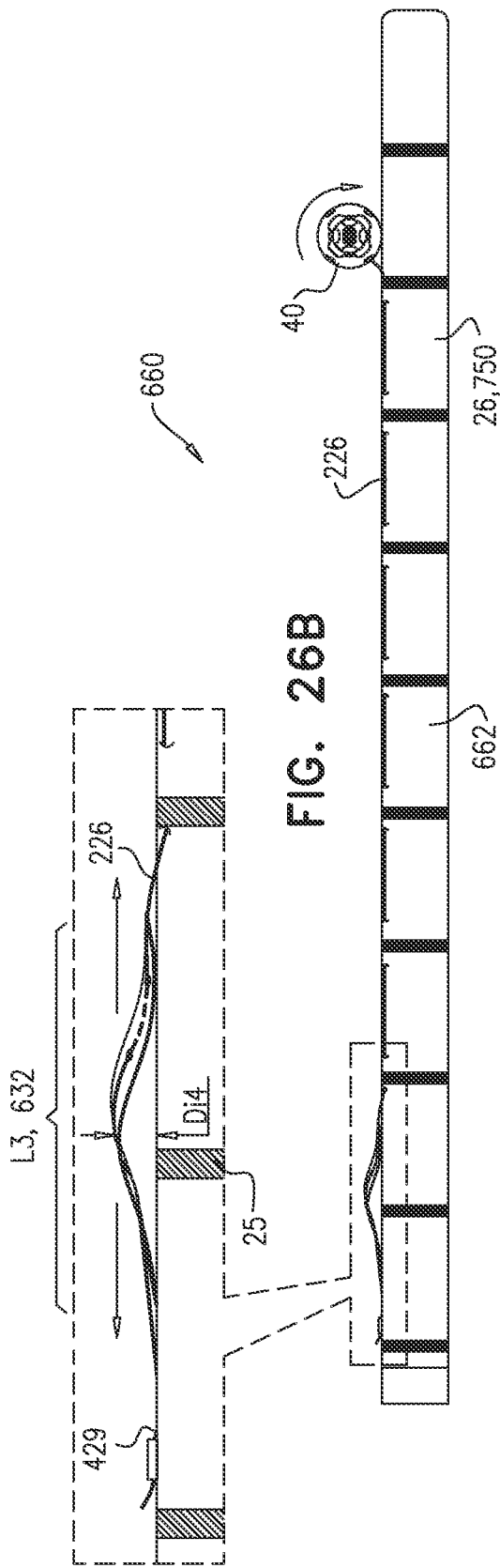

Reference is now made to FIGS. 26A-B, which are schematic illustrations of a system 660 comprising an annuloplasty structure 662 comprising adjustment indicator 632 which comprises an adjustment-indicator band 666, in accordance with some applications of the present invention. It is to be noted that structure 662 is similar to structure 222 described herein with the exception that structure 662 comprises band 666. Band 666 typically comprises a flexible material such as polyester and radiopaque material and provides an indication of contraction of contraction member 226 and of structure 662 in general. A portion of contraction member 226 adjacent end 429 of member 226 is threaded through band 666. That is, as shown in FIGS. 26A-B, adjustment mechanism 40 is coupled to contraction member 226 at a first end portion of contraction member 226, and indicator 632 is coupled to contraction member 226 at a second end portion of contraction member 226. Sleeve 26 defines a primary body portion 750 of structure 222.

Band 666 has a width W22 of 1-5 mm, e.g., 3 mm, and a thickness of 0.1-0.5 mm.

For some applications of the present invention, adjustment-indicator band 666 comprises a strip.

Adjustment indicator 632 is typically coupled to a body portion of the implant, for some applications of the present invention. For example, the implant comprises an annuloplasty ring structure having a body portion (e.g., sleeve 26), and indicator 632 is directly coupled to the body portion of the annuloplasty ring structure. As shown, indicator 632 is directly coupled to an external surface of the body portion of the annuloplasty ring structure.

FIG. 26A shows structure 662 before contraction member 226 is pulled tight. In such a state, band 666 is in a relaxed state and is not pressed against sleeve 26 (i.e., it is in an unpressed state). In the relaxed, unpressed state, band 666 defines a longitudinal length L2 of 4-6 mm measured along a longitudinal axis of band 666 from a first end of band 666 to a second end of band 666. In the relaxed, unpressed state of band 666, an upper portion of band 666, e.g., the apex of band 666, is distanced from sleeve 26 (i.e., the body portion of structure 662) by a distance Di3 of 2-4 mm.

As shown in FIG. 26B, when contraction member 226 is fully pulled tight by adjustment mechanism 40 (i.e., when there is an increase in the degree of tension of member 226), band 666 changes shape. That is, band 666 is flattened and at least a portion of band 666 is pressed closer to and against sleeve 26. During the flattening of band 666, as at least a portion of band 666 is pressed against sleeve 26, band 666 has a flattened, and pressed longitudinal length L3 of 7-10 mm measured along the longitudinal axis of band 666 from a first end of band 666 to a second end of band 666. In the flattened, pressed state of band 666, the upper portion of band 666, e.g., the apex of band 666, is closer to sleeve 26 (i.e., the body portion of structure 662) by a distance Di4 of 0-1 mm.

It is to be noted that adjustment-indicator band 666 may be used in combination with any annuloplasty structure described herein (e.g., structures 222, 611, 631, 641, 651, 711, 721, or any other annuloplasty structure described hereinbelow).

Reference is now made to FIGS. 27A-B, which are schematic illustrations of a system 670 comprising an annuloplasty structure 672, in accordance with some applications of the present invention. It is to be noted that structure 672 is similar to structure 222 described herein with the exception that structure 672 comprises adjustment indicator 632 which comprises a shape-deforming element 674 which comprises first and second arms 676. Element 674 typically comprises a flexible material such as stainless steel and comprises radiopaque material and provides an indication of contraction of contraction member 226 and of structure 672 in general. A portion of contraction member 226 adjacent end 429 of member 226 is coupled to element 674. That is respective portions of member 226 are coupled to (e.g., threaded through) each of arms 676 of element 674. That is, as shown in FIGS. 27A-B, adjustment mechanism 40 is coupled to contraction member 226 at a first end portion of contraction member 226, and indicator 632 is coupled to contraction member 226 at a second end portion of contraction member 226. Sleeve 26 defines a primary body portion 750 of structure 672.

Adjustment indicator 632 is typically coupled to a body portion of the implant, for some applications of the present invention. For example, the implant comprises an annuloplasty ring structure having a body portion (e.g., sleeve 26), and indicator 632 is directly coupled to the body portion of the annuloplasty ring structure. As shown, indicator 632 is directly coupled to an external surface of the body portion of the annuloplasty ring structure.

FIG. 27A shows structure 672 before contraction member 226 is pulled tight. In such a state, and element 674 is in a relaxed state and arms 676 are spaced apart from each other.

As shown in FIG. 27B, when contraction member 226 is fully pulled tight by adjustment mechanism 40 (i.e., when there is an increase in the degree of tension of member 226), element 674 changes shape in order to change a distance between first and second arms 676. That is, arms 676 are pulled closer toward each other and a distance between arms 676 is reduced. Conversely, when tension of contraction member 226 is reduced, tension on arms 676 is reduced and arms 676 are drawn away from each other and return to their resting state.

It is to be noted that shape-deforming element 674 may be used in combination with any annuloplasty structure described herein (e.g., structures 222, 611, 631, 641, 651, 711, 721, or any other annuloplasty structure described hereinbelow).

Reference is now made to FIGS. 28A-B, which are schematic illustrations of a system 680 comprising an annuloplasty structure 682, in accordance with some applications of the present invention. It is to be noted that structure 682 is similar to structure 222 described herein with the exception that structure comprises adjustment indicator 632 which comprises a receptacle 684 and a plug 686. Receptacle 684 is coupled to an outer surface of sleeve 26. Receptacle 684 and plug 686 comprise radiopaque material and provides an indication of contraction of contraction member 226 and of structure 682 in general. A portion of contraction member 226 adjacent end 429 of member 226 is coupled to plug 686. That is, as shown in FIGS. 28A-B, adjustment mechanism 40 is coupled to contraction member 226 at a first end portion of contraction member 226, and indicator 632 is coupled to contraction member 226 at a second end portion of contraction member 226. Sleeve 26 defines a primary body portion 750 of structure 682.

FIG. 28A shows structure 682 before contraction member 226 is pulled tight. In such a state, at least a majority of plug 686 is disposed outside of a space defined by receptacle 684.

As shown in FIG. 28B, when contraction member 226 is fully pulled tight by adjustment mechanism 40 (i.e., when there is an increase in the degree of tension of member 226), indicator 632 changes shape in order to position and fit plug 686 within the space defined by receptacle 684. Conversely, when tension of contraction member 226 is reduced, plug 686 is moved away from the space defined by receptacle 684.

Adjustment indicator 632 is typically coupled to a body portion of the implant, for some applications of the present invention. For example, the implant comprises an annuloplasty ring structure having a body portion (e.g., sleeve 26), and indicator 632 (e.g., at least receptacle 684) is directly coupled to the body portion of the annuloplasty ring structure. As shown, indicator 632 (e.g., at least receptacle 684) is directly coupled to an external surface of the body portion of the annuloplasty ring structure.

It is to be noted that receptacle 684 and plug 686 may be used in combination with any annuloplasty structure described herein (e.g., structures 222, 611, 631, 641, 651, 711, 721, or any other annuloplasty structure described hereinbelow).

Figure 29A:
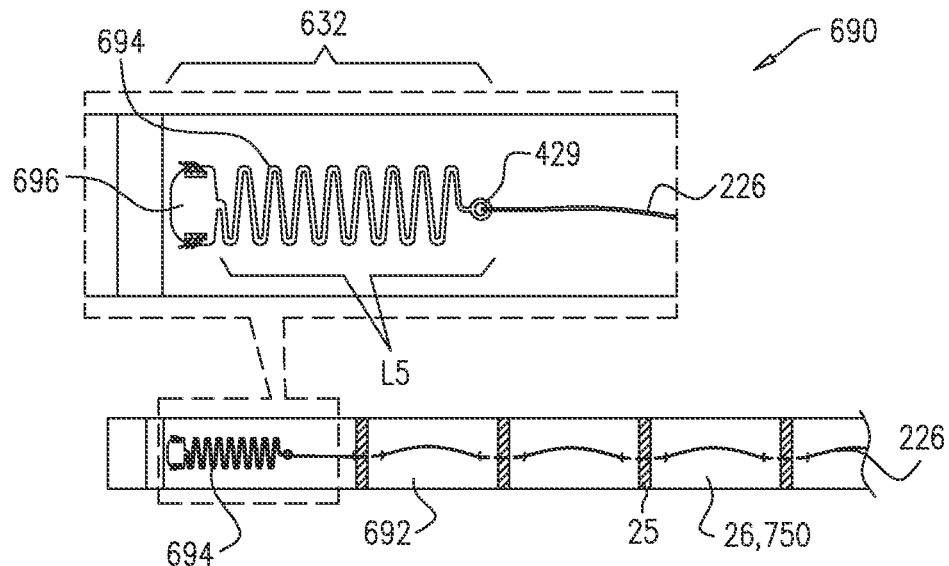
Figure 29B:
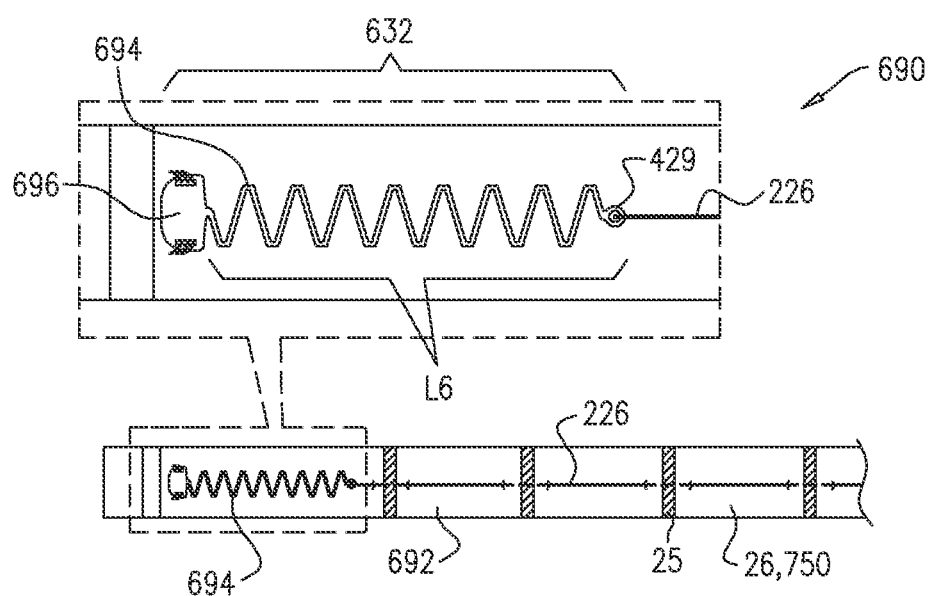

Reference is now made to FIGS. 29A-B, which are schematic illustrations of a system 690 comprising an annuloplasty structure 692 comprising adjustment indicator 632 which comprises an adjustment-indicator spring 694, in accordance with some applications of the present invention. It is to be noted that structure 692 is similar to structure 222 described herein with the exception that structure 692 comprises spring 694. Spring 694 typically comprises a flexible material such as stainless steel and radiopaque material and provides an indication of contraction of contraction member 226 and of structure 692 in general. For some applications, spring 694 comprises a folded spring with peaks and valley, as shown in FIGS. 29A-B. For some applications, spring 694 comprises a helical spring. For some applications, spring 694 comprises a telescoping spring, e.g., a volute spring or any other telescoping spring. Sleeve 26 defines a primary body portion 750 of structure 692.

A portion of contraction member 226 adjacent end 429 of member 226 is coupled to one end of spring 694. A second end of spring 694 comprises a sleeve coupler 696 which fixedly couples the second end of spring 694 to sleeve 26. As shown in FIGS. 29A-B, adjustment mechanism 40 is coupled to contraction member 226 at a first end portion of contraction member 226, and indicator 632 is coupled to contraction member 226 at a second end portion of contraction member 226.

FIG. 29A shows structure 662 before contraction member 226 is pulled tight. In such a state, spring 694 is in a relaxed, unpulled state. In the relaxed, unpulled state, spring 694 defines a longitudinal length L5 of 2-4 mm measured along a longitudinal axis of spring 694 from the first end of spring 694 to a second end of spring 694 before coupler 696.

As shown in FIG. 29B, when contraction member 226 is fully pulled tight by adjustment mechanism 40 (i.e., when there is an increase in the degree of tension of member 226), spring 694 changes shape. That is, spring 694 is pulled longitudinally and is stretched. During the pulling of spring 694, spring 694 has a pulled longitudinal length L5 of 6-8 mm measured along the longitudinal axis of spring 694 from the first end of spring 694 to the second end of spring 694 before coupler 696. For some applications of the present invention, markers 25 are used as reference points for how far spring 694 is pulled.

Adjustment indicator 632 is typically coupled to a body portion of the implant, for some applications of the present invention. For example, the implant comprises an annuloplasty ring structure having a body portion (e.g., sleeve 26), and indicator 632 is directly coupled to the body portion of the annuloplasty ring structure. As shown, indicator 632 is directly coupled to an external surface of the body portion of the annuloplasty ring structure.

It is to be noted that adjustment-indicator spring 694 may be used in combination with any annuloplasty structure described herein (e.g., structures 222, 611, 631, 641, 651, 711, or 721).

Figure 30:
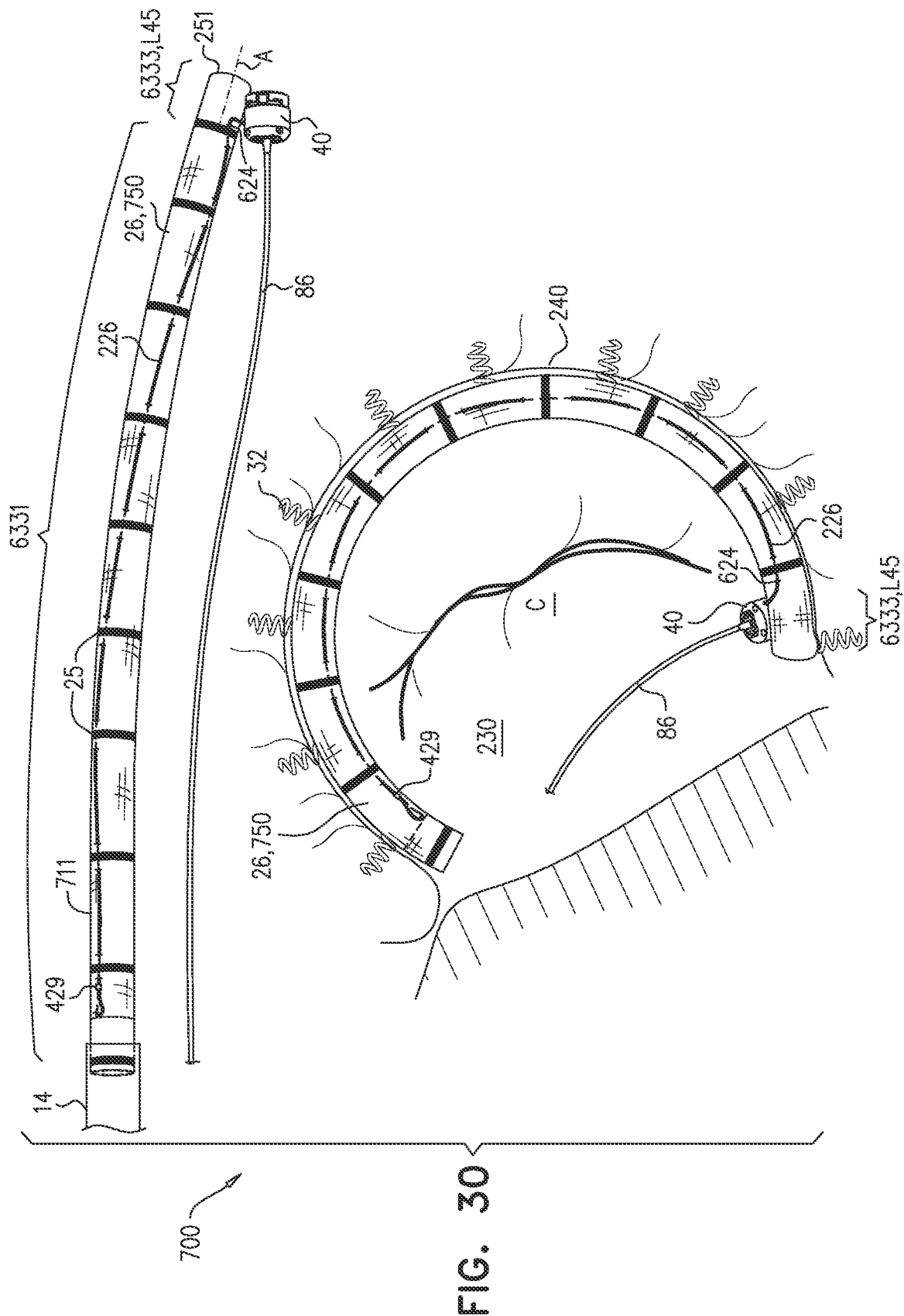
FIG. 30 is a schematic illustration of an annuloplasty structure in and a contraction member disposed helically with respect to the sleeve of the annuloplasty structure, in accordance with some applications of the invention.

Reference is now made to FIG. 30, which is a schematic illustration of a system 700 comprising an implant configured for delivery into a heart of a subject, in accordance with some applications of the present invention. The implant comprises an annuloplasty ring structure 711 (i.e., an implant, e.g., an annuloplasty band) comprising flexible sleeve 26 and an adjustment mechanism 40 (as described hereinabove with regard to structure 222, with reference to FIG. 1).

Structure 711 is similar to structure 222 with the exception that contraction member 226 is coupled to sleeve 26 in a manner in which at least a part of contraction member 226 is disposed helically around longitudinal axis A of sleeve 26 of structure 222 in the absence of torsion or twisting applied to sleeve 26. For some applications, at least 50%, e.g., at least 60% of contraction member 226 is disposed helically around axis A. Sleeve 26 defines a primary body portion 750 of structure 711. Sleeve 26 has a lateral wall through which contraction member 226 is woven.

As shown, contraction member 226 extends along first portion 6331 which defines the contracting portion of sleeve 26. Contraction member 226 extends along at least the contracting portion of sleeve 26 at an angle of twist between a proximal end and a distal end of sleeve 26 that is 170-190 degrees, e.g., 180.

As shown in the upper image of FIG. 30, second end 429 of contraction member 226 is at a distance of between 2.5 and 3.5 radians from location 624 along sleeve 26 at which contraction member 226 exits away from sleeve 26 and to adjustment mechanism 40. An angle of twist between second end 429 of contraction member 226 and location 624 is between 170 and 190 degrees, e.g., 180 degrees. That is, adjustment mechanism 40 is positioned from second end 429 of contraction member 226 at an angle of between 140-180 degrees, e.g., between 155 and 175 degrees from second end 429 of contraction member 226.

Additionally, once structure 711 is curved to correspond to the shape of the annulus, as shown in the lower image of FIG. 30, the helical coupling of contraction member 226 to sleeve 26, enables structure 711 to assume a configuration in which the entire contraction member 226 is disposed along an inner perimeter of structure 711 (i.e., facing center C) and not along any portion of the outer perimeter of structure 711. As such, the configuration prevents entangling of member 226 with any anchor that is anchored through sleeve 26 at the outer perimeter of structure 711, as described hereinabove, for example, with reference to FIGS. 3A-G and 4A-B.

Figures 31A, 31B:
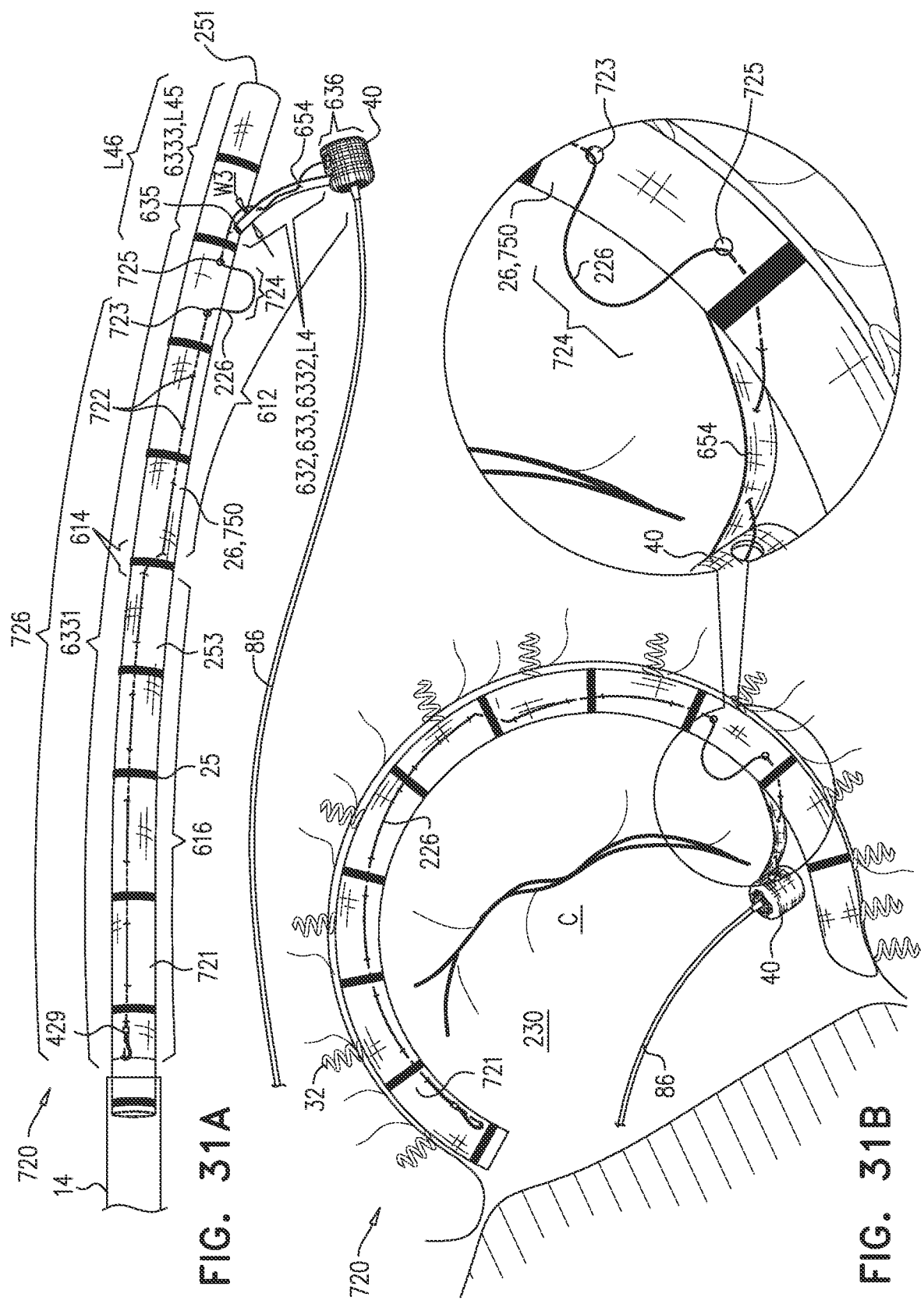
FIGS. 31A-C are schematic illustrations of an annuloplasty structure in being shaped so as to define holes, in accordance with some applications of the invention.
Figure 31C:
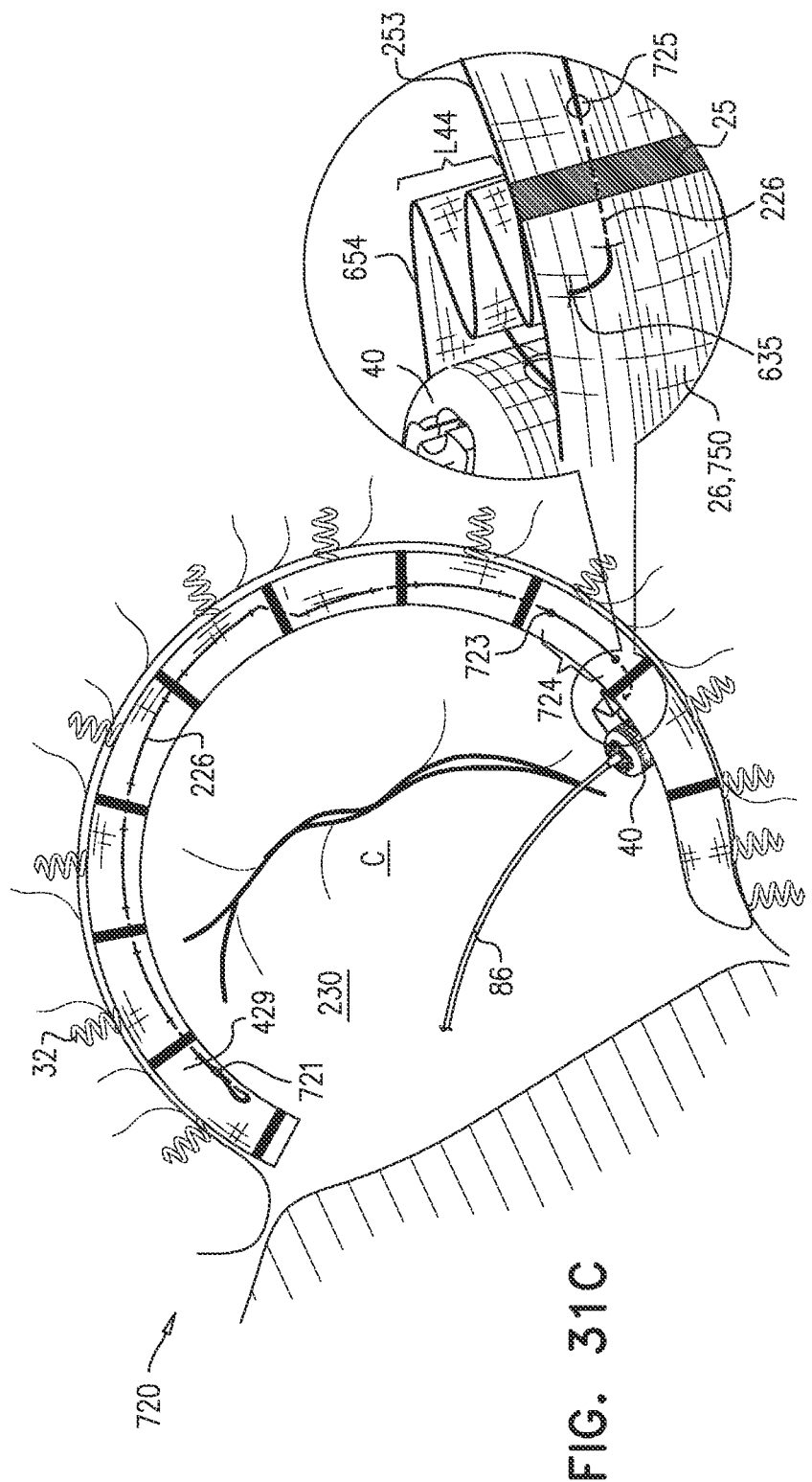

Reference is now made to FIGS. 31A-C, which are schematic illustrations of a system 720 comprising an implant configured for delivery into a heart of a subject, in accordance with some applications of the present invention. The implant comprises an annuloplasty ring structure 721 (i.e., an implant, e.g., an annuloplasty band) comprising flexible sleeve 26 and an adjustment mechanism 40 (as described hereinabove with regard to structure 222, with reference to FIG. 1). Sleeve 26 defines a primary body portion 750 of structure 721.

Structure 711 is similar to structure 651 described hereinabove with reference to FIG. 25, with the exception that sleeve 26 is shaped so as to define first and second holes 723 and 725 in a vicinity of contraction-member-protecting element 633. Typically, holes 723 and 725 are disposed in a vicinity of connection point 635. A portion of contraction member 226 exits sleeve 26 from hole 723 and reenters the lumen of sleeve 26 through hole 725. That is, the portion of contraction member 226 exits away from primary body portion 750 of structure 721 through first hole 723 and reengages primary body portion 750 of structure 721 through second hole 725. Typically, second hole 725 is disposed at a distance L46 of 16-22 mm from end wall 251 of primary body portion 750 (e.g., sleeve 26). Typically, holes 723 and 725 are 0.3-0.7 mm in diameter.

A majority of contraction member 226 is threaded through sleeve 26 and woven in and out of the lumen of sleeve 26 through a plurality of threading points 722. Threading points 722 are areas of sleeve 26 through which contraction member 226 is threaded. In addition to threading points 722, sleeve 26 defines holes 723 and 725 which are larger than the openings provided by points 722. That is there is less friction between sleeve 26 and contraction member 226 at holes 723 and 725 than there is at threading points 722. Thus, structure 721 defines a first portion 726 having a first degree of friction between primary body portion 750 (e.g., sleeve 26) and a first portion of contraction member 226, and structure 721 defines a second portion 724 having a second degree of friction between primary body portion 750 (e.g., sleeve 26) and a second portion of contraction member 226. The second degree of friction is less than the first. Typically, when contraction member 226 is not pulled fully tight as shown in FIGS. 31A-B, second portion 724 defines a contraction-member-free section of primary body portion 750 (e.g., sleeve 26) that is between first and second holes 723 and 725.

As shown in FIG. 31B, during the placement of sleeve 26 around annulus 240, sleeve 26 is curved and sleeve 26 initially passively contracts to conform to the shape of annulus 240. During the initial contraction (i.e., the contraction performed passively in response to placing sleeve 26 around annulus 240, and not by actuation of adjustment mechanism 40), the contracted shape of sleeve 26 does not accommodate the length of contraction member 226 as it had in its linear state (shown in FIG. 31A). As such, a portion of contraction member 226 is forced a bit out outside of primary body portion 750 (e.g., sleeve 26) through holes 723 and 725. Holes 723 and 723 thereby accommodate and encourage the movement of the excess portion of contraction member 226 during the curving of sleeve 26 responsively to the anchoring of sleeve 26 along the annulus, and prior to actuation of adjustment mechanism 40. Holes 723 and 725 enable the excess portion of contraction member 226 to exit away from a surface of the annuloplasty structure at a location of the structure that is along primary body portion 750 (e.g., sleeve 26) of the annuloplasty structure and not at adjustment mechanism 40, which is advantageous because the excess portion of contraction member 226 exiting along primary body portion 750 of the annuloplasty structure typically does not interfere with the function of the adjustment mechanism 40.

FIG. 31C shows structure 721 in a fully-contracted state in which contraction member 226 is pulled tight even at second portion 724 of structure 721 that is between first and second holes 723 and 725.

During the pulling of member 226 responsively to actuation of adjustment mechanism 40, contraction member 226 slides freely and with minimal friction through holes 723 and 725 relatively to the sliding of contraction member 226 through threading points 722 which occurs with more friction.

It is to be noted that system 710 may be used in combination with any annuloplasty structure described herein (e.g., structures 222, 611, 631, 641, 651, or 711).

It is to be noted that any of the apparatus or methods described herein may be used in combination with those described in PCT application publication WO 2014/064694, which is incorporated herein by reference in its entirety.

The invention claimed is:

1. A method for use with a heart of a subject, the heart having a valve and an atrium upstream of the valve, the method comprising:
using a driver, transluminally advancing, via a catheter, to the atrium, a first tissue anchor coupled to the driver;
using the driver, securing a portion of an elongate contraction member to an annulus of the valve by anchoring the first tissue anchor to the annulus while successive portions of the elongate contraction member remain disposed within the catheter;
subsequently, securing the elongate contraction member at least partly around the annulus by:
feeding the successive portions of the elongate contraction member out of the catheter into the atrium, and
using the driver, advancing further tissue anchors in the atrium and securing the successive portions to the annulus by anchoring the further tissue anchors to the annulus, such that the first tissue anchor and the further tissue anchors are distributed along the elongate contraction member;
subsequently, contracting the annulus by applying tension to the elongate contraction member, such that a radiopaque indicator including a volute spring that is disposed within the heart and that is coupled to the contraction member undergoes a conformational change in response to the tension;
observing the conformational change of the radiopaque indicator within the heart; and
adjusting the tension responsively to the observed conformational change.

2. The method according to claim 1, wherein securing the contraction member at least partly around an annulus of the valve comprises securing the contraction member only partly around an annulus of the valve.

3. The method according to claim 1, wherein transluminally advancing the further tissue anchors to the atrium comprises sequentially, for each of the further tissue anchors, engaging the anchor with the anchor driver, introducing the anchor into the subject, and advancing the anchor to the successive portions of the elongate contraction member in the atrium.

4. The method according to claim 1, wherein anchoring the further tissue anchors to the annulus comprises sequentially anchoring each of the further tissue anchors to the annulus.

5. The method according to claim 1, further comprising transluminally placing the radiopaque indicator within the atrium, coupled to the contraction member, and wherein observing the conformational change of the radiopaque indicator within the heart comprises observing the conformational change of the radiopaque indicator within the atrium.

6. The method according to claim 1, wherein the conformational change is shortening of the radiopaque indicator in response to increase in the tension, and wherein observing the conformational change comprises observing the shortening of the radiopaque indicator in response to increase in the tension.

7. The method according to claim 1, wherein the conformational change is lengthening of the radiopaque indicator in response to increase in the tension, and wherein observing the conformational change comprises observing the lengthening of the radiopaque indicator in response to increase in the tension.

8. The method according to claim 1, wherein the radiopaque indicator includes a sleeve through which the contraction member is disposed, the conformational change is a change in longitudinal length of the sleeve, and observing the conformational change comprises observing the change in longitudinal length of the sleeve.

9. The method according to claim 8, wherein the change in length of the sleeve is shortening of the sleeve in response to increase in the tension, and observing the change in length of the sleeve comprises observing shortening of the sleeve in response to increase in the tension.

10. The method according to claim 1, wherein the spring is shaped to define a path along a longitudinal axis of the spring, the radiopaque indicator is coupled to the contraction member by the contraction member being disposed along the path through the spring, and observing the conformational change comprises observing the conformational change of the spring that is shaped to define the path along which the contraction member extends through the spring.

11. The method according to claim 1, wherein the radiopaque indicator includes a first component and a second component, and wherein observing the conformational change of the radiopaque indicator comprises observing a change in juxtaposition between the first component and the second component.

12. The method according to claim 11, wherein observing the change in juxtaposition between the first component and the second component comprises observing a reduction in distance between the first component and the second component in response to increase in the tension.

13. The method according to claim 1, wherein the step of securing comprises progressively securing the successive portions of the elongate contraction member to the annulus by, for each portion, successively:
- positioning the portion at a corresponding site of the annulus, and
- subsequently, securing the portion to the site.

14. The method according to claim 1, wherein the step of securing comprises progressively securing the successive portions of the elongate contraction member to the annulus by, for each portion, successively:
- positioning a corresponding tissue anchor at the portion, and
- subsequently, securing the portion to a corresponding site of the annulus by anchoring the corresponding tissue anchor to the site.

* * * * *